United States Patent [19]

Dorn

[11] Patent Number: 5,108,927
[45] Date of Patent: * Apr. 28, 1992

[54] SPECIMEN TRANSPORT DEVICE CONTAINING A SPECIMEN STABILIZING COMPOSITION

[75] Inventor: Gordon L. Dorn, Dallas, Tex.

[73] Assignee: Wadley Technologies, Inc., Dallas, Tex.

[*] Notice: The portion of the term of this patent subsequent to Dec. 3, 2008 has been disclaimed.

[21] Appl. No.: 269,490

[22] Filed: Nov. 9, 1988

Related U.S. Application Data

[63] Continuation-in-part of Ser. No. 772,954, Sep. 4, 1985, abandoned, which is a continuation-in-part of Ser. No. 525,164, Aug. 23, 1983, abandoned, which is a continuation-in-part of Ser. No. 431,776, Sep. 30, 1982, abandoned.

[51] Int. Cl.$^5$ .......................... C12M 1/24; C12N 1/00; B65D 81/00
[52] U.S. Cl. .................... 435/296; 435/299; 435/243; 128/760; 128/765
[58] Field of Search ................ 435/4, 29, 34, 296, 435/286, 284, 243, 299; 128/760, 764, 765; 604/214, 220

[56] References Cited

U.S. PATENT DOCUMENTS

| | | | |
|---|---|---|---|
| 3,875,012 | 4/1975 | Dorn et al. | 435/34 |
| 3,898,132 | 8/1975 | Hettrick . | |
| 3,930,492 | 1/1976 | Hatsuno et al. | 128/764 |
| 4,030,978 | 6/1977 | Abramson . | |
| 4,105,498 | 8/1978 | Hertl et al. . | |
| 4,145,308 | 3/1979 | Melnick et al. | 435/30 |
| 4,192,320 | 3/1980 | Megahed | 128/764 |
| 4,212,948 | 7/1980 | Dorn | 435/34 |
| 4,246,898 | 1/1981 | Travalent et al. | 604/220 |
| 4,248,634 | 2/1981 | Foerster . | |
| 4,336,880 | 6/1982 | Mehl . | |
| 4,340,679 | 7/1982 | Fukui et al. . | |
| 4,370,987 | 2/1983 | Bazell et al. | 128/760 |
| 4,391,887 | 7/1983 | Baumgarten et al. . | |
| 4,529,702 | 7/1985 | Bryan . | |
| 4,617,941 | 10/1986 | Ichikawa et al. | 128/765 |
| 4,642,102 | 2/1987 | Ohmori | 604/220 |
| 4,699,614 | 10/1987 | Glazier | 604/110 |
| 4,720,460 | 1/1988 | Barach et al. . | |
| 4,726,950 | 2/1988 | Desai et al. . | |
| 4,758,323 | 7/1988 | Chak | 128/765 |
| 4,768,653 | 9/1988 | Desai et al. . | |
| 4,883,466 | 11/1989 | Glazier | 604/110 |

OTHER PUBLICATIONS

Lennette et al., Manual of Clinical Microbiology, 2nd ed., Washington, D.C., American Soc. for Microbiol., (1974), pp. 60–63, 72, 73, 402, 403, 882, 883.

Gottschalk et al., 73 Chemical Abstracts, 75236 Ex (1970).

Bartlett et al., "Bacteriological Swabs", *British Medical Journal*, 450–51 (Aug. 23, 1969).

Ellner et al., "Survival of Bacteria on Swabs", *J. Bacteriology*, vol. 91, 905–06 (Feb. 1966).

(List continued on next page.)

*Primary Examiner*—David L. Lacey
*Assistant Examiner*—William K. Y. Chan
*Attorney, Agent, or Firm*—Richards, Medlock & Andrews

[57] ABSTRACT

The improvement of specimen quality for microbial analysis is addressed by the present invention which discloses a chemical composition for use in a method and apparatus for transporting a specimen suspected to contain microorganisms of interest to a laboratory for analysis and improved methods of analysis.

A device and method for taking, storing, and preserving fluid samples is disclosed comprising a container and a composition designed to maintain the level of microorganisms present in a specimen during transportation of the specimen to a testing facility.

The method and apparatus can be utilized on all types of aqueous specimens and specimens which may be extracted in aqueous solution for analysis of microorganisms therein.

14 Claims, 6 Drawing Sheets

OTHER PUBLICATIONS

Brook, "Comparison of Two Transport Systems for Recovery of Aerobic and Anaerobic Bacteria from Abscesses", 25 *J. Clinical Microbiology*, 2020-22.

Ajello et al., "Trans-Isolate Medium: A New Medium for Primary Culturing and Transport of *Neisseria meningitidis, Streptococcus pneumoniae* and *Haemophilus influenzae*", *J. Clinical Microbiology*, 55-58 (Jul. 1984).

Helsta et al., "Recovery of Anaerobic, Facultative, and Aerobic Bacteria from Clinical Specimens in Three Anaerobic Transport Systems", 5 *J. Clinical Microbiology*, pp. 564-569 (Jun. 1977).

Amies, "A Modified Formula for the Preparation of Stuart's Transport Medium", 58 *Canadian Journal of Public Health*, pp. 296-300 (Jul. 1967).

McConville et al., "Comparison of Three Transport Systems for Recovery of Aerobes and Anaerobes from Wounds", 72 *Am. Society of Clinical Pathologists*, 968-71 (Dec. 1979).

Cooper, "The Prolonged Survival of Upper Respiratory Tract and Intestinal Pathogens on Swabs", *J. Clin. Path.*, vol. 10, 226-30 (1957).

Rubbo et al., "Some Observations on Survival of Pathogenic Bacteria on Cotton-Wool Swabs", *British Medical Journal*, 983-87 (May 5, 1951).

Short et al., "Anaerobic Survival of Clinical Isolates and Laboratory Strains of *Neisseria gonorrhoeae:* Use in Transfer and Storage", 15 *J. Clinical Microbiology*, 915-19 (May 1982).

Ringertz et al., "Use of the Antimicrobial Removal Device Prior to Blood Culture in Patients on Antibiotic Therapy", 4 *Eur. J. Clin. Microbiol.*, 544-47 (Dec. 1985).

Weinberg et al., "Effectiveness of the Antimicrobial Removal Device, BACTEC 16B Medium, and Thiol Broth in Neutralizing Antibacterial Activities of Imipenem, Norfloxacin, and Related Agents", 19 *J. Clinical Microbiology*, 207-09 (Feb. 1984).

McGuire et al., "Evaluation of the BACTEC Antimicrobial Removal System for Detection of Bacteremia", *J. Clinical Microbiology*, vol. 18, 449-51 (Sept. 1983).

Smith et al., "In Vitro Evaluation of the BACTEC Resin-Containing Blood Culture Bottle", 17 *J. Clin. Microbiology*, 1120-26 (Jun. 1983).

Wright et al., "The Antimicrobial Removal Device, a Microbiological And Clinical Evaluation", *American Journal of Clinical Pathology*, vol. 78, 173-77 (Aug. 1982).

Appleman et al., "Evaluation of the Antibiotic Removal Device", 15 *J. of Clinical Microbiology*, 278-81 (Feb. 1982).

Lindsey et al., "In Vitro Antibiotic Removal and Bacterial Recovery from Blood with an Antibiotic Removal Device", 13 *Journal of Clinical Microbiology*, 503-07 (Mar. 1981).

Melnick, "Improvement in Diagnosis of Bacteremia", *Infectious Diseases* 1 (May 1980).

Tilton, "The Laboratory Approach to the Detection of Bacteremia", 36 *Ann. Rev. Microbiol.*, 467-93 (1982).

Belding et al., "Effect of Sodium Polyanethole-Sulfonate on Antimicrobial Systems in Blood", 24 *Applied Microbiology*, 691-98 (Nov. 1972).

Edberg et al., "Use of Sodium Polyanethol Sulfonate to Selectively Inhibit Aminoglycoside and Polymyxin Antibiotics in a Rapid Blood Level Antibiotic Assay", 9 *Antimicrobial Agents and Chemotherapy*, 414-17 (Mar. 1976).

W. H. Traub et al., "Media Dependent Antagonism of Gentamicin Sulfate by Liquoid (Sodium Polyanetholsulfonate)", *Experientia* 25/11, p. 1184.

Russell et al., "Laboratory Uses of Antibiotic-Inactivating Enzymes", 14 *J. Antimicrobial Chemotherapy*, 567-70 (1984).

Simberkoff et al., "Inactivation of Penicillins by Carbohydrate Solutions at Alkaline pH", *New England Journal of Medicine*, 116-19 (Jul. 16, 1976).

McKee et al., "A Comparison of the Value of Clarase, Penicillinase, and Cysteine Hydrochloride in Revealing the Presence of Contaminating Organisms in Preparations of Penicillin", 51 *J. Immunology*, 127-131 (1945).

Chow et al., "Inactivation of the Antibiotic Activity of Penicillin by Cysteine Hydrochloride. I. Chemical Aspects of Inactivation", 58 *Proc. Soc. Exp. Biol. and Med.*, 175-177 (1945).

Mou et al., "The Enumeration and Preservation of Bacteria in Urine", 35 *American Journal of Clinical Pathology*, 572-75 (Jun. 1961).

(List continued on next page.)

OTHER PUBLICATIONS

Fuchs, "Effect of Storage on Urine Culture", 18 *Medical Laboratory Observer*, p. 12 (Jul. 1986).

Hindman et al., "Effect of Delay on Culture of Urine", 4 *J. Clinical Microbiology*, 102-03 (Jul. 1976).

Traub et al., "Bactericidal Activity of Antimicrobial Drugs in Simulated Urine Specimens at Various Temperatures of Incubation", 255 *Zbl. Bakt. Hyg., I. Abt. Orig. A.*, 494-502 (1983).

Goodman et al., "A Urine Preservative System to Maintain Bacterial Counts", *Clinical Pediatrics*, 383-86, vol. 24 (Jul. 1985).

Weinstein, "Clinical Evaluation of a Urine Transport Kit with Lyophilized Preservative for Culture, Urinalysis, and Sediment Microscopy", *Diagn. Microbiol. Infect. Dis.*, vol. 3, 501-08 (1985).

Lauer et al., "Effect of Chemical Preservation of Urine on Routine Urinalysis and Non-Culture Test for Bacteriuria", 40 *Institute of Medical Laboratory Sciences*, 27-32 (1983).

Watson et al., "Laboratory Assessment of Physical and Chemical Methods of Preserving Urine Specimens", 30 *J. Clinical Pathology*, 532-36 (1977).

Pezzlo et al., "Effect of the B-D Urine Culture Kit on an Automated Bacteriuria Screen", 20 *J. Clinical Microbiology*, 1207-08 (Dec. 1984).

Southern et al., "Use of the Becton-Dickinson Urine Culture Tube with the Abbott MS-2 Urine Screening System", 2 *Diagn. Microbiol. Infect. Dis.*, 193-98 (1984).

Hubbard et al., "Comparison of the B-D Urine Culture Kit with a Standard Culture Method and with the MS-2", *J. of Clinical Microbiology*, vol. 17, 327-31 (FEb. 1983).

Guenther et al., "Evaluation of the B-D Urine Culture Kit", 14 *Journal of Clinical Microbiology*, 628-30 (Dec. 1981).

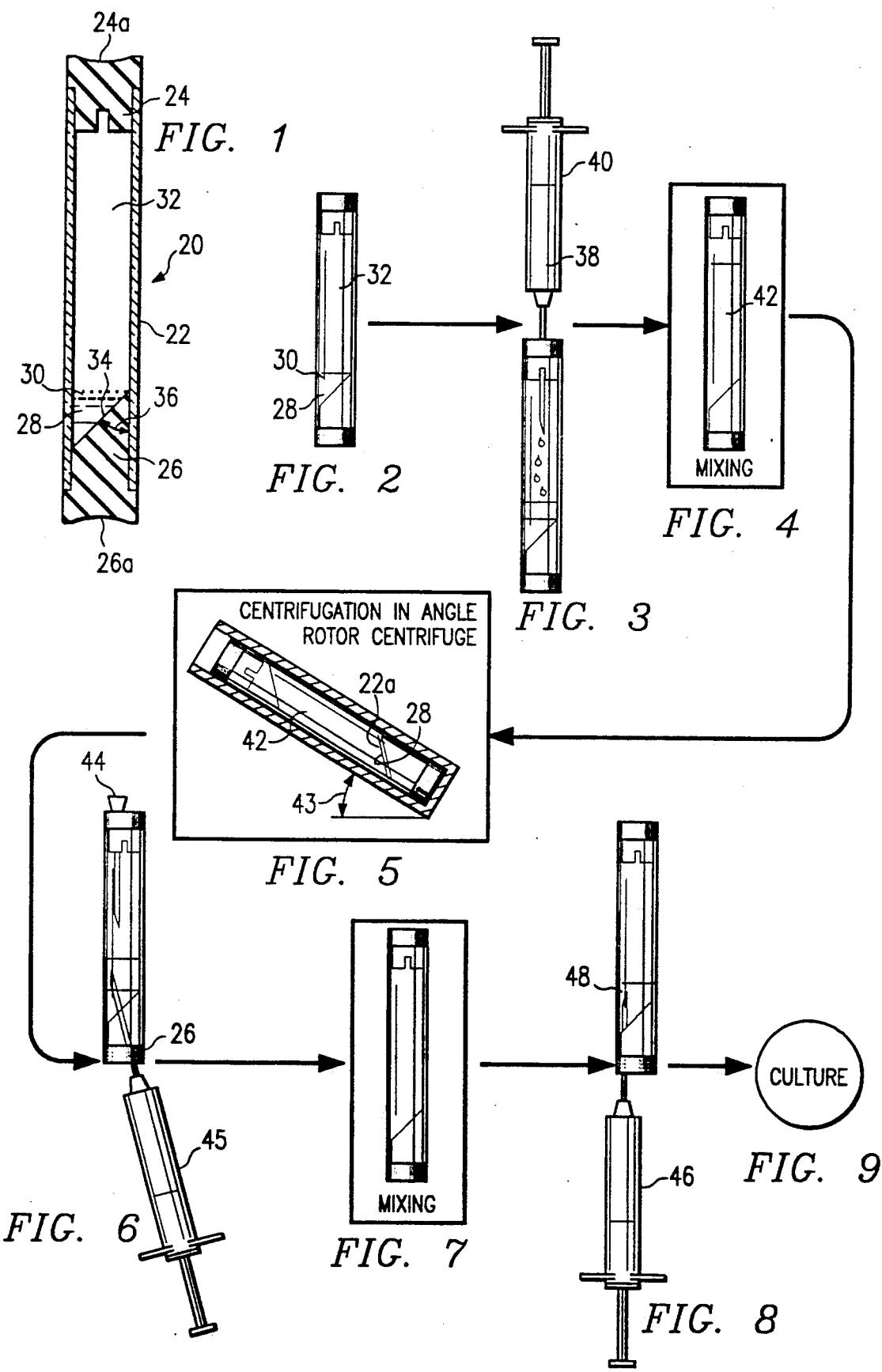

1

SPECIMEN TRANSPORT DEVICE CONTAINING A SPECIMEN STABILIZING COMPOSITION

This is a continuation-in-part of copending application Ser. No. 06/772954 filed Sep. 4, 1985, now abandoned, which is a continuation-in-part of copending application Ser. No. 06/525164 filed Aug. 23, 1983, now abandoned, which is a continuation-in-part of copending application Ser. No. 06/431776, filed Sep. 30, 1982, now abandoned.

TECHNICAL FIELD

This invention relates to the field of analysis of microorganisms in a specimen. In particular, this invention relates to maintaining the quality or microbial integrity of a specimen from the time of collection to the time laboratory analysis is initiated.

BACKGROUND ART

Accurate laboratory analysis of specimens suspected of containing microorganisms is of utmost importance in the fields of medicine and food technology and safety, among others. While techniques have been developed for improving the rapidity and sensitivity of microbiological identification, drugs have been developed for fighting infection in patients, and sanitary conditions for food processing have become mandated by law, it is evident that problems remain.

For example, septicemia, which is the presence of pathogenic microorganisms in the blood, is one of the most serious types of infections encountered. There is unanimous agreement in the medical profession that septicemia is second only to meningitis in terms of serious infections. Even though modern medicine has provided an armament of antibiotics and antifungal drugs, the mortality rate from septicemia is approximately twenty-five percent. Also, when shock accompanies septicemia, the mortality rate increases to over sixty percent. Debilitating diseases, major surgery, administration of immunosuppressive drugs or anticancer medications cause patients to be particularly prone to septicemia. Early diagnosis of the causative agent in conjunction with the use of the appropriate antibiotic therapy is essential in fighting septicemia. Consequently, it is imperative that the physician know as rapidly as possible, not only that the patient has septicemia, but also the identity and/or antibiotic susceptibility of the microorganisms involved. Thus, proper and timely diagnosis of septicemia depends upon very rapid and efficient analysis of the microorganisms in patient's blood. Further, it is necessary during the analysis of the microorganisms in the patient's blood that the blood sample not be contaminated with microorganisms from the hospital environment Another example of a disorder caused by microorganisms is the presence of pathogenic microorganisms in the urine, which occurs most commonly in infants, pregnant women, patients with obstructive lesions, following the use of instrumentation in the urinary tract (such as catheters), or with urologic diseases affecting micturition. This disorder can result in a localized infection within the bladder or kidneys When confined to the bladder, the infection is usually well controlled by antimicrobial therapy Once the kidneys are infected, however, lesions may continue to progress despite treatment leading to chronic pyelonephritis and septicemia.

In the field of food technology, contamination occasionally becomes a problem that endangers human health Contamination of milk, for example, has been known to occur even where a processing step to kill harmful microorganisms is employed because equipment malfunctions, human error, and sometimes mysterious circumstances contribute to processing ineffectiveness. In such cases, rapid and accurate analysis of specimens from the food processing apparatus and the food itself are important in establishing the cause of the contamination so that the process may be remedied. Various techniques are utilized for analysis of microorganisms. Simple quantitative analysis involves determining the number of microorganisms in a given specimen regardless of microorganism identity. Quantitation may be accomplished by introducing a known volume of specimen (perhaps diluted by a known amount in a nutrient broth) onto a nutrient agar and allowing formation of colonies It may be desirable to determine the identity and/or antibiotic susceptibility of the microorganisms found. Analysis to establish microorganism identity and/or susceptibility is usually accomplished by subjecting individual colonies to differentiating media.

In some instances, accurate quantitation as well as identification of particular microorganisms, rather than mere determination whether that particular microorganism is or is not present is highly important. Thus a determination that a specimen is "positive" for microorganisms or "negative" for microorganisms may be insufficient. Rather if the specimen is positive, it may be necessary to know how many microorganisms of a particular species are present in the specimen. It is normal for certain microorganisms to be present in the human mouth and throat at all times, for example. These normal microorganisms, referred to as normal flora, do not generally cause disease in the numbers normally present. However, it is possible for an organism that may be part of the normal flora to proliferate to such an extent that it becomes a disease-causing organism (pathogen). It can be discerned, therefore, that the difference between the normal state of a human throat, for example, and a diseased human throat may be not in the identity of a particular organism that may survive to the time of analysis, but in the numbers of that organism present in the patient's throat. Generally, the bloodstream is sterile. However, transient bacteremia may occur where a few organisms enter the bloodstream through a cut or sore, for example, which is not usually a cause for alarm. Quantitation of microbes in a blood specimen is highly important to distinguish transient bacteremia from septicemia and, perhaps, specimen contamination. While quantitation is of utmost importance in analyzing blood specimens, determining the identity of the microbial pathogen present is also important. Although it may not be necessary to identify a microorganism taxonomically to treat a patient, it may be important to determine microorganism susceptibility to antibiotics so that proper drug therapy may be chosen. This may be done by identifying the organism by genus and species since drug manufacturers often have pre-determined the effectiveness of a drug on particular taxomonic groups. Alternately, testing for drug effect (antibiotic susceptibility) may be accomplished.

In some fluids, microorganism concentration may be so low in the specimen that using conventional methods a tested portion will not reveal microbial presence.

Recently, improvements useful for detecting low concentrations of microorganisms have been disclosed which have greatly improved detection of septicemia in blood before microorganisms have proliferated to such an extent that the patient is in a severe disease state.

Recently developed method and apparatus for concentrating and detecting microorganisms from a sample fluid are disclosed in U.S. Pat. No. 4,131,512 entitled "Method of Detecting Microbial Pathogens Employing a Cushioning Agent" and its division, U.S. Pat. No. 4,212,948 entitled "Apparatus For Detecting Microbia Pathogens Employing A Cushioning Agent". The technique disclosed in the above patents involves (when analyzing a blood sample) pre-lysis of corpuscular compounds followed by centrifugation to concentrate the microorganisms away from the other constituents including antimicrobial factors present in the blood. The concentrated microorganisms are then placed upon a nutrient media such that substances inhibitory to microbial growth present in the sample is diluted a minimum of sixty-fold. It has been previously documented that this technique yielded more positive cultures than the conventional liquid broth culture, the pour plate method, or the filtration method using the solid matrix filter. Gordon Dorn, Geoffrey A. Land, and George E. Wilson, "Improved Blood Culture Technique Based on Centrifugation: Clinical Evaluation," 9 *J. Clinical Microbiology* 391–396 (1979).

A problem remains in the field of microbial analysis despite the increasing sophistication in techniques for detecting and determining the identity of microorganisms within a specimen because the accuracy of the techniques is limited by the microbial integrity of the sample analyzed. By "microbial integrity" it is meant that a specimen taken at one point in time ($t_O$) and analyzed at another point in time ($t_l$) will provide an accurate representation of the microbial population of interest in the patient, food supply or other source from which the specimen was taken, when the specimen is analyzed.

At least three major factors exist which contribute to the lack of microbial integrity of specimens at $t_l$. The first is that specimens often contain antimicrobial factors which may kill microorganisms of interest before $t_l$. A second factor is microorganisms of interest may not survive in the specimen until $t_l$ even if no antimicrobial factors are present. Third, certain microorganisms may reproduce much more rapidly in a specimen than, for example, in the patient from whom the specimen was taken. Fast-growing but relatively harmless or irrelevant microorganisms may overwhelm the specimen so that more harmful species of interest are not detected by the analyzing laboratory. Failure to detect the important organism causes misinterpretation of the contamination problem even though the laboratory may correctly identify the organisms that have proliferated. In each case, the sample analyzed at $t_l$ will not give an accurate picture of the microbial problem in the patient or other source. Since drug therapy prescribed by a physician may be dependent on laboratory determinations of type of infecting microorganisms and degree of infection, solving the problem of microbial integrity may be vital to the recovery of the patient. False negatives with respect to food processing equipment or food itself may be detrimental to public health. In addition, misidentification of contamination in the food-related area may prevent discovering the source of contamination or cause the needless disposal of products. Discovering the source is often necessary to prevent future incidents of contamination.

Where antimicrobial factors, such as antibiotic drugs, are present in a specimen several problems arise. For example, a patient given antibiotics by his or her physician may have a level of such drugs in the blood or urine. At $t_O$, when a urine specimen is taken (for example), the urine may contain living microorganisms and some antibiotic. The antibiotic may continue to work to kill the microorganisms in the specimen so that at $t_l$, no living microorganisms remain. The laboratory may test the urine specimen and conclude that the patient no longer has a microbial problem However, this may be inaccurate. Unlike the specimen, the patient's system may continue to be seeded with microorganisms from the source of infection. While the level of antibiotics in the specimen might be sufficient to kill microorganisms therein, this does not necessarily reflect the status of the infection within the patient. Additionally, living organisms are required for identification and antibiotic susceptibility testing of microorganisms. If the specimen arriving at the laboratory has no living microorganisms, the laboratory cannot usually accurately identify the organisms nor determine antibiotic susceptibility. Drugs which may be more effective in eliminating particular organisms may not be prescribed if a less effective drug is taken by a patient and is effective enough to destroy the microbial integrity of the specimen taken from that patient, even though it is not effective enough in the patient's system to destroy the infecting microorganisms Natural bacteriocidal substances found in some specimens, such as blood, may also change the microbial integrity of the specimen before it is analyzed causing inaccurate results.

Even if no antimicrobial factors are present in a specimen, a microbial integrity problem remains If living microorganisms are contained in a specimen at $t_O$, but fail to survive to $t_l$, no microorganisms will likely be detected by the laboratory because detection techniques are chiefly based on microorganism reproduction. Such a situation will lead to false negative reports and potentially harmful consequences if microbial infections or contaminations go untreated.

Organisms may reproduce so well in a specimen that laboratory analysis will falsely indicate that the patient, foodstuff, or food processing equipment is highly contaminated. Incorrect drug therapy may be administered that is both unnecessary and potentially harmful by itself to some patients. Also, the rapidly-reproducing organism may cause other more harmful microorganisms in the specimen to die in the specimen, although they may be reproducing rapidly in the patient. Since appropriate drug therapy may differ depending on the identity of the problem organism, the patient may not be treated properly for eliminating the more virulent, undetected microorganism and will thus be harmed. In the case of food analysis, misidentification of the source of contamination may result and thus the source which introduced the virulent microorganism may not be discovered.

The problem of lack of microbia integrity in specimens may be increased because of hospital inefficiency in transporting the specimen to the laboratory and backlogs occurring in the laboratory of samples to be analyzed Although most textbooks and handbooks of microbiological technique mandate a specimen hold time of less than two hours, it is often impractical to comply with this standard of efficiency. The problem may be even worse when the specimen must be transported from a remote site such as a doctor's office, a food processing plant, or a sewage-treatment plant to a central laboratory. The accuracy of analysis decreases the longer it takes to transport the specimen to the laboratory because of the deterioration of microbial integrity of the specimen.

Thus, ideally, when testing fluids for differing levels of organisms, the level of organisms present in the sample should not change between the time a sample is taken, and the time the sample is tested. However, the environment of a test sample is usually different from the environment of the tested fluid due to varying temperature, light, availability of nutrients, etc. This can cause large differences in the number of organisms present at the time of testing. For example, the number of live bacteria in a urine sample which has been out of the donor's body for a few hours can increase due to reproduction, or they can decrease due to the action of antibiotics which the donor may be taking. Likewise, organisms present in water can quickly consume all available nutrients in a sample container and die before a test can be conducted. In any case, the longer the time between taking the sample and testing the sample, the higher probability of an incorrect test result there will be.

While the specimen quality problem has been addressed by the art, no known approach has been entirely effective and some have introduced further problems.

The simplest approach disclosed by the prior art is rapid transfer from the point of specimen collection to the point of analysis. For organisms particularly sensitive to transport, immediate streaking on nutrient plates has been suggested literally at the bedside of the patient. As pointed out, it is often difficult to make sure that a specimen has been transported within a recommended time frame. Even if it has, if the specimen contains antibiotics, up to 50% of the microorganisms of interest may be killed within 15-20 minutes. Thus, it can be seen that transport to a lab in two hours or less may be insufficient. Immediate streaking at bedside may cause loss of aseptic technique and the remaining problem of transport of the plate to the laboratory. Antibiotic presence may still present a problem.

The transport of specimens in the past has often been undertaken in initially sterile containers in an attempt to improve specimen quality. Even if a specimen is collected in a sterile container, however, the microbial integrity of the specimen may deteriorate during transport because initial container sterility neither prevents death nor overgrowth of microbes in the specimen. Additionally, sterility of containers could be lost where such specimens as urine, for example, are collected as soon as the closure means is removed for micturition.

In U.S. Pat. No. 4,145,304 ('304) and U.S. Pat. No. 4,174,277 ('277), a method and structures for the removal of antimicrobial factors were disclosed. A mixed resin bed adsorbs the antibiotics to prevent cidal effects on the microorganisms of interest. Multiple physical entries into the specimen are required in the resin bed system in that the specimen must be collected from the patient, transferred to the resin bed for adsorption of antibiotics, and removed from the resin bed. The more physical entries a specimen is subjected to, the higher the risk of microbial contamination from the skin of the operator or the environment. The resin bed is insoluble and therefore requires physical manipulations before the specimen may be analyzed. Loss of microorganisms may result from some non-selective adsorption. Additionally, the mixed resin system fails to address the maintenance of microbial cells in a viable condition without replication.

Certain systems are taught for use in urine specimens which address the problem of uncontrolled growth of particular species of interest which could skew analysis. However, most of these systems focus on killing bacteria that may be present since the specimen will be assayed for general chemical levels, such as glucose, bilirubin etc. In systems taught for preserving microbial integrity, antibiotic blockage is generally not addressed. Thus, no means of preserving the actual count of microorganisms in the presence or absence of bactericidal agents is addressed by known urine specimen-treating agents.

Maintaining a specimen at about 4° C. from the time of collection to the time of analysis is another known approach to attempting to maintain specimen quality Since low temperature may slow microbial growth, antibiotics which act on only replicating organisms may lose effectiveness. However, this approach is impractical in the field, and the low temperature may detrimentally affect the viability of certain microorganisms while being an ineffective control on the growth of others. Additionally, the action of antibiotics is not necessarily controlled by the low-temperature approach. An example of a microorganism which may be killed by the cold is *Streptococcus pneumoniae*, one that a physician would be interested in detecting as it is an etiological agent of lobar pneumonia disease. Thus, it is preferable to maintain the sample at room temperature of about 21-25° C.

Other methods for improving specimen quality include Amies (C. Amies and F. Path, 58 *Canadian J. Public Health* 296 (1967)) and Stuarts (R. Stuart et. al., "The Problem of Transport of Specimens For Culture of Gonococci," 45 *Canadian J. Public Health* 73 (1954)). These methods may provide some improvement of specimen quality for some microorganisms of interest, however these systems fail to address the possible presence of antibiotics in a specimen, the differing nutritional needs of different microorganisms, and the effect of specimen hold time on accurate microorganism quantitation.

Another problem left unaddressed by previous approaches to microbial detection is the possibility that additional microorganisms will be introduced to a specimen from an external source. This "contamination" of the specimen will cause inaccurate results since, for example, a patient may be deemed to have a microorganism in the blood that in fact is not present. Contamination of specimens becomes more likely the more the specimen is transferred from container to container and the more it undergoes physical manipulations. For example, a commercially available system for urine specimen transport (Becton-Dickenson) requires manipulation from the urine collection vessel to the container with the preservative therein. It is therefore desirable to provide collection vessels which reduce the manipulations required, provide a means to instantly preserve the microbial integrity of a sample, and in a most preferred embodiment can be utilized for other processing steps in the analysis of microorganisms of interest.

Therefore, a method and means is needed for receiving a fluid sample suspected of containing microbial pathogens and antimicrobial factors which will minimize the risk of contamination, reduce or eliminate the requirement of sterility of the collection vessel for some specimens, provide for deactivation of antimicrobial factors during the time that the sample is transported so that once the sample is removed from the collection and/or processing vessel and placed on growth media, the microorganisms of interest present in the sample including the fastidious microorganisms of interest will proliferate and become identifiable, and which will maintain the viability of at least some of the microorganisms of interest, preferably so that the microbial integrity of the sample is maintained from time of specimen collection ($t_O$) to the time of specimen analysis ($t_l$).

It has now been found that microbial integrity of patient specimens and other specimens may be preserved so that analysis at a $t_l$ up to about 72 hours after $t_O$ will result in a much more accurate representation of the microbial population in that sample than has previously been possible. This has been done by providing an admixture of individual chemicals which solubilize in an aqueous specimen to form a unique mixture which acts synergistically as a preservative of microbial integrity of the specimen. By "preservative" it is meant that the unique mixture prevents replication of microorganisms of interest, allows improved survival of said microorganisms until the inception of laboratory analysis, and blocks the action of antimicrobial factors that may be present in the specimen. By "microorganisms of interest" it is meant the microorganisms to be tested for in the laboratory protocol. It may not be necessary or desirable to preserve the viability, for example, of every possible microorganism that may be present in a given specimen. In the food industry, for example, non-harmful or even beneficial microorganisms may be present in food which a laboratory would not be interested in identifying. However, the laboratory would be interested in testing for microorganisms potentially harmful to human health. Therefore, preservation of the latter "microorganisms of interest" would be addressed by the present invention. In addition, the growth of the microorganisms which are not of interest must be kept in check to prevent masking of the harmful microorganism in the analysis procedure, and to prevent the rapidly producing non-harmful organisms from depleting the nutrients and causing death of other microbes. The present invention is effective in inhibiting replication of such potentially interfering organisms. The present invention thus allows a longer time to elapse between specimen collection and specimen analysis than has previously been possible without sacrificing accuracy. It also allows for more accurate analysis even if a sample is analyzed within a short time period because it blocks the action of antimicrobial factors which may destroy microorganisms of interest even within the two hour processing time period recommended in the prior art.

In addition, no reason is known why the disclosed specimen transport system would not be advantageous for improving the accuracy of analysis of specimens for periods exceeding 72 hours. If the viability of even a few microorganisms of interest is maintained, the microbial integrity of specimen analyzed will be improved over that possible according to the prior art, resulting in improved laboratory analysis.

Disclosed is a novel method, article and compositions for detecting microbial pathogens. In another aspect, this invention relates to a novel technique and means for selectively separating microorganisms from a sample fluid which contain antimicrobial factors. In still another aspect, this invention relates to a method and means for use in the detection of microbial pathogens which provides improved recovery of microorganisms. In yet another aspect, this invention relates to a method and means for accurately quantitating the number of microorganisms present in a sample fluid at a given time when quantitated at a later time.

An article for receiving specimens is disclosed which includes a means for preserving the microbial integrity of the specimen.

SUMMARY OF THE INVENTION

According to the invention, there is provided an apparatus for stabilizing the level of microorganisms in a sample comprising a container and a composition effective for preserving the microbial integrity of the specimen. The composition is located in the container whose structure provides for admixing of the specimen and the composition as the specimen enters the container.

Also according to the invention, there is provided a method for collection and transportation of fluid specimens comprising the admixing of a composition effective for preserving the microbial integrity of the specimen with the specimen in a container; the container's structure providing for the admixing of the specimen and the composition as the specimen enters the container.

Further, in accordance with the invention, compositions and methods for deactivating antimicrobial factors and maintaining the microbial integrity within a specimen after it has been collected and before the microorganisms of interest are analyzed are also disclosed.

According to a preferred embodiment of the invention, admixing of the composition and specimen takes place in a container comprising a screw on cap (thereby reducing the chances of contamination of the test personnel or the specimen when the cap is removed and replaced as may occur when a rubber stopper is used), a slidable piston within the container, and a detachable piston rod wherein the rod may be removed from the piston (leaving no portion of the rod outside of the container and allowing the container to be placed in a test tube rack, stood on a table, or mounted in a centrifugation device).

Also, according to a preferred embodiment of the subject invention, a particular class of compositions, effective for preserving the microbal integrity of the specimen, (hereafter, the specimen transport system) soluble in aqueous solution effective for deactivating antimicrobial factors within a specimen containing said antimicrobial factors and microorganisms and method of use thereof, is provided which serves the following purposes:

(1) immediate blockage of the cidal action of penicillins, cephalosporins, and aminoglycosides, and antibiotics which require microbial growth for effectiveness;

(2) initiation of anaerobic conditions to allow maintenance of the life of fastidious organisms susceptible to the lethal action of oxygen;

(3) complete neutralization of the cidal action of normal human blood and cidal components inherent in other specimens;

(4) to hold stable the viable count of microorganisms over a period of time; and (5) provide for the optimal nutritional needs of the microorganisms of interest.

The procedure can be utilized on all types of body fluids such as blood, bone marrow, spinal and plural fluids, body secretions, urine and the like as well as non-fluid specimens from a patient from which microorganisms may be extracted in aqueous solution. The microbial integrity of water supply specimens, food specimens and samples of surface contamination of food preparation or processing equipment and other specimens are also appropriately preserved with the present invention. Generally, when employed in connection with a blood sample, a lysing agent will be employed A mucolytic agent may be advantageously employed with sputum. An example of an effective lysing or mucolytic agent is detoxified saponin which is disclosed in U.S. Pat. No. 4,053,363 to Dorn, et al. The novel composition of the subject invention can be utilized in a sample collection or transporting container and allowed to be admixed with the sample after it has been collected but before microbial pathogens therein are analyzed by a method such as, for example, depositing them upon a growth media for microbial pathogens. The novel composition of the subject invention can be in the form of an aqueous solution contained within said sample collection and transporting container. However, the novel composition for specimen transport is preferably positioned in said container in the form of solid particles which are soluble in the sample fluid or the aqueous extract of the specimen as the case may be.

It is envisioned that the subject invention can be utilized within the lysis-centrifugation devices such as disclosed in U.S. Pat. No. 4,212,948 issued Jul. 15, 1980 and entitled "Apparatus For Detecting Microbial Pathogens Employing A Cushioning Agent", which employs r the basic method disclosed in U.S. Pat. No. 4,131,512 issued Dec. 26, 1978 entitled "Method For Detecting Microbial Pathogens Employing A Cushioning Agent". Also, in accordance with one embodiment of the subject invention, a novel method of assembling and sterilizing a lysis-centrifugation device is provided which includes:

(a) depositing a liquid cushioning agent such as disclosed in said '948 patent, and a specimen transport system in the form of solid particles within a lysis-centrifugation tube;

(b) creating a vacuum in said tube and heating said tube to the vaporization temperature of said liquid cushioning agent, e.g., about 120° C. for a sufficient time, e.g., about 30 minutes to sterilize the interior of said tube and thereafter cooling said tube to room temperature.

In addition, the system of the subject invention can be utilized in practicing the lysis-centrifugation technique as disclosed in U.S. Pat. No. 4,164,449 issued Aug. 14, 1979 and entitled "Surface Separation Technique For The Detection Of Microbial Pathogens". As an example, a specimen might be held in a container such as the lysis-centrifugation tube described above while the tube is being held for processing.

Surprisingly the novel system of the subject invention will inhibit replication of microorganisms which are contained within the specimen for a period of time up to about 72 hours after specimen collection. It is believed that replication may be inhibited for even longer periods when the subject invention is utilized, depending on the identity of the microorganisms.

The specimen transport system of the subject invention contains extremely high concentrations of specific chemical compounds which serve to neutralize antibiotics and/or normal human serum factors. These elevated concentrations cannot readily be incorporated in conventional broth systems currently used by many laboratories to test for microorganisms because the high concentrations of chemicals required would prove inhibitory to many potentially pathogenic organisms. However, where the specimen of interest has a high concentration of microorganisms, such as a urine specimen, the invention may be usable in conjunction with a conventional broth system, wherein the transport vessel contains the specimen and the composition of instant invention, this being diluted into the broth system when analysis is initiated. The specimen transport composition of the subject invention will effectively deactivate most antibiotics and other antimicrobial factors where a sample fluid is mixed therewith and will stabilize the viability of microorganisms of interest.

It is usually necessary that the resulting admixture of specimen and the disclosed composition be diluted on growth media at the time analysis is initiated in order that the concentrations of the deactivating chemicals be reduced to a concentration noninhibitory to microorganisms of interest. Thus, the invention is particularly useful and advantageously employed in a method in which dilution is necessary prior to microbial analysis. For example, swabs, sputums, urines, blood processed by and the lysis-centrifugation systems disclosed in U.S. Pat. Nos. 4,164,449; 4,131,512; and 4,221,948 described above generally require a high dilution factor and therefore are suitably preserved by the present invention.

As an illustration of the benefits of the instant invention, the lysis-centrifugation system as described above is an appropriate example. If the specimen transport system is included within the centrifugation tube for treating the blood sample prior to centrifugation and deposit of the concentrated microorganisms on the media, the microorganisms of interest will be protected from attack by anti-microbial factors which are present in the liquid sample such as antibiotics and serum factors which are cidal in nature. In contrast, without the instant invention, microbial pathogens may be destroyed within the centrifugation tube prior to processing resulting in undesirable false negative analysis results of cultures or inaccurate quantitation. The basic benefit of use of the subject invention can be more graphically illustrated by the following theory. Septicemia, microorganisms in the bloodstream with clinical signs of shock, disseminated intravascular coagulation (clotting) and elevated temperature (fever), hypotension, etc., does not imply that the blood-stream itself is infected. In this theoretical model, there is primary infection elsewhere such as the kidneys, a lung, or the like, and the micro-organisms are being seeded at a given rate into the bloodstream. The immune system and/or antibiotics are eliminating the microorganisms at a fixed rate. A patient survives a septic crisis if and only if the seeding rate is less than the rate of clearance. Thus, based upon this theoretical model, conventional blood culture systems will yield a significant number of false negative cultures because once the specimen is drawn, microbial seeding from the primary source ceases to the specimen, but the antimicrobial factors present in the patient's blood are still active. Hence, during transport to a laboratory for processing, these factors may kill the viable organisms that were present at the time of draw, and therefore, render the test negative. This concept becomes especially important for immunologically competent patients and those who are on a broad spectrum of antibiotics. Thus, the practice of the improvement of the subject invention in conjunction with the lysis-centrifugation system is to literally preserve the microbial status of the blood sample by instantly blocking the known deleterious action of the immune system and bactericidal antibiotics prior to dilution of these factors on agar plates which is an inherent feature in the lysis-centrifugation method.

The employment of the specimen transport system in urine analysis will involve the presence of the specimen transport system in the micturition receptacle from which a clinically appropriate aliquot of urine may be removed for direct microbial analysis. Thus, the practice of the subject invention is to literally preserve the microbial status of the urine sample by instantly blocking the known deleterious action of bactericidal antibiotics and by acting as a bacteriostatic agent even in the absence of antimicrobial agents.

The employment of the instant invention with throat culture swabs, vaginal swabs, tissue, bone-marrow and other specimens similarly advantageously preserves the microbial integrity of the specimen.

BRIEF DESCRIPTION OF DRAWINGS

This invention can be more easily understood from the study of the drawings in which:

FIG. 1 is cross-sectional view of a centrifugation article which can be used to practice the subject invention;

FIGS. 2-9 depict steps of a method for detecting microbial pathogens which can employ the subject invention.

DETAILED DESCRIPTION OF PREFERRED EMBODIMENTS

Initially, it should be noted that as used herein, the unit designation "ug" signifies micrograms.

Although not the only use for the invention, by way of explanation, embodiments of the invention will be described as they would typically be used in collecting, preserving, and transporting urine or blood samples.

Figure 17:
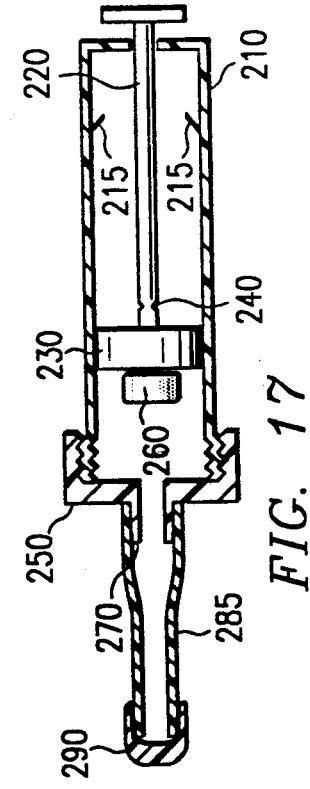
FIG. 17 is a cross section of one embodiment for collecting and transporting samples.
Figure 23:
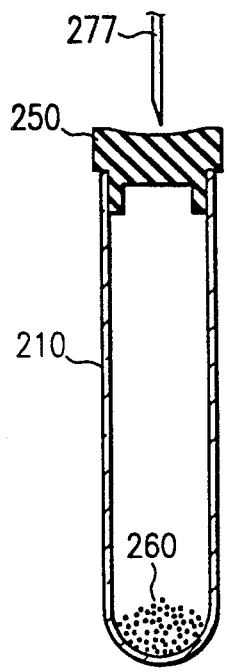
FIG. 23 is a cross section of another embodiment for collecting and transporting samples showing the specimen transport system in a powder state.

Referring to FIG. 17, an embodiment of the invention may be described as an apparatus similar in shape to a typical hospital syringe having a container 210, a piston 230, and a shaft 220. Closure member 250 may take the form of a screw on cap (FIGS. 17, 18, 19, and 21), or a puncturable stopper (FIG. 23). An advantage of twisting the cap on, rather than using a stopper, is that a twisted or screwed cap does not have to be popped off. This reduces the chance of contamination of the testing personnel or the sample, or creating aerosols and other potential hazards in the air. When closure member 250 does take the form of a cap, it has a sealable aperture 270 contained therein.

Composition 260 is a composition, effective for preserving the microbial integrity of the specimen, and may be designed to retard the increase or decrease in the number of organisms present in the sampled fluid. Composition 260 may be in any state such as a tablet, a powder, or a liquid; and a preferred composition, called a specimen transport system herein, is described in more detail below.

Figure 21:
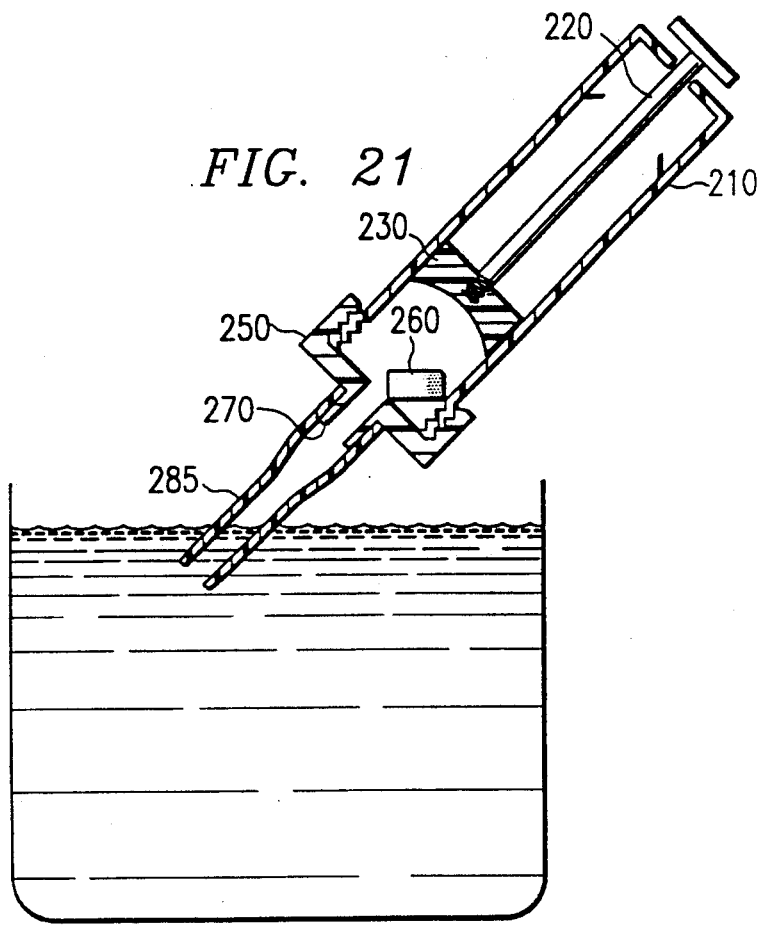
FIG. 21 is a cross section of the embodiment of FIG. 17 as it might be used in drawing a fluid sample from a sample reservoir.

Referring to FIG. 21, when taking a urine sample, a tube 285 is placed over aperture 270 and inserted into specimen cup 282 which contains the urine to be sampled. Shaft 220 is drawn back, bringing piston 230 along and pulling urine into the cylinder. Composition 260 dissolves into the urine in the cylinder. Once a sufficient sample has been drawn, tube 285 may be removed and dropped into the specimen cup, thereby lessening the chance that urine from tube 285 will contact any people. Next, cap 290 may be placed over aperture 270 to close container 210 (FIG. 18).

Figure 20:
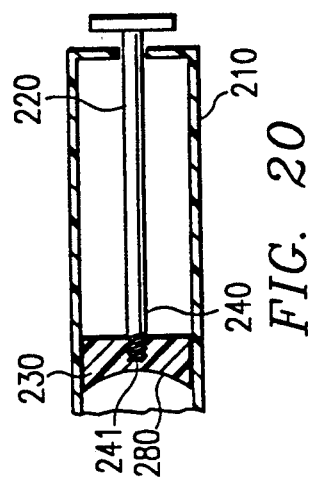
FIG. 20 is a cross section of an embodiment for collecting and transporting samples showing an alternative piston surface and shaft detachment.
Figure 18:
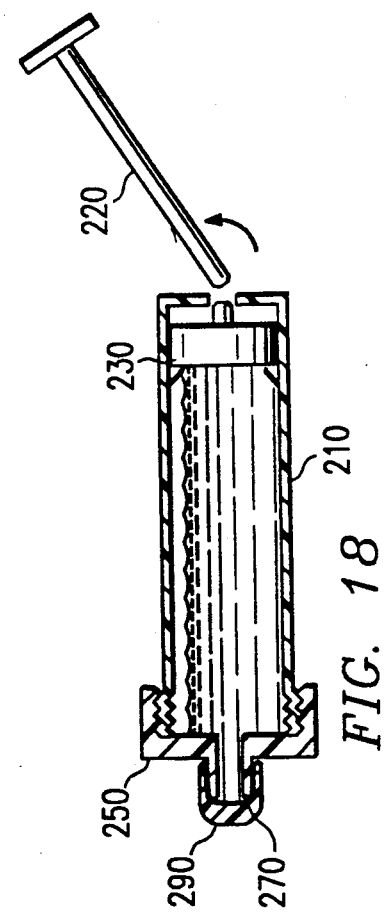
FIG. 18 is a cross section of an embodiment of FIG. 17 after a sample has been drawn.
Figure 22:
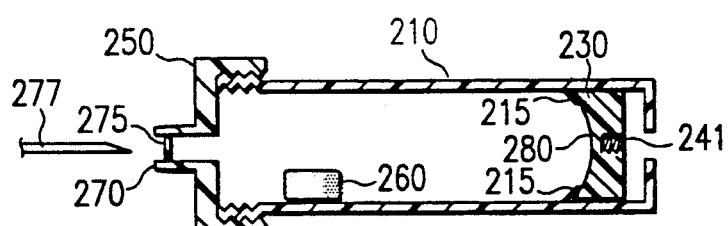
FIG. 22 is a cross section of another embodiment for collecting and transporting samples as it might be used as a vacuum draw sampler.

In FIGS. 17, 18 and 21, a means for removing shaft 220 is shown in the form of a narrow portion 240 of shaft 220, and as shown in FIG. 18, it allows the sample taker to break shaft 220 inside container 210. The remover means allows the entire apparatus to stand on a table or be placed in a rack. In FIG. 20 and FIG. 22 the shaft remover takes the form of a threaded connection 241 between piston 230 and shaft 220. Removal of shaft 220 allows the apparatus to be used in applications normally requiring test tubes or other containers which may be stood in a rack or used in a centrifugation device.

Figure 19:
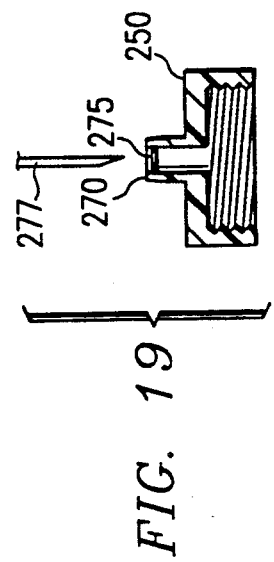
FIG. 19 is a cross section of an embodiment of the invention incorporating a puncturable closure member, useful with the embodiment of FIG. 17.
Figure 24:
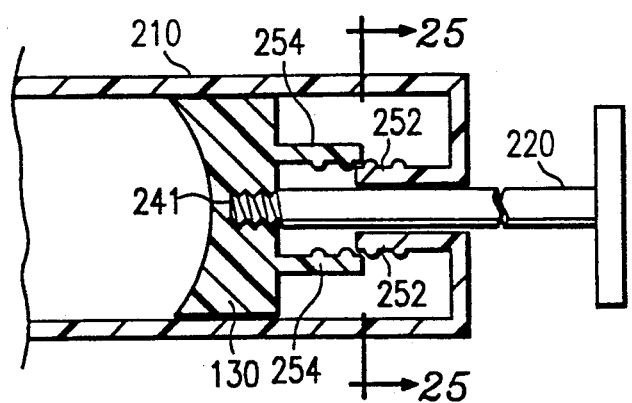
FIG. 24 is a cross section of the embodiment of FIG. 20 showing an alternative locking method.
Figure 25:
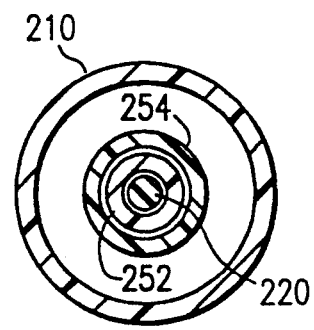
FIG. 25 is a cross section through line A—A in FIG. 24.

Now referring to FIG. 19 and FIG. 22, an embodiment for blood sampling is shown. Puncturable membrane 100 may be provided for sealing aperture 270. Piston 230 is drawn back, thus creating a low pressure area in the cylinder. A lock 215 may be provided which anchors piston 230 and preserve the low pressure area. Once piston 230 is in place, shaft 220 may be removed and discarded Lock 215 may also take the form of snapping members 252 and 254 as shown in FIGS. 24 and 25.

Again referring to FIG. 22, needle 277 is connected to a fluid source to be sampled. Examples of sources would include an intravenous connection to a patient's vein or artery, a traditional syringe which has drawn a sample, or a tube extending into a specimen cup containing fluid. Needle 277 may puncture membrane 275, and fluid will be drawn into the cylinder by the low pressure. Needle 277 may then be removed, and membrane 275 will again seal. Cap 290 may then be placed over aperture 270 for protection of the membrane. Composition 260 dissolves into the fluid, and the specimen may be transported to the lab for tests. Once in the lab, concave surface 280 allows the specimen to be centrifuged in the apparatus.

Now referring to FIG. 23, an embodiment for taking samples through a needle 277 is shown wherein closure member 250 takes the form of a pliable stopper, the composition 260 is in a powder state, and container 210 is made from glass. The pressure in container 210 is lower than the outside pressure. Needle 277 punctures pliable stopper 250, fluid enters container 210, and mixes with composition 260. Needle 277 is then withdrawn, and pliable stopper 250 seals the puncture. The device may then be taken to a lab for testing.

Choice of material for the container is not critical; for example, glass or plastic may be used. Glass holds a better vacuum than plastic, but plastic does not break as easily. Other containers which may be used include: general syringes, special purpose syringes such as described in U.S. Pat. No. 4,459,997 to Sarstedt, and glass vacuum tubes adapted to be punctured by a needle through a pliable stopper.

In embodiments using a powder or liquid state composition, a one way valve may be used to prevent the composition (or fluid which has come in contact with the composition) from flowing out of the aperture In the case of a powder, a screen may be used to keep the powder in the cylinder, while still allowing the fluid to pass into the container.

DETAILED DESCRIPTION OF THE SPECIMEN TRANSPORT SYSTEM

In a preferred embodiment of the invention, the composition effective for preserving the microbial integrity of the specimen comprises the novel specimen transport system of the subject invention, including specific chemical agents at relatively high concentrations which will deactivate antimicrobial factors such as antibiotics and the cidal agents within a specimen such as normal human blood, among others. The specimen suspected of containing microorganisms of interest may be a fluid such as blood or urine or a semi-solid or solid from which microorganisms are collected and suspended in an aqueous solution. This may be done, for example, by wiping a sterile swab against a solid surface of interest, retaining the swab and placing the swab in a suitable solution effective to sustain viability of microorganisms of interest. As another example, muscle tissue may be transported to the laboratory for later analysis for microorganisms of interest by taking a portion of said tissue and placing it in a aqueous receiving solution which will allow permeation and diffusion into the tissue to preserve any microorganisms in said tissue. Effective nutrients to sustain viability of microorganisms of interest are to be present in the transporting media. "Effective nutrients" to be added to a specimen may be anything from sterile, distilled, deionized water to a complete commercially available broth for microorganism growth depending on the nature of the specimen and the identity of the microorganism of interest. The criteria for being "effective" is the ability to sustain the viability of the microorganism of interest from the time of specimen collection ($t_O$) to initiation of specimen analysis ($t_I$) sufficiently, in the presence of the bacteriostatic agents added as a part of the specimen transport system of the present invention, so at least some of the microorganisms of interest alive in the specimen at $t_O$ will be able to replicate at $t_I$. In the majority of instances, the survival of microorganisms from $t_O$ to $t_I$ will be at least 50% and often over 80% with the use of the present invention. However, advantages are provided by the instant invention over the art even if survival rate is not high since the survival of microbial species to tl is improved by this invention, leading to better identification and antibiotic susceptibility testing than ever before possible.

In some cases, the effective amount of nutrients will be only pure water, for example where the specimen is not inherently aqueous. What will comprise an effective amount of nutrients to be added depends not only on the nature of the specimen but the identity of the microorganism of interest. In addition a proper balance must be achieved between supplying nutrients effective for microbial replication and preventing the replication of the microbes during specimen transport with bacterio-static agents. Different microorganisms have different nutritional needs. The nutrients supplied in connection with the instant invention should allow the microorganisms of interest to survive until $t_I$, so that when the specimen is diluted upon growth media (such as an agar plate) so that the factors in the instant invention inhibitory of replication of said microorganisms of interest are no longer effective, the surviving microorganisms of interest will be able to replicate so that testing and identification may proceed.

For example, neither blood nor urine will generally require addition of nutrients to accomplish the results described above as each inherently contains sufficient nutrients which microorganisms of general interest need over transport time periods. However, when microorganisms of interest have been collected by means of a tool to which microorganisms become attached, such as for example a swab, effective nutritional components must be supplied in conjunction with the bacteriocidal agents. A swab is commonly used to collect specimens from patient's throats, for example. In addition, it may be desirable for certain microorganisms of interest to add nutrients even to specimens such as blood and urine to prolong viability. Specific examples below indicate the use of effective nutrients in the specimen transport system of the instant invention.

A growth base effective for supporting general nutritional needs of microorganisms of interest without inhibiting them is desirably added if the specimen itself does not inherently contain this effective nutrition. One effective growth base is Mueller-Hinton Broth (available from BBL Microbiology Systems, Cockeysville, Md 21030). This consists of Beef extract (3 g/l) Acid Hydrolysate of Casein (7.5 g/l) and starch (1.5 g/l). Another effective growth base is Tryptic Soy Broth (available from BBL Microbiology, Cockeysville, MD 21030). The composition of the growth base chosen should be noted so that if such growth base contains a portion of effective nutrients that would otherwise be added separately, the amounts will be adjusted so that the total concentration of the particular nutrient will be known. For example, it may be desirable to add starch to the nutrient medium especially if Haemophilis is an organism of interest. Mueller-Hinton Broth contains starch, so the amount added will take the Mueller-Hinton contribution into account.

In the specimen transport system of the instant invention, a combination of effective nutrients and replication inhibitors is achieved which provides nutrients to microorganisms of interest, yet inhibits replication of all microorganisms in the specimen to preserve the microbial integrity of the specimen. In combination with appropriate replication inhibitors, it has been found that about 0 to about 10% (w/v of growth base per total volume of specimen plus transport system) is effective where it is necessary to add nutrients. A preferred range is 0.1% to 5.0%. Even more preferred is from about 1% to about 3%.

Starch is preferably employed in connection with throat cultures, where Haemophilis is a microorganism of interest, since starch appears to aid Haemophilis survival, however starch is not considered necessary for all specimens or microorganisms of interest. When starch is desirable, it has been found effective from about 0.005% to about 2.0% (w/v of growth base per total volume of specimen plus transport system). More preferred is 0.01% a range from about to about 1.5%. Most preferred is a range from about 0.1% to about 1.0%.

Agar is also a desirable, but not necessary, nutrient. It provides a surface for growth and keeps microorganisms dispersed in a fluid medium. The range of agar employable is from about 0 to about 5% (weight per volume of specimen and specimen transport system total), preferably 0.5% to about 2% and most preferably 0.1% to 1.0%.

The effective nutrients for a specimen suspected to contain *Haemophilis* includes hemoglobin. Hemoglobin also improves *Streptococcus pneumoniae* and so is desirable when this is the organism is of interest. Surprisingly, when hemoglobin is utilized for the transport system of the instant invention, no source of NADP (nicotinamide adenine dinucleotide phosphate) need be added to support Haemophilis. It is known that some Haemophilis strains require a so-called "x" factor and a so-called "v" factor (NADP). Hemoglobin supplies the "x" factor, but the need for adding an exogenous source of NADP is not evident when the instant invention admixture is employed.

Deactivation of antimicrobial factors is also part of the function of the instant invention. For example, in accordance with one embodiment of the invention, blocking agents for aminoglycoside antibiotics and polymyxin B are included within the specimen transport system. Typical aminoglycoside antibiotics include gentamicin, tobramycin and amikacin. The aminoglycosides and polymyxin B all have net positive charges. When this charge is blocked, these compounds lose their potency. Therefore, in accordance with one embodiment of this invention, a blocker for this positive charge is included within the specimen transport system. A preferred compound is sodium polyanetholsulfonate. The sodium polyanetholsulfonate will inhibit the action of aminoglycosides and polymyxin B in direct proportion to its concentration. Surprisingly, it has been found that the concentration needed to completely inhibit these antibiotics is a concentration of at least approximately 0.06% weight/volume of specimen of sodium polyanetholsulfonate, a concentration taught to be toxic by the prior art. Another such blocker compound is sodium amylosulfate. The specimen transport system of the subject invention contains sufficient sodium polyanetholsulfonate to result in between about 0.06% to about 6.0% and preferably from about 0.1% to about 2.0% (by weight of the SPS based upon the total weight of sample fluid and specimen transport system composition). Most preferably, SPS is added in the range of from about 0.3% to about 1.0% (by weight of SPS based upon the total weight of sample fluid and specimen transport system composition). The "toxic" effect of sodium polyanetholsulfonate to certain microorganisms has been eliminated in the instant invention by employing it in a method where subsequent dilution on growth media to an approximate final concentration of 0.03% or less (by weight sodium polyanetholsulfonate on the medium).

The concentration of SPS employed in the instant invention is one sufficient to block the action of aminoglycosides, streptomycin and polymyxin B, as previously discussed. SPS at high concentration is also effective in controlling the replication of some microorganisms from $t_0$ to $t_1$ and as a result, lowering the effectiveness of antibiotics which require microbial replication for activity. It is surprising that SPS can be used in a system involving the detection and identification of microorganisms since the prior art teaches that SPS is toxic to microorganisms at concentrations exceeding 0.03%. Such low concentrations of SPS as are taught to be nontoxic in the prior art would be ineffective in the instant system to accomplish the desired results.

The specimen transport system of the subject invention preferably contains a water-soluble component effective for blocking the action of penicillin and cephalosporins, and which in combination with other components of the specimen transport system will exert a bacteriostatic effect on the replication of microorganisms in the specimen without exerting a cidal effect on the microorganisms of interest. Sulfhydryl-containing compounds such as L-cysteine, N-acetyl-cysteine, thioglycolate, glutathione and mercaptoethanol are suitable antibiotic inhibitors for the penicillin and cephalosporin classes. However, it has now surprisingly been found that the concentrations used in the past are suboptimal to achieve the desired goal of antibiotic blockage, and that higher concentrations, taught to be toxic to microorganisms in the prior art, may be used in a method for preserving the microbial integrity of a specimen with the advantage of both blocking antibiotic action and acting as a bacteriostatic agent in combination with other specimen transport system components. Another effective antibiotic blocker that may be employed in the specimen transport system of the subject invention is an enzyme specific for the antibiotic. If utilized, enzyme is employed in conjunction with a sulfhydryl-containing compounds in the present invention as it has been found that the combination of enzyme with the other specimen transport system components exerts an effect not possible with enzyme alone.

It is preferred that the component effective for blocking the action of penicillins and cephalosporins be available in a dry form, such as a salt or a freeze-dried form so that it may be used in a dry admixture. However, liquid blocking components such as mercapto-ethanol may be utilized if desired in a liquid version of a specimen transport system, or as part of liquid specimen diluent supplied in conjunction with a dry admixture.

One or more sulfhydryl-containing compounds may be used in combination, particular combinations being preferred.

L-cysteine is the preferred inhibitor of penicillins and cephalosporins present in the specimen transport system in an amount to result in from about 8.2 uM to about 8.25 mM in the combined sample fluid and specimen transport system. The most preferred amount differs according to the specimen. With urine specimens, it is preferred to employ a range from about 0.82 mM to about 41.3 mM, most preferably 4.1 mM to 24.8 mM. With throat cultures and other specimens, the preferred range is from about 0.82 mM to about 24.8 mM and most preferably from about 0.82 mM to about 8.3 mM. In a particularly preferred embodiment, the specimen transport system of the subject invention contains a synergistic mixture of thioglycolate and cysteine with cysteine contained therein in an amount from about 8.2 uM to about 82.5 mM and thioglycolate contained therein in an amount from about 0 to about 42.5 mM (molar equivalents based on the molecular weight of thioglycolic acid as the active ingredient). This combination will deactivate the penicillins, cephalosporins and some aminoglycosides very effectively and also reduce the viscosity of the thus formed system and increase shelf life of the dry admixture Thioglycolate and similar compounds by themselves cause an undesirable increase in viscosity of the transported specimen. It has been found, however, that the above-described combination of cysteine and thioglycolate results in much lower viscosity after lysing of blood, for example. In addition, the combination allows proportions of thioglycolate that are less toxic to the fastidious microorganisms. Another advantage is that cysteine is easily oxidizable and the presence of thioglycolate helps maintain the cysteine in a reduced state in the course of preserving the microbial integrity of the specimen, for example, during the preparation of the lysis centrifugation tube and for shelf life stability of the specimen transport system admixture. An example of the combination of the cysteine and thioglycolate that can be used in a centrifugation tube as set forth in U.S. Pat. No. 4,212,948 includes an initial concentration of cysteine of 1.2% and thioglycolate of 0.1% by weight in the sample fluid and specimen transport system and once finally diluted on growth media as disclosed in said patent a final concentration of cysteine of about 0.018% and thioglycolate of about 0.002% by weight. It is noted that because of the propensity of the cysteine to oxidize, it is desirable to add the cysteine during the manufacture of a centrifugation tube during the last step prior to tube evacuation and autoclaving. The purity of the cysteine is important. Because of the high concentration of cysteine required in the specimen transport system, this compound should have a purity of greater than 95%. If one uses cysteine which is contaminated with cystine, the cystine will precipitate out during the processing of blood. Since, the cystine precipitate resembles small colonies of microorganisms on the agar plate, this is an undesirable property The inclusion of the thioglycolate and cysteine combination has a secondary effect in that it will protect anaerobic microorganisms, e.g., clostridial species, from being poisoned by the oxygen present in the blood specimen during transport of the specimen to the laboratory. This is due to the fact that the thioglycolate and other sulfhydryl compounds are excellent oxygen scavengers. Cysteine is much more effective than other sulfhydryl compounds in blocking the cidal action of penicillins, cephalosporins and some aminoglycosides on a gram or molar basis, and as mentioned, an additional benefit of the presence of the cysteine is that it will reduce the viscosity of lysed blood which improves the sedimentation of the microorganisms in a centrifugation tube. Preferably, the free base form of cysteine is utilized to prevent the necessity for addition of high concentrations of pH adjuster such as would be required with cysteine-HCl However, the latter may be used.

If it is desired to utilize another sulfhydryl compound rather than cysteine, and not in conjunction with cysteine, appropriate concentrations to achieve an effect to simulate cysteine's effect as closely as possible may be utilized.

Thioglycolate may be used in a blood specimen in the range of from about 4.4 mM to about 43.8 mM, preferably from about 8.8 mM to about 35.1 mM and most preferably from about 17.5 mM to about 30.7 mM.

Glutathione is effectively used in blood from about 1.63 mM to about 16.3 mM, preferably from about 3.25 mM to about 13.0 mM and most preferably from about 6.5 mM to about 11.4 mM.

For specimens other than blood, it is preferred to use higher amounts of thioglycolate or glutathione. Thioglycolate is effectively employed from about 4.4 mM to about 52.6 mM, preferably 8.76 to 43.8, and most preferably from about 17.5 mM to about 35.0. Glutathione is preferably employed from about 1.6 mM to about 19.5 mM, more preferably from about 3.25 mM to about 16.3 mM and most preferably 6.51 mM to about 13.0 mM.

In accordance with another embodiment of the subject invention, deactivators for sulfa compounds are present in the specimen transport system. It is believed that the sulfa compounds exert their antimicrobial action by interfering with the folic acid pathway of bacteria. This pathway is essential for the synthesis of the nucleic acids which are the primary compounds of microbial DNA. Accordingly, preferably para-aminobenzoic acid (PABA) may be added to the specimen transport system as a competitive inhibitor of sulfa compounds. The preferred concentration of PABA is in the range of from 5 micrograms per milliliter to about 500 micrograms per milliliter and the most preferred range is in the range of from about 10 micrograms per milliliter to about 100 micrograms per milliliter of the combined sample and specimen transport system. However, the inhibition of replication provided by the combination of the other specimen transport system components may make the addition of PABA necessary only in circumstances where very high sulfa compound concentrations are present or where it is desired to extend the hold time of specimens to the extent that the sulfa drugs begin to exert a cidal effect on the microorganisms of interest.

The specimen transport system of the subject invention can also contain enzymes which react with and deactivate certain antibiotics, for example, beta-lactamase, and penicillinase. Usually from about 1 to about 20 units of activity of such enzymes will be effective in the system to provide the blocking effect in combination with the other components of the specimen transport system. Example XV shows the synergism achieved with employment of enzyme with other specimen transport system components.

The specimen transport system of the subject invention can include other compounds, depending upon the usage of the system, for example, the system can contain lysing agents such as purified saponin disclosed in U.S. Pat. No. 3,883,425 issued May 13, 1975 and entitled "Detoxification Of Saponins" when it is desired to process blood. The composition can also contain anticoagulant such as citrate or ethylenediamine-tetraaceticacid (EDTA).

The antibiotic blockers of the instant invention, in combination, serve as bacteriostatic agents. In addition, it may be desirable to add additional bacteriostatic agents to prevent the replication of all microorganisms in the specimen The bacteriostatic agent chosen should be noncidal to microorganisms of interest, as previously defined. The choice of bacteriostatic agents will be dependent on the type of specimen and the identity of the microorganism of interest. Also, it may be impossible or highly unlikely that certain microorganisms could exist in particular specimens so that there would be no need to employ a particular bacteriostatic agent directed toward controlling the growth of that certain microorganism in the particular system. Thus a carbohydrate, a sugar or salt such as sodium chloride or its equivalent is desirably employed to increase the hypertonicity of the aqueous specimen or specimen receiving fluid with respect to urine specimens, swab collected specimens, and other specimens in order to control the replication of the more rapidly growing organisms, for example Enterobacteraciae and Proteus. Suitable salts include sodium or potassium chloride, ammonium salts such as $(NH_4)_2SO_4$ and $NH_4NO_3$ and other salts of nitrates, sulfates, acetates and admixtures thereof. Suitable sugars include sorbitols, mannitols, glucose and the like. Preferably, a sodium or potassium chloride is utilized in the range of 0–171.1 mM, preferably from about 8.5 mM to about 136.9 mM, and most preferably from about 17.1 mM to about 85.5 mM in the specimen and specimen transport system admixture combined.

It may be desirable to add a substance effective for inhibiting the replication of gram positive microorganisms without being cidal to microorganisms of interest. For example, *Streptococcus faecalis* and *Streptococcus aqalactiae* may mask the presence of *Streptococcus pyogenes* because the two former organisms are fast-growers. Since *S. faecalis*, *S. aqalactae* and *S. pyoqenes* are all gram positive, it is not desirable to employ a substance cidal toward the gram positive class in the specimen transport system as *S pyoqenes* would be killed along with the other gram positive organisms and thus could not be isolated. It has now been found that effective growth inhibition of microorganisms without death can be achieved by the combination of the specimen transport system components plus a dye such as brilliant green or malachite green. Also effective in combination with the other system components is oxgall (dehydrated fresh bile). Brilliant Green is utilized in the range of 0 to 4.1 uM. It is preferred that it be added from about 100 nM to about 3.3 uM. Most preferred is a range of about 200 nM to about 2.1 uM. If Malachite Green is employed, the concentration in the final specimen solution should be from about 0 to 5.5 uM, preferably 100 nM–4.4 uM and most preferred 2.7 uM–27.4 uM. Other dyes may be employable at concentrations inhibitory to gram positives without being cidal, the inhibition reversible upon adequate dilutions.

Oxgall is utilized, in an amount from about 0 w/v to about 0.002% w/v, preferably 0.00005% w/v to about 0016% w/v, and most preferably from about 0.0001% w/v to about 0.001% w/v. Since oxgall is literally dehydrated fresh bile from oxen gall bladders, no certain molecular weight or consistency between preparations is possible. Therefore, the amounts given are estimated based on preparations purchased from Difco, catalogue #0128-02.

In some specimens, it may be desirable to add additional bacteriostatic agents. It has been found that calcium propionate, methyl paraben, potassium sorbate, sodium nitrate, and sodium benzoate appropriately work in the transport system as a bacteriostat primarily for *E. coli*, *Klebsiella*, and *Enterobacteriaceae*. These agents are generally effective from about 0.1% to about 10% w/v preferably 0.01% to about 8.0% w/v, and most preferred 0.1% to about 5% w/v. Calcium propionate is most preferred. Based on the molar equivalents of propionic acid as the active ingredient, it is utilized from about 0 to about 42.1 mM, preferably from about 42 uM to about 33.7 mM, and most preferably 421.4 uM to about 21.2 mM.

It is desirable to keep the pH of the system at about 6.5–7.5. Therefore, it may be appropriate to buffer the specimen with an effective pH buffer after adjusting specimens which are markedly acidic or basic. The pH of the urine is one indication of the body's natural defense mechanism. Thus, extremes of pH (acidic) may kill microorganisms of interest in the specimen before analysis. Extremes of pH may indicate rapid replication of microorganisms which may mask the microbial integrity at time $t_l$. However, the pH buffer must be compatible with the system. A preferred pH buffer is sodium bicarbonate. For urine, it may be present in the range from about 1.2 mM to about 238.0 mM, preferably from about 2.4 mM to about 59.5 mM. The concentration may be modified to achieve the desired buffering result. For other specimens, not including blood which does not generally require a buffer, the concentration may range from about 0 mM to about 60 mM, preferably from about 0.6 mM to about 24.0 mM depending on the needs of pH adjustment.

The specimen transport system chemical component is preferably a dry admixture which is employable in a specimen collection vessel for aqueous specimens, and which will dissolve in said aqueous specimen when the specimen is introduced into the collection vessel. It is most preferable if the collection vessel is utilized for specimen transport and perhaps other processing steps to reduce manipulation of the sample and risk of contamination. An example of collection/processing vessel can been seen in Example XVI. An example of use of the dry admixture in connection with urine may be seen in Example XI. It is more convenient to employ a dry, water-soluble, admixture in a collection vessel for most of the specimen transport system components. It is highly desirable to employ L-cysteine or any sulfhydryl-containing substance employed in a dry admixture to increase shelf-life of the specimen transport system admixture Where a liquid sulfhydryl compound, such as mercaptoethanol, is employed it is desirable to provide a closed container with an inert atmosphere, such as $N_2$ gas, to prevent oxidation.

In specimens which are not inherently aqueous, or which are collected using an absorption device such as a swab, it is necessary to employ an aqueous fluid as part of the specimen transport system This aqueous fluid comprises an effective diluent which in combination with the dry admixture components will preserve the microbial integrity of the specimen All the specimen transport system components may be put in the dry admixture with the exception of agar, an optional nutrient which may be desirable for some microorganisms of interest and inherently liquid substances such as mercaptoethanol. Agar must be pre-dissolved with adequate heat in an aqueous solution. In one embodiment of a swab-collected specimen transport system, nutrients comprising growth-supporting broth and agar will be employed so that an appropriate volume of aqueous solution for receiving the swab will contain effective amounts of the broth and agar. In this embodiment, a compartment in the device for receiving the swab will contain an aqueous receiving fluid, the compartment being breakable by the swab to release the liquid so that the dry admixture of specimen transport system components will be mixed with, and dissolved in, the aqueous broth-agar solution near the time the swab/specimen is collected and placed in the specimen transport device. It may be practical to add certain components of the specimen transport system to an aqueous receiving solution rather than a dry admixture because of the low concentrations of the components required. An aliquot of a concentrated stock solution of the component might be added to the aqueous receiving solution rather than admixing a small amount of dry component with the dry admixture.

Thus, in one embodiment of a specimen transport system for specimens collected by swab, an aqueous receiving solution is prepared according to the following method.

DILUENT PREPARATION

Preparation of stock solution
  a. Preparation of diluent without Brilliant Green:
  Mueller-Hinton Broth (MHB) 4.4 g (BBL; Cockeysville Md)
  Agar 0.2 g
  Starch 0.8 g
  100 ml $H_2O$
  Autoclave for 15 minutes at 121° C.
  Store 25 ml in 50 ml sterile plastic conical tubes in 4° C. cold room
  b. Preparation of diluent with Brilliant Green:
  Mueller-Hinton Broth 4.4 g
  Agar 0.2 g
  Starch 0.8 g
  75 ml $H_2O$
  Boil the mixture, then add 25 ml 20 ug/ml
  Brilliant Green (2 mg/100 ml $H_2O$). Autoclave in 100 ml aliquots for 15 minutes at 121° C. The color should be lime green as it cools to room temperature.
  Store 25 ml in 50 ml sterile plastic conical tubes in 4° C. cold room.
  c. Preparation of 1:100 hemoglobin solution:
  1. Put 0.1575 g hemoglobin* powder into beaker.
  2. Put in 100 ml Deionized $H_2O$.
  3. Put stir bar into beaker.
  4. Stir solution slowly for at least 30 min. without heat.
  5. Using a spatula work in any floating powder on the foam or glass back into the solution until completely dissolved. Keep doing this until all powder is dissolved.
  6. Using two filter papers (Whatman 934 AH -glass fiber), prefilter the solution, wash filtering unit after filtering 100-300 ml. Do not filter more than 300 ml at a time.
  7. Autoclave in 100 ml aliquots for 15 minutes at 121° C.
  8. Store 50 ml in 50 ml sterile plastic conical tubes in 4° C. cold room.
* GIBCO Dri-Form Hemoglobin. Catalog #M00230.
  d. The stock solution is 1 part of diluent mixed with 1 part of hemoglobin solution. Final concentration of stock aqueous receiving solution:

1:200 hemoglobin - 0.07875%
MHB full-strength - 2.2%
Starch - 0.55% (0.15% is from MHB full-strength)
Agar - 0.1%
Brilliant Green - 0.00025% (2.5 ug/ml)

A dry admixture of L-cysteine, SPS, thioglycolate, sodium chloride and calcium propionate to provide the following concentration in the transport system aqueous receiving solution is then made:
L-Cysteine 0.25% (2.06 mM)
SPS 0.6%
Thioglycolate 0.01% (108.6 mM)
Sodium chloride 2.0% (34.33 mM)
Calcium Propionate 3.0% (20.52 mM).

The dry admixture is added to the appropriate volume of the aqueous receiving solution, preferably at the time of specimen collection.

Other embodiments will be evident from the above disclosure. It is envisioned that a fully dry admixture will be more appropriate for aqueous specimens such as urine and blood. A dry admixture and a separate aqueous receiving solution might be more preferable for a swab-absorbed specimen. Still another embodiment is a fully liquid system where the ingredients normally in the dry admixture are pre-dissolved in an aqueous receiving solution and stored in a non-oxidizing environment.

As an example of a device for collection of aqueous specimens, a urine collection/transport device incorporating a dry admixture such as disclosed above with an additional pH buffering substance is disclosed so that a patient may micturate directly into the collection/transport device, the dry admixture immediately mixing with and dissolving in the urine specimen. The device is then closed and transported to the laboratory. The volume of the specimen is standardized by the device so that the concentration of the water-soluble dry admixture once solubilized will be appropriate to preserve the microbial integrity of the specimen.

EXAMPLE I

Preservation of Microbial Integrated of a Reconstructed Specimen in the Absence of Antibiotics A reconstruction specimen was prepared by inoculating a sterile cotton swab with 0.1 ml of a suspension of *Pseudomonas aeruqinosa* ($1 \times 10^4$ organisms per ml) (isolated and identified from a clinical specimen according to known procedures approved by the American Society of Microbiology). The swab was placed in either 5 mls of Mueller-Hinton Broth Mix [hereinafter MHBM] 2.26 Mueller-Hinton Broth (MHB) (BBL Microbiology Systems, Cockeysville, Md. 21030); 0.55% starch (0.15% from MHB); 0.10% Agar and 0.079% hemoglobin or the Specimen Transport System composition described in the following table. The results indicate that the specimen transport system was effective in maintaining the microbial integrity of the specimen. The survival rate was determined by inoculating three chocolate agar plates with 0.01 ml of treated (specimen transport system) or untreated (MHBM alone) specimen at various time points. The number of colonies which grew on each plate were counted and an average of the three plates taken. A survival rate of 1.00 indicates 100% survival, values greater than 1.00 indicate growth and values less than one indicate death.

It is evident that the specimen transport system used in the above example preserved the microbial integrity of the sample so that quantitation of the number of microorganisms of interest at 72 hours after specimen collection would be possible. Without use of the specimen transport system of the subject invention, uncontrolled growth of the organism occurred. For example, at 24 hours, the sample without the subject invention exhibited over a 58 fold increase from time of specimen collection to time of analysis. It is predictable that false positive results as to the microbial population present in the specimen at the time of collection would be obtained by a laboratory analyzing the specimen to which no specimen transport system was added. Even early as 4 hours past the time of collection, the results would be skewed.

| Survival Rate Over Time | | | | | | |
|---|---|---|---|---|---|---|
| | Time in Hours | | | | | |
| | 0 | 4 | 6-8 | 24 | 48 | 72 |
| With Transport System Composition* | 1.00 | 1.02 | 0.79 | 1.08 | 1.02 | 0.66 |
| Without Transport System Composition | 1.00 | 2.91 | 3.80 | 58.13 | 58.13 | 58.13 |

*2% NaCl; 3% calcium propionate; .25% cysteine. $2.5 \times 10^{-4}$% Brilliant Green; 0.6% SPS; 0.01% thioglycolate; 2.2% Mueller-Hinton Broth; 0.55% starch (0.15% contributed by Mueller-Hinton Broth); 0.1% agar; 0.07875% Hemoglobin (All % in weight per total volume).

EXAMPLE II

Preservation of the Microbial Integrity of a Reconstructed Specimen in the Presence of Antibiotics The reconstructed specimens were prepared as described in Example I. The same specimen transport system composition was tested. Antibiotics were added at a concentration of the anticipated average maximum serum level. A value of 1.00=100% survival. Without the disclosed invention, the microbial integrity of the specimen clearly began to deteriorate even 4 hours after the specimen was taken. In the table below, it can be discerned that false negative cultures would be highly probable. Quantitation without use of the disclosed composition would be highly inaccurate.

| Survival Rate Over Time | | | | | | |
|---|---|---|---|---|---|---|
| | Time in Hours | | | | | |
| | 0 | 4 | 6-8 | 24 | 48 | 72 |
| Amikacin (2/ug/ml) & Transport System | 1.00 | 1.08 | 1.11 | 1.01 | 1.10 | 1.14 |
| Amikacin (2/ug/ml) alone | 1.00 | 0* | 0 | 0 | 0 | 0 |
| Piperacillin (60 ug/ml) + Transport System | 1.00 | 0.99 | 1.07 | 1.13 | 0.91 | 0.95 |
| Piperacillin (60 ug/ml) alone | 1.00 | 0.76 | 0.21 | 0.01 | 0 | 0 |
| Ticarcillin (150 ug/ml) + Transport System | 1.00 | 0.97 | 1.06 | 1.12 | 1.02 | 1.01 |
| Ticarcillin (150 ug/ml) alone | 1.00 | 0.68 | 0.30 | 0 | 0 | 0 |

*0 = no growth discernable

EXAMPLE III

Synergistic Effect of Combined Specimen Transport System Components On Preservation of the Microbial Integrity of a Reconstructed Specimen Reconstructed specimens were prepared as described in Example I with the indicated microorganisms listed in each table below rather than *P. aeruqinosa*.

It can be seen in the Survival Rate results that the combined components of the specimen transport system exert a synergistic effect compared with individual components. For example, in Table III-4, the specimen transport system held the survival over time at a relatively constant level. Growth occurred with the other individual treatments, in some cases the overgrowth of the microorganism dominating the plate (TNTC values). If multiple organisms were present as would be the case in an actual specimen, this overgrowth would be especially unsatisfactory. In Table III-1, it can be seen that SPS, NaCl or MHB when used alone did not allow quantitative survival at 24 hours.

The following were tested alone or in combination with other components:

| Mueller-Hinton Broth (MHB) | |
|---|---|
| Beef Extract | 0.3% |
| Acid Hydrolysate of Casein | 1.75% |
| Starch | 0.15% |
| Mueller-Hinton Broth Mix (MHBM) | |
| Mueller-Hinton Broth | 2.0% |
| Starch | 0.55% (0.15% from MHB) |
| Agar | 0.10% |
| Hemoglobin | 0.07875% |
| Brilliant Green Mueller-Hinton Broth Mix | |
| Mueller-Hinton Broth | 2.2% |
| Starch | 0.55% (0.15% from MHB) |
| Agar | 0.10% |
| Hemoglobin | 0.07875% |
| Brilliant Green | 0.00025% |

TRANSPORT SYSTEM

Brilliant Green Mueller-Hinton Broth Mix+0.25% Cysteine+0.6% SPS+2% NaCl+0.1% Thioglycolate All numbers following organism identity indicate the culture number from the American Type Culture Collection Rockville, Maryland. SPS=sodium polyanethol sulfonate.

TABLE III-1

| Survival Rate of *Haemophilus influenzae* 19418 | | | | |
|---|---|---|---|---|
| | Transport Time in Hours | | | |
| | 0 | 4 | 6-8 | 24 |
| Individual Components | | | | |
| 0.5% Cysteine | 1.00 | 1.02 | 0.98 | 2.05 |
| 0.6% SPS | 1.00 | 1.10 | 1.07 | 0.08 |
| 2% NaCl | 1.00 | 0.23 | 0.21 | 0.006 |
| Mueller-Hinton Broth | 1.00 | 0.87 | 0.84 | 0.04 |
| Mueller-Hinton Broth Mix | 1.00 | 1.64 | 3.60 | 7.85 |
| Brilliant Green Mueller-Hinton Broth Mix | 1.00 | 1.32 | 1.41 | 1.02 |
| Combined Components | | | | |
| Transport System | 1.00 | 1.01 | 0.97 | 0.76 |

TABLE III-2

Survival Rate of
*Streptococcus pneumoniae* 6301

| | Transport Time in Hours | | | |
|---|---|---|---|---|
| | 0 | 4 | 6-8 | 24 |
| Individual Components | | | | |
| 0.5% Cysteine | 1.00 | 0.65 | 0.19 | 0.03 |
| 0.6% SPS | 1.00 | 1.11 | 1.02 | 2.72 |
| 2% NaCl | 1.00 | 0.94 | 1.21 | 0.72 |
| Mueller-Hinton Broth | 1.00 | 1.09 | 1.62 | TNTC |
| Mueller-Hinton Broth Mix | 1.00 | 1.36 | 3.33 | 8.10 |
| Brilliant Green Mueller-Hinton Broth Mix | 1.00 | 1.04 | 0.98 | 0.69 |
| Combined Components | | | | |
| Transport System | 1.00 | 0.90 | 0.85 | 0.66 |

TNTC = Too Numerous To Count

TABLE III-3

Survival Rate of
*Streptococcus pyogenes* 19615

| | Transport Time in Hours | | | |
|---|---|---|---|---|
| | 0 | 4 | 6-8 | 24 |
| Individual Components | | | | |
| 0.5% Cysteine | 1.00 | 1.08 | 1.21 | 3.61 |
| 0.6% SPS | 1.00 | 1.05 | 1.54 | 2.60 |
| 2% NaCl | 1.00 | 1.11 | 1.12 | 1.82 |
| Mueller-Hinton Broth | 1.00 | 1.34 | 1.61 | 6.90 |
| Mueller-Hinton Broth Mix | 1.00 | 1.56 | 1.95 | 4.32 |
| Brilliant Green Mueller-Hinton Broth Mix | 1.00 | 1.53 | 1.86 | 1.54 |
| Combined Components | | | | |
| Transport System | 1.00 | 0.94 | 0.91 | 0.68 |

TABLE III-4

Survival Rate of
*Staphylococcus aureus* 25923

| | Transport Time in Hours | | | |
|---|---|---|---|---|
| | 0 | 4 | 6-8 | 24 |
| Individual Components | | | | |
| 0.5% Cysteine | 1.00 | 1.30 | 1.46 | 4.08 |
| 0.6% SPS | 1.00 | 1.65 | 3.73 | TNTC |
| 2% NaCl | 1.00 | 1.44 | 2.32 | TNTC |
| Mueller-Hinton Broth | 1.00 | 2.80 | 4.57 | TNTC |
| Mueller-Hinton Broth Mix | 1.00 | 1.98 | 14.11 | 48.43 |
| Brilliant Green Mueller-Hinton Broth Mix | 1.00 | 0.94 | 0.93 | 0.35 |
| Combined Components | | | | |
| Transport System | 1.00 | 0.94 | 0.86 | 0.80 |

TNTC = Too Numerous To Count

TABLE III-5

Survival Rate of
*Streptococcus faecalis* 2492-2

| | Transport Time in Hours | | | |
|---|---|---|---|---|
| | 0 | 4 | 6-8 | 24 |
| Individual Components | | | | |
| 0.5% Cysteine | 1.00 | 1.40 | 2.00 | TNTC |
| 0.6% SPS | 1.00 | 2.31 | 3.98 | TNTC |
| 2% NaCl | 1.00 | 1.60 | 3.08 | TNTC |
| Mueller-Hinton Broth | 1.00 | 2.99 | 7.18 | TNTC |
| Mueller-Hinton Broth Mix | 1.00 | 11.14 | 24.83 | 60.56 |
| Brilliant Green Mueller-Hinton Broth Mix | 1.00 | 1.59 | 2.01 | 2.83 |
| Combined Components | | | | |
| Transport System | 1.00 | 0.92 | 0.85 | 2.49 |

TNTC = Too Numerous To Count

TABLE III-6

Survival Rate of
*Escherichia coli* 25922

| | Transport Time in Hours | | | |
|---|---|---|---|---|
| | 0 | 4 | 6-8 | 24 |
| Individual Components | | | | |
| 0.5% Cysteine | 1.00 | 3.04 | 6.63 | TNTC |
| 0.6% SPS | 1.00 | 4.02 | 18.20 | TNTC |
| 2% Salt | 1.00 | 2.33 | 6.29 | TNTC |
| Mueller-Hinton Broth | 1.00 | 3.66 | 15.40 | TNTC |
| Mueller-Hinton Broth Mix | 1.00 | 4.40 | 28.44 | 59.87 |
| Brilliant Green Mueller-Hinton Broth Mix | 1.00 | 2.62 | 6.16 | 72.46 |
| Combined Components | | | | |
| Transport System | 1.00 | 0.98 | 1.03 | 0.67 |

TNTC = Too Numerous To Count

TABLE III-7

Survival Rate of
*Klebsiella pneumoniae* 632-2

| | Transport Time in Hours | | | |
|---|---|---|---|---|
| | 0 | 4 | 6-8 | 24 |
| Individual Components | | | | |
| 0.5% Cysteine | 1.00 | 2.71 | 5.68 | TNTC |
| 0.6% SPS | 1.00 | 4.87 | TNTC | TNTC |
| 2% NaCl | 1.00 | 3.41 | 7.20 | TNTC |
| Mueller-Hinton Broth | 1.00 | 4.90 | TNTC | TNTC |
| Mueller-Hinton Broth Mix | 1.00 | 5.33 | 53.09 | 96.41 |
| Brilliant Green Mueller-Hinton Broth Mix | 1.00 | 6.87 | 31.98 | 59.17 |
| Combined Components | | | | |
| Transport System | 1.00 | 1.08 | 1.03 | 0.70 |

TNTC = Too Numerous To Count

EXAMPLE IV

Preservation of Microbial Integrity of a Throat Swab Specimen from a Normal Donor to Which a Pathogen is Added The effectiveness of the disclosed specimen transport system on preserving the microbial integrity of a throat swab specimen containing a known amount of a pathogenic microorganisms along with the normal flora found in the throat is shown in the following table. It was demonstrated that overgrowth of normal flora could mask a pathogenic microorganism in a specimen for analysis.

Normal throat flora were collected from 20 healthy donors (three swabs per donor). Each swab was then inoculated with between $10^4$–$10^6$ of a human pathogen. The microorganisms present on each swab were subsequently extracted at time zero by vigorous agitation into 5 ml of a selected transport system. The swabs were discarded, and the liquid portions were held at 24° C. for subsequent quantitative analysis at 0, 4, 6, and 24 hours in order to determine the relative survival of the pathogen versus overgrowth by normal flora present on the swab. The following organisms were tested: *E. coli, P. aeruqinosa, S. aqalactiae, H. influenzae, S. pyoqenes, E. cloacae, K. pneumoniae, S. aureus,* and *S. faecalis.*

With the Stuarts transport system, overgrowth by the normal flora rendered the sample difficult to interpret within six (6) hours. The low survival observed at 24 hours (0.39) could either reflect death of the pathogen or masking of the organism by excessive normal flora. Similar results were obtained with the Amies transport system. The amount of overgrowth varied depending on the pathogen under analysis. The more fastidious organisms (e.g., *Haemophilis influenzae*) were more susceptible to overgrowth. Excessive growth of normal throat flora was effectively suppressed with the disclosed specimen transport system, which prevented overgrowth of the pathogen by normal flora in the absence of antibiotic over 24 hours.

Detectability of a Pathogen in the Presence of Normal Flora
[Survival 1.00 = 100%]

|  | Time in Hours | | | |
| --- | --- | --- | --- | --- |
|  | 0 | 4 | 6 | 24 |
| Normal Flora + *Streptococcus agalactiae* Plus Specimen Transport System[1] | 1.00 | 1.00 | 0.87 | 0.83 |
| Normal Flora + *Streptococcus agalactiae* With Stuart's system[2] | 1.00 | 1.09 | [3] | [3] |

[1]Specimen Transport System utilized in this Example comprised an admixture of 1.5% NaCl, 2.0% cysteine, 0.6% SPS, and 0.01% thioglycolate.
[2]Stuarts system as disclosed in Stuart et al, "The Problem of Transport of Specimens for Culture of Gonococci," 45 Canadian J. of Public Health 73 (1954).
[3]Overgrowth of normal flora making accurate count difficult.

EXAMPLE V

Preservation of Microbial Integrity in a Reconstructed Specimen from $T_O=0$ to $T_1=4$ Hours in the Presence of Antibiotics It is recommended in most manuals that a specimen be analyzed within 2 hours after collection. However, this assumed safe time period is not valid in all situations. The disclosed invention is shown to be a significant improvement over prior art transport systems which do not prevent significant deterioration of microbial integrity even within as little as 15-20 minutes.

The Amies transport system C. Amies et al., 58 *Canadian J. Public Health*, 296 (1957) (available from Curtin Matheson Scientific, Inc.) The formula (per liter of distilled water) is:

| - sodium chloride | 3.0 g |
| --- | --- |
| - potassium chloride | 0.2 g |
| - calcium chloride | 0.1 g |
| - magnesium chloride | 0.1 g |
| - mono potassium phosphate | 0.2 g |
| - disodium phosphate | 1.15 g |
| - sodium thioglycollate | 1.0 g |
| - agar | 7.37 g |

Stuart's Transport Medium, 45 *Canadian J. Public Health* 73, 75 (1956) is the following: 6 g Bacto Agar in 1900 mls distilled water, 2 ml thioglycollic acid (Difco) brought to pH 7.2 with 1N NaOH. 100 ml 20% (w/v in water) Na glycerophosphate and 20 ml CaCl$_2$ (1% w/v in water) is then added. 20 ml 1% w/v CaCl$_2$ is added and the solution brought to pH 7.4 with 1N Hcl. 4 ml 0.1% methylene blue is then added.

The specimen transport system of the instant invention depicted in the following charts was of the formula:

| 2% | Na Cl |
| --- | --- |
| .25% | L-cysteine (free base) |
| 3% | Calcium propionate |
| 2.5 × 10$^{-4}$% | Brilliant Green |
| 0.6% | SPS |
| 0.01% | Thioglycolate |
| 2.2% | Mueller-Hinton Broth |
| 0.55% | Starch |
| 0.1% | Agar |
| 0.7875% | Hemoglobin |

Antibiotics were added at the average maximum serum level as determined by published reports. These values are set out in Example VI, Table VI-2.

The organism/ml level was tested at each time point indicated on the graphs (FIG. 11–FIG. 16).

Figure 11:
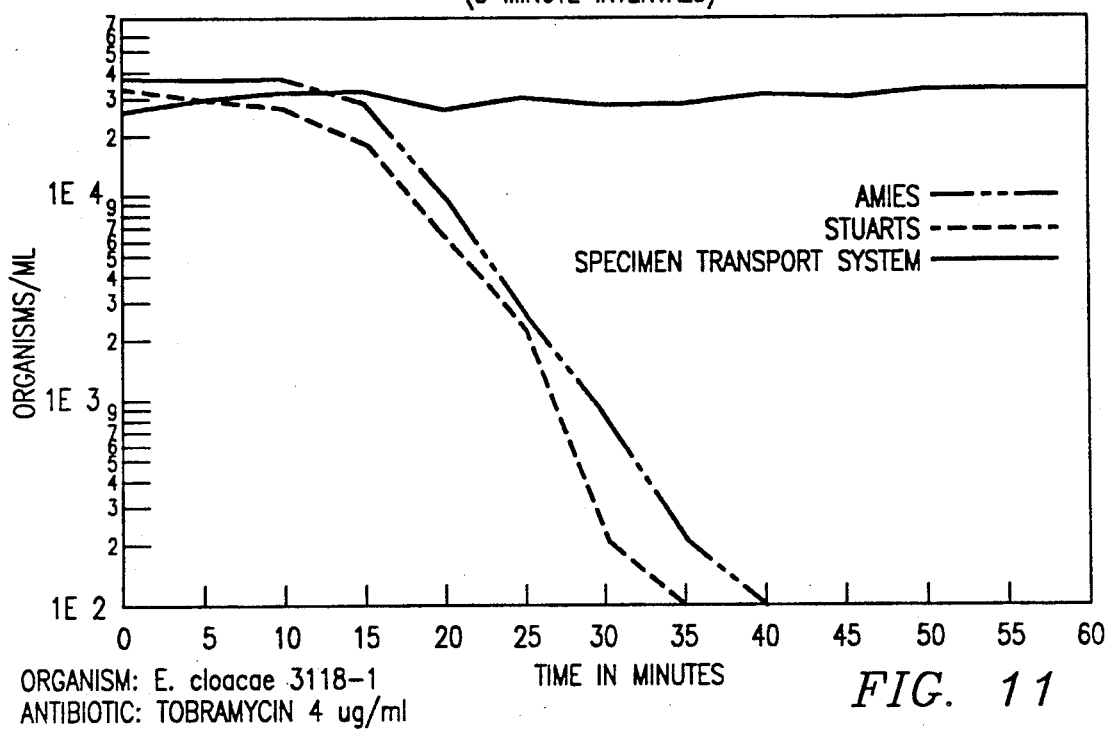
FIG. 11 graphically depicts the preservation of microbial integrity of a specimen in the presence of an antibiotic in the first hour with the subject invention as compared to conventional systems (detailed in Example V).

In FIG. 11, it can be seen that the microbial integrity of the reconstructed specimen containing *Enterobacter cloacae* using conventional transport systems deteriorates within 20–30 minutes in the presence of the antibiotic Tobramycin at 40 ug/ml. The specimen transport system in contrast held the count constant over time.

Figure 12:
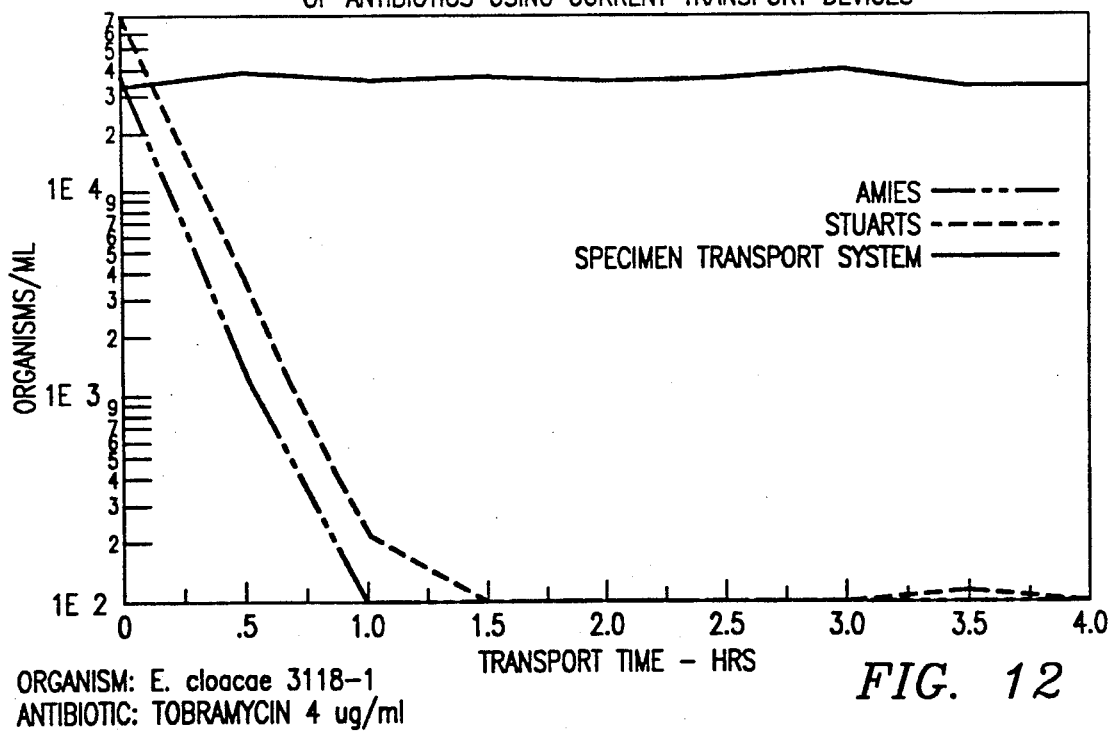
FIGS. 12-16 graphically depicts the preservation of microbial integrity of a specimen in the presence of an antibiotic over a four hour time period as compared to conventional systems (detailed in Example V).

In FIG. 12, it can be seen that the specimen transport system exhibits superiority 4 hours after specimen collection, thus surpassing the two-hour recommendation for specimen analysis in the prior art.

Figure 13:
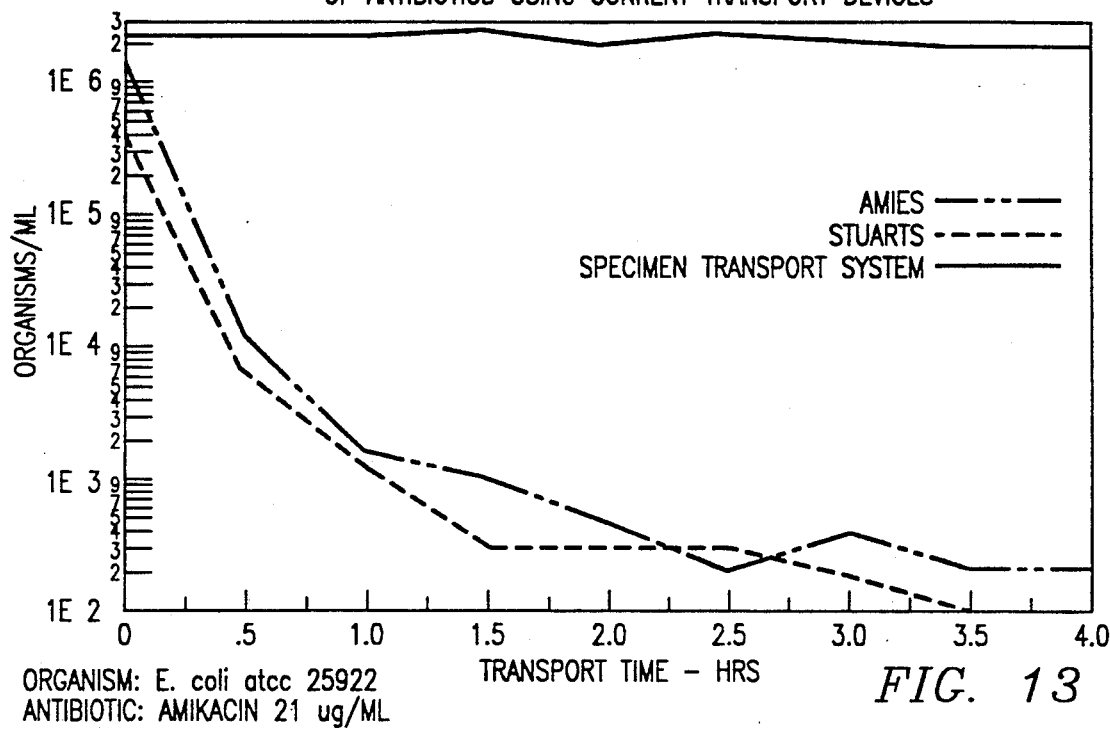

In FIG. 13, an *Eschericha coli* reconstructed specimen is tested. The specimen transport system exhibits superiority in maintaining the microbial integrity of the specimen in the presence of Amikacin at 21 ug/ml.

Figure 14:
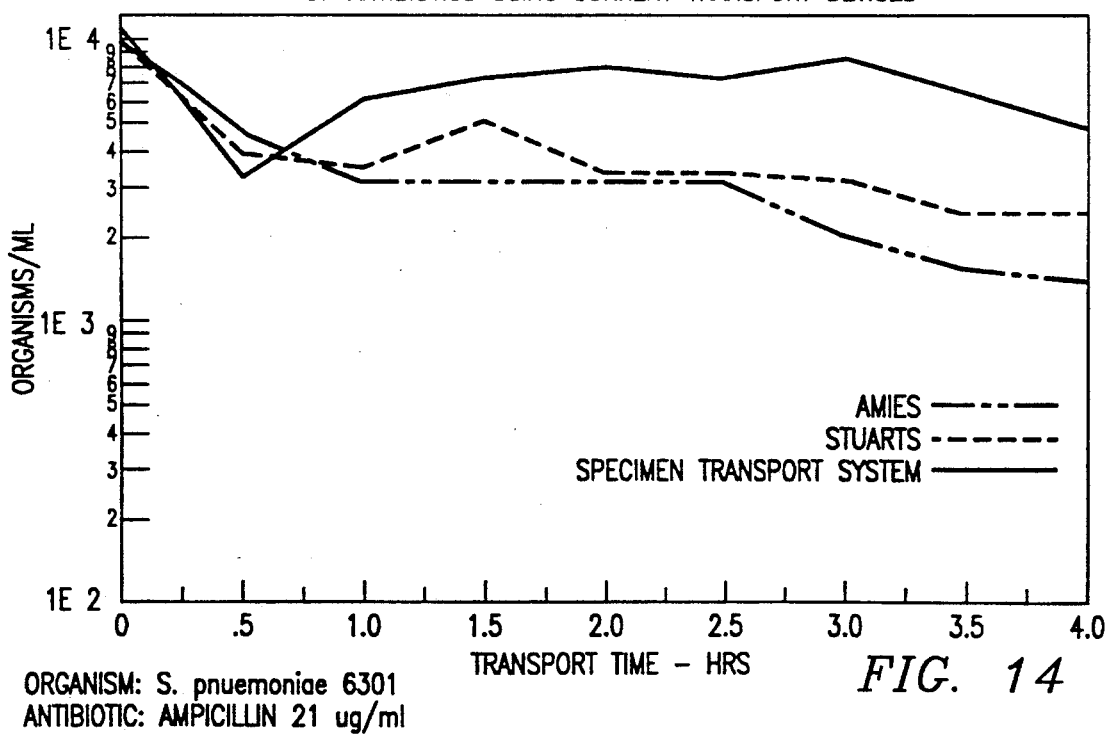

FIG. 14 depicts the preservation of the microbial integrity of *Streptococcus pneumoniae* with the subject invention compared to conventional systems in the presence of Ampicillin at 21 ug/ml. A somewhat higher recovery in organism/ml is demonstrated.

Figure 15:
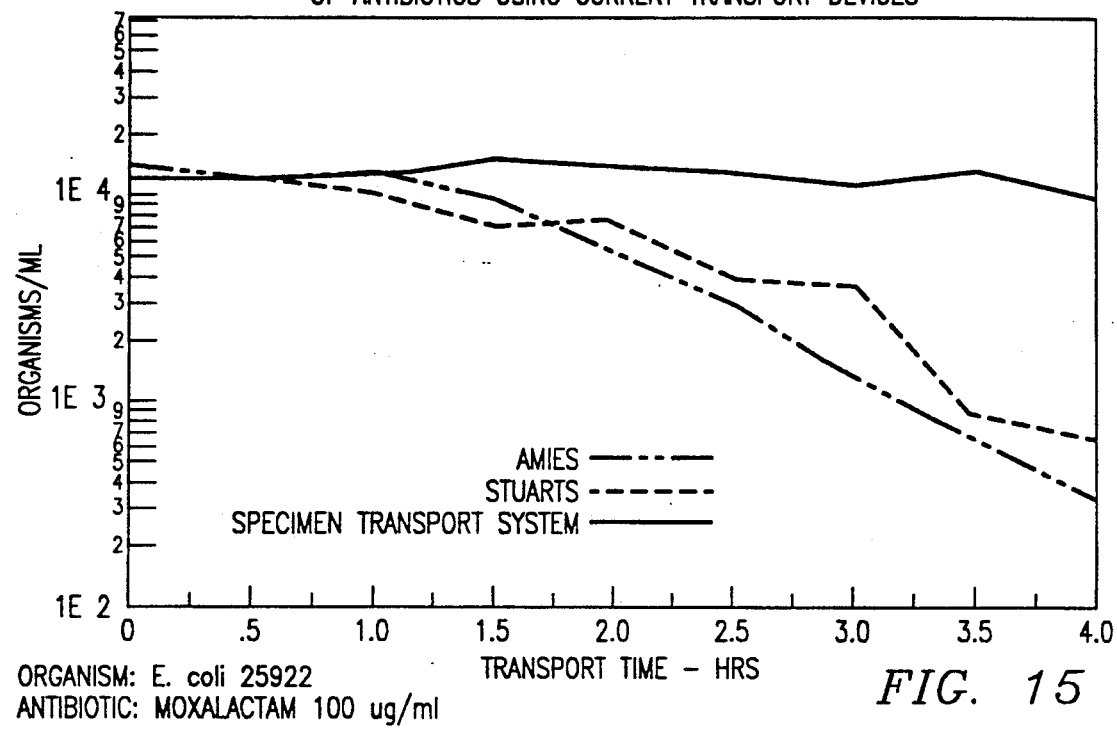

FIG. 15 depicts the effect of Moxalactam 100 ug/ml in a reconstructed *E. coli* specimen. The specimen transport system was able to preserve microbial integrity beyond a two-hour transport time.

Figure 16:
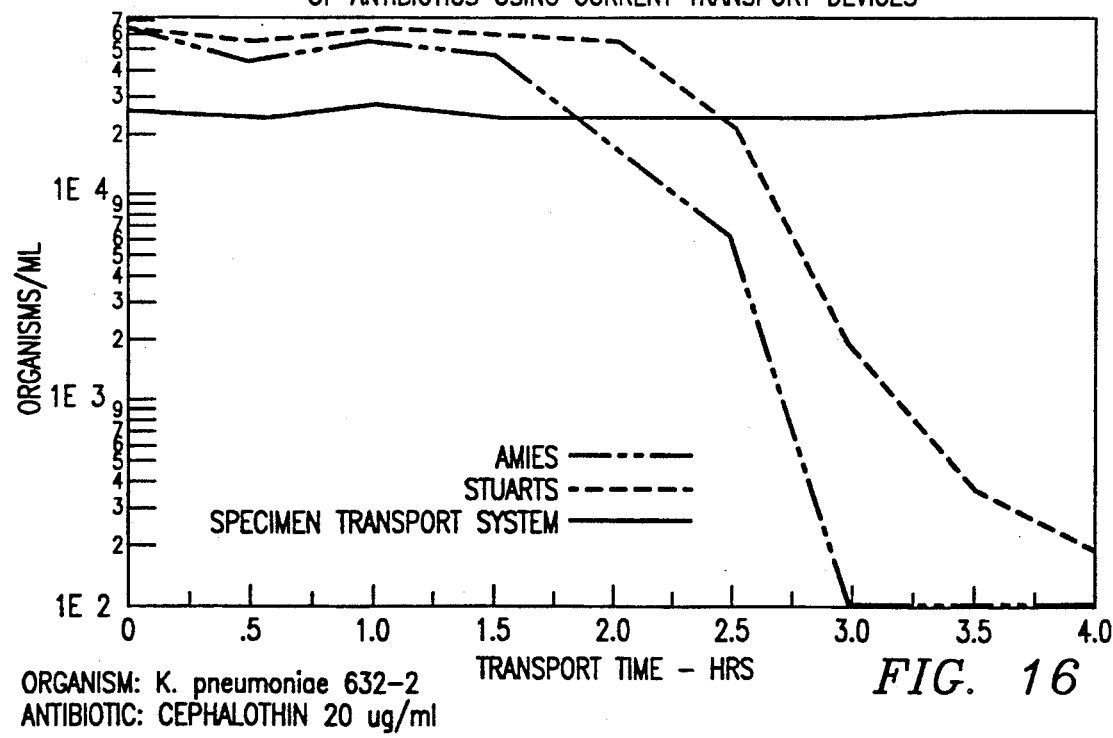

FIG. 16 depicts the effect of the specimen transport system on *Klebsiella pneumoniae* in the presence of Cephalothin. The Amies and Stuarts Systems received a slightly higher inoculum than the Specimen Transport System, however the former two systems still show dramatic drops in organisms/ml at 3 hours.

EXAMPLE VI

Comparative Average Microbial Integrity (SWABS)

Specimen transport was tested by obtaining microbial pathogens from the American Type Culture Collection (ATCC), Rockville, Md and inoculating multiple sterile cotton swabs with $1 \times 10^4$ of a single pathogen. Each inoculated swab was placed in an aqueous preparation comprising 0.25% (2.06 mM) L-cysteine (free base), 0.6% SPS, 0.01% (108.6 mM) thioglycolate, 2.0% (34.22 mM sodium chloride), 3.0% (20.52 mM) calcium propionate, 2.2% Mueller-Hinton Broth, 0.55% starch; 0.1% agar; 0.7875% (1.2 uM) hemoglobin, and $2.5 \times 10^{-4}$% Brilliant Green (0.5 uM) or the transport medium disclosed in 45 *Canadian J. of Public Health* 73 (1954) or Amies's Transport Medium (without charcoal) (58 *Canadian J. of Public Health* 296 (1967)).

Either a specific concentration of a selected antibiotic or no antibiotic was added to each individual aqueous preparation. The antibiotic concentration was chosen according to published values of the average maximum serum levels that would be found in patients. This level is indicated for each antibiotic in Table VI-2. (It should be noted that for urine specimens, not tested in this example, 10X the antibiotic average maximum serum level was employed). The number of bacteria in each specimen were determined at each of 4 time points in the three transport solution preparations by transferring 0.01 ml to each of three chocolate agar plates, incubating at 37° C. for 24 hours, counting the number of colonies, and calculating the number of microorganisms surviving per ml.

In the chart below, a value of 1.00=100% survival. Thus at 0 hours, all test specimens show a value of 1.00. A value greater than 1.00 indicates replication of the organism occurred in the transport period by the factor times 1.00 which yields that value. A value less than 1 indicates that the numbers of organism were reduced during transport (death occurred). Thus a value of 0.5 indicates a loss of half the original number of organisms. The values in the chart are averaged for the gram negative organisms tested (see chart below) and the gram positive organisms tested (see chart below) for the antibiotic classes given.

TABLE VI-1

LIST OF ORGANISMS USED FOR SPECIMEN TRANSPORT SYSTEM COMPARISONS

|  | ATCC #[1] | CLINICAL STRAIN[2] |
|---|---|---|
| GRAM NEGATIVE | | |
| Enterobacter cloacae | | 3118-1 |
| Escherichia coli | 25922 | |
| Haemophilus influenzae | 19418 | |
| Haemophilus influenzae | 9795 (Type B) | |
| Haemophilus influenzae | 9133 | |
| Haemophilus influenzae | 8149 | |
| Klebsiella pneumoniae | | 632-2 |
| Pseudomonas aeruginosa | | 277 |
| Staphylococcus aureus | 25923 | |
| GRAM POSITIVE | | |
| Streptococcus agalactiae | 624 | |
| Streptococcus faecalis | | 2942-2 |
| Streptococcus pneumoniae | 6301 | |
| Streptococcus pneumoniae | 9163 | |
| Streptococcus pneumoniae | 10813 | |
| Streptococcus pneumoniae | 27336 | |
| Streptococcus pyogenes | 19615 | |
| Streptococcus pyogenes | 12344 (Type 1) | |
| Streptococcus pyogenes | 12383 (Type 3) | |
| Streptococcus pyogenes | 12385 (Type 4) | |

[1]American Type Culture Collection, Rockville, Md.
[2]Clinical isolate identified according to methods approved by the American Society of Microbiology.

TABLE VI-2

ANTIBIOTICS USED FOR EXPERIMENTS

| DRUG-MANUFACTURER | AVERAGE MAXIMUM SERUM LEVELS (ug/ml) |
|---|---|
| I. AMINOGLYCOSIDES | |
| AMIKACIN BASE - Bristol Laboratories | 21 |
| GENTAMICIN SULFATE - Schering Corporation | 6 |
| TOBRAMYCIN - Eli Lilly & Company | 4 |
| II. CEPHALOSPORINS | |
| CEFAMANDOLE LITHIUM - Eli Lilly & Company | 20 |
| CETRIAXONE - Hoffman-La Roche, Inc. | 90 |
| CEFOTAXIME SODIUM - Hoechst-Roussel Pharmaceuticals, Inc. | 20 |
| CEFOXITIN SODIUM - Merck, Sharp, & Dohme | 25 |
| CEPHALOTHIN SODIUM NEUTRAL - Eli Lilly & Company | 20 |
| MOXALACTAM DIAMMONIUM - Eli Lilly & Company | 100 |
| III. PENICILLINS | |
| AMPICILLIN TRIHYDRATE - Bristol Laboratories | 21 |
| CARBENICILLIN DISODIUM - Beecham Laboratories | 71 (20 E. coli) |
| METHICILLIN SODIUM - Bristol Laboratories | 9 |
| MEZLOCILLIN SODIUM - Miles Pharmaceuticals | 4 |
| PENICILLIN G POTASSIUM BUFFERED - Eli Lilly & Company | 20 |
| PIPERACILLIN SODIUM - Lederle Piperacillin, Inc. | 60 |
| TICARCILLIN DISODIUM - Beecham Laboratories | 150 |
| IV. OTHERS | |
| BACTRIM (Sufamethoxazole-Trimethoprim) - Hoffmann-La Roche, Inc. | 3 |
| CHLORAMPHENICOL - Parke-Davis | 18 |
| ERYTHROMYCIN GLUCEPTATE - Eli Lilly & Company | 8 |
| GANTRISIN (Sulfamethoxazole) - Hoffman-La Roche, Inc. | 100 |
| POLYMYXIN B SULFATE - Pfizer, Inc. | 2 |
| TETRACYCLINE HCl - Lederle Laboratories Division | 9 |
| VANCOMYCIN HYDROCHLORIDE - Eli Lilly & Company | 8 |

AVERAGED RECOVERY VALUES[1]
FINAL DEVICE COMPARISONS: TRANSPORT TIME IN HOURS

|  | 0 HR | | | HR | | | 24 HR |
|---|---|---|---|---|---|---|---|
|  | S.T.S.[1] | STUART'S[3] | AMIES'S[4] | S.T.S. | STUARTS | AMIES | S.T.S. |
| GRAM-NEGATIVES | | | | | | | |
| I. AMINOGLYCOSIDES | | 1.00 | | .93 | .002 | .003 | .73 |
| II. CEPHALOSPORINS | | 1.00 | | .69 | .20 | .12 | .45 |
| III. PENICILLINS | | 1.00 | | .95 | .36 | .40 | .80 |
| IV. OTHERS | | 1.00 | | .89 | .38 | .65 | .91 |
| V. NO ANTIBIOTIC | | 1.00 | | .97 | 8.91 | 14.67 | .84 |
| GRAM-POSITIVES | | | | | | | |
| I. AMINOGLYCOSIDES | | 1.00 | | .88 | .30 | .38 | 1.06 |
| II. CEPHALOSPORINS | | 1.00 | | .72 | .65 | .62 | .58 |
| III. PENICILLINS | | 1.00 | | .96 | .39 | .37 | .96 |
| IV. OTHERS | | 1.00 | | .93 | .76 | .77 | .77 |
| V. NO ANTIBIOTIC | | 1.00 | | .92 | 1.15 | 1.12 | 1.23 |
| TOTAL ANTIBIOTICS | | 1.00 | | .87 | .38 | .41 | .78 |

TABLE VI-2-continued

| | | | | | |
|---|---|---|---|---|---|
| TOTAL WITHOUT ANTIBIOTICS | 1.00 | | .94 | 5.03 | 7.90 | 1.04 |

| | 24 HR | | 48 HR | | |
|---|---|---|---|---|---|
| | STUARTS | AMIES | S.T.S. | STUARTS | AMIES |
| GRAM-NEGATIVES | | | | | |
| I. AMINOGLYCOSIDES | 0 | 0 | .44 | 0 | 0 |
| II. CEPHALOSPORINS | .08 | .04 | .28 | .03 | .02 |
| III. PENICILLINS | .11 | .08 | .57 | .06 | .03 |
| IV. OTHERS | .21 | .32 | .78 | .10 | .16 |
| V. NO ANTIBIOTIC | 41.28 | 46.04 | .55 | 33.65 | 39.73 |
| GRAM-POSITIVES | | | | | |
| I. AMINOGLYCOSIDES | .15 | .32 | 1.49 | .02 | .12 |
| II. CEPHALOSPORINS | .28 | .32 | .41 | .12 | .13 |
| III. PENICILLINS | .08 | .09 | 1.45 | .03 | .03 |
| IV. OTHERS | .52 | .51 | .62 | .33 | .24 |
| V. NO ANTIBIOTIC | 7.56 | 17.78 | 2.48 | 7.79 | 18.93 |
| TOTAL ANTIBIOTICS | .18 | .21 | .76 | .09 | .09 |
| TOTAL WITHOUT ANTIBIOTICS | 24.42 | 31.91 | 1.52 | 20.72 | 29.34 |

| NUMBER OF SPECIFIC DEVICE RECONSTRUCTIONS | | | |
|---|---|---|---|
| | S.T.S. | STUARTS | AMIES |
| WITH ANTIBIOTICS | 419 | 272 | 284 |
| WITHOUT ANTIBIOTICS | 119 | 131 | 68 |
| | 538 | 403 | 352 = 1293 Total Reconstructions |

[1] The above data the generated using 19 pathogens - listed in Table VI-A. Data from all gram negative organisms was averaged separately from gram positive organisms.
[2] S.T.S. = Speciment Transport System
[3] Stuart, 45 Canadian J. Public Health 73 (1954)
[4] Aimes, 58 Canadian J. Public Health 296 (1967) (without charcoal)

Now referring to FIG. 1, centrifugation article 20 is depicted which is disclosed in the above-described U.S. Pat. No. 4,131,512 and its division U.S. Pat. No. 4,212,948, which patents are herein incorporated by reference into this application. The incorporated patents are directed to a method and apparatus which provides for improved rapid quantitative analysis of a blood sample for the presence of microbial pathogens. The blood sample is lysed and deposited on a high density water immiscible, hydrophobic, nontoxic, liquid cushioning agent and subjected to centrifugation. The microbial pathogens contained in the lysed blood sample will collect in a layer adjacent the interface of the cushioning agent and the blood sample residue, and, in this concentrated form, can easily be separated from the residual portion of the blood sample for culturing and quantitative counting. As shown, the article 20 comprises an elongated tubular centrifugation vessel 22 having a conventional injectable closure member 24 which sealably closes the upper end thereof, and an injectable closure member 26 which sealably closes the lower end thereof. Article 20 contains an effective amount of cushioning agent 28. The specimen transport system when utilized in elongated tubular centrifugation vessel 22 is deposited as layer 30 of particulate solid on cushioning agent 28. The specimen transport system can be contained within an aqueous solution within article 20, e.g., about one-half milliliter, but it is preferred that said system be in the form of solid particulate 30 powder 30. Solid particulate powder 30 is not soluble within the liquid cushioning agent 28 and has a higher shelf stability than the liquid solution formed of the ingredients. In addition, the use of the particulate solid specimen transport system allows a novel sterilization technique to be carried out within the interior of article 20 which will be herein described below. In the preferred embodiment of the subject invention, the specimen transport system is present whether in aqueous solution or layer 30 sufficient so that when a sample fluid such as blood is deposited therein, the combination of specimen transport system and blood will contain from about 0.1 to about 6% by weight thereof of sodium polyanethol sulfonate; from about 0.5 to about 2.5% by weight of cysteine; from about 0.1 to about 1.6% by weight thereof of thioglycolate; and from about 5 micrograms per milliliter to about 500 micrograms per milliliter of para-aminobenzoic acid. In addition, since this particular embodiment is used for processing blood samples, the resulting total volume will also include from about 0.02 to about 1% by weight of purified saponin and from about 0.01 to about 0.5% by weight of EDTA. When the specimen transport system is in the form of an aqueous solution, the configuration vessel 22 will draw approximately 7.5 milliliters of blood. It is preferred that said specimen transport system be at least 3% by volume of the total liquid in centrifugation vessel 22 including the total quantity of the specimen transport system, the sample fluid and the cushioning agent and preferably from about 5% to about 30% by volume thereof. When the specimen transport system is in the form of particulate layer 30, the elongated tubular centrifugation vessel 22 will draw about 8 milliliters of blood. In the most preferred embodiment of the subject invention, layer 30 will contain 0.096 grams of cysteine; 0.008 grams of thioglycolate; 0.048 grams of sodium polyanethol sulfonate; 0.018 grams purified saponin; and 0.008 grams of EDTA. It is noted that the EDTA is not necessary to prevent blood clot formation so long as adequate amounts of sodium polyanetholsulfonate are present. For example, another satisfactory blood treating system (layer 30) contains 0.048 grams sodium polyanetholsulfonate, 0.08 grams cysteine, 0.009 grams thioglycolate and 0.019 grams purified saponin.

The combination of specimen transport system and urine will preferably contain from about 0.6 percent to about 2.0 percent by weight thereof sodium polyanetholsulfonate; from about 0.5 percent to about 2.5 percent by weight thereof, free-based cysteine; about 0.1 percent by weight thereof, thioglycolate; about 2.0 percent by weight thereof, sodium bicarbonate; and from about 2.5 percent to about 4.0 percent by weight thereof, sodium chloride. The sodium bicarbonate was added to the urine specimen transport system in order to adjust for the normal acidity of urine and thus attain a neutral pH. The added salt, in the form of, for example, sodium chloride, increases the bacteriostatic effect of the system in the absence of antibiotics in the urine. A free-based L-cysteine, such as ICN cysteine, is preferably substituted for the previously employed L-cysteine-HCl as the former does not produce a gaseous reaction when combined with the sodium bicarbonate buffer as seen previously in the L-cysteine-sodium bicarbonate mixture.

Centrifugation vessel 22 can be made of siliconized glass or hard plastic such as polycarbonate or polypropylene. Injectable closure members 24 and 26 can comprise rubber sealing stoppers. Injectable closure members 24 and 26 both carry indentations 24a and 26a, respectively, to enhance the ease of injection by common types of injection needles. Evacuated space 32 is maintained at a lower than atmospheric pressure at a predetermined value so that the centrifugation vessel can receive a known amount of liquid by injection through injectable enclosure member 24 without excessive pressure being built up within the interior thereof which would cause injectable closure members 24 and 26 to become dislodged from the openings within the centrifugation vessel 22.

Referring especially to injectable closure member 26 at the lower end of centrifugation vessel 22, it is noted that inner surface 34 of injectable closure member 26 is positioned at an angle with respect to the walls of centrifugation vessel 22.

It is noted that article 20 is especially designed to be utilized within an angle rotor centrifuge and that the angled inner surface 34 is a complement of the angle of the rotor. It should be noted, however, that the device of the subject invention can be utilized in a conventional swinging bucket-type centrifuge. In the latter instance, surface 34 should be perpendicular to the bottom of article 20 and is otherwise utilized in the same general manner as will be described herein below for the article 20 illustrated in FIG. 1. Surface 34 should be smooth and substantially free of interstitial spaces and crevices in which microbial pathogens could be entrapped. Further, the circular sealing area around surface 34 where the material of injectable closure member 26 meets the walls of the centrifugation vessel 22 should be tightly sealed so that the interface does not provide a large circular crevice in which microbial pathogens could become lodged.

The angle of incline of smooth surface 34 with respect to the walls of centrifugation vessel 22 is determined according to the centrifugation apparatus in which article 20 is to be centrifuged.

As discussed above, when a swinging bucket-type centrifuge is utilized, surface 34 will be positioned perpendicular to the bottom of the article 20. However, when an angle rotor centrifuge is utilized, surface 34 will carry the complement of the angle of the rotor. Therefore, in general, when the rotor angle ranges from about 60° to 10°, the angle of surface 34, or angle of incline 36 within the centrifugation vessel will range correspondingly from 30° to 80°. Thus, the angle of incline, depicted by arc 36, will generally be the complement of the angle at which device 20 rests within the centrifuge during centrifugation. For example, the angle of incline 36 depicted in FIG. 1 is approximately 34°. Thus, for example, when article 20 is placed in an angle rotor centrifuge in which centrifugation occurs at approximately 56°, fluids contained within article 20 will be forced against surface 34 at a substantial perpendicular angle.

The amount of cushioning agent 28 employed should be sufficient to completely cover surface 34 upon centrifugation. The amount of cushioning agent utilized can vary with the parameter of the particular system chosen, for example, the stopper design, volume of residual blood and volatility of the cushioning agent utilized. A preferred amount of cushioning agent can comprise from about 3.3% to about 40% by volume based on the volume of the cushioning agent-residual blood sample mixture which is removed from article 20 and tested for the presence of microbial pathogens.

Generally, the cushioning agent of the subject invention can comprise a high density, hydrophobic, water immiscible liquid. As noted previously, the term "high density" as used herein refers to a liquid which will not be supported by the mixture of blood and blood treating fluid or any other sample fluid suspected of containing microbial pathogens in the presence of centrifugal force. In addition, the cushioning agent should be non-toxic to microbial pathogens and relatively inert with respect to butyl rubber, silicone rubber and other types of elastomers employed in the manufacture of the injectable closure members described above. The density of the cushioning agent can be in the range of from about 1.2 grams per cubic centimeter to about 2.0 grams per cubic centimeter. Generally, fluorinated hydrocarbons having the above described characteristics and having molecular weights in the range of from about 300 to about 850 are preferred. Furthermore, fluorinated hydrocarbons having the above qualities which have a vapor pressure at 77° F. and 1 atmosphere from 0.06 psi (0.3 mm Hg) to about 0.58 psi (30 mm Hg) and preferably a vapor pressure approximately equal to that of water. Therefore, cushioning agents having the above described qualities and boiling points of about 200° F. to about 420° F. (93° C.–216° C.) and preferably of about 225° F. to about 280° F. (106° C. to 138° C.) can be utilized. The cushioning agents preferably have specific heat at least equal to or greater than 0.2 g-cal/g°c at 77° F. and 1 atmosphere, and most preferably specific heat at least equal to or greater than water. The cushioning agent should also have a vapor pressure which will not disrupt the injectable closure means from the tube during manufacturing steps such as autoclaving, for example. Fluorinated hydrocarbons sold under the trade name FLUORINERT by 3M Company of Minneapolis, Minnesota, have been found to perform well as cushioning agents. Specifically, types FC-75, FC-48, and FC-43 of the FLUORINERT series have been found to be especially useful.

Although the exact function which such cushioning agents perform is not fully known, it is believed that they improve collection of microbial pathogens which have passed from suspension in a centrifuged blood sample in at least two ways. First, the cushioning agent serves to seal interstitial spaces, cracks and crevices both on the smooth surface 34 of the centrifugation vessel 22 and the interface between the walls of the centrifugation vessel 22 and injectable closure member 26. Thus, microbial pathogens which might otherwise become entrapped in such interstitial spaces, and therefore not recovered, are recovered with the cushioning agent 28 when it is removed from article 20. Secondly, it is believed that the cushioning agent does act to cushion the impact of microbial pathogens which are forced out of suspension in a blood sample during centrifugation. This cushioning effect reduces the danger of injury to microbial pathogens which might otherwise occur upon impact. Further, while some of the microbial pathogens may actually pass into the cushioning agent, substantially none will pass completely through it and a majority will form on its surface at the interface between the cushioning agent 28 and the blood sample and collect in a layer.

After the cushioning agent 28 has been deposited within centrifugation article 20, the specimen transport system 30 for the blood may also be deposited there.

Once the specimen transport system 30 has been deposited in centrifugation article 20, injectable closure member 24 can be put in place and space 32 evacuated to the desired lower than atmospheric pressure, e.g., 25 to 30 inches of mercury. In accordance with one embodiment, the interior of centrifugation vessel 20 is next sterilized by a novel technique. It has been found that if a centrifugation vessel is heated to the vaporization point of the FLUORINERT material therewithin, e.g., at least about 120C and held for a sufficient time, e.g., at least about 30 minutes, the interior of the tube and the solid particulate specimen transport system 30 will become sterilized by the hot FLUORINERT vapors. Once this is done, the centrifugation vessel 20 is merely cooled to room temperature and packaged for sale, for example.

Now referring to FIGS. 2-9, an analysis sequence is schematically depicted illustrating a preferred embodiment of the subject invention. As an example, a procedure which is carried out in accordance with one embodiment of this invention for detection of microbial pathogens within a blood sample can be carried out conveniently with the following apparatus:

The above described centrifugation article 20 containing the cushioning agent 28 and specimen transport system 30. The vessel can be of 12-14 milliliters in volume.

A sterile glass syringe and one 1½ inch 21 gauge disposable hypodermic needle;

One sterile glass syringe and one 1 inch 18 gauge disposable hypodermic needle;

One ⅝ inch 25 gauge hypodermic needle with cotton inserted at its hub (used as a vent);

Two blood agar plates;

Two chocolate agar plates.

It is noted that with the exception of centrifugation article 20 or some equivalent article, various types of well-known laboratory apparatus and culture media can be used to carry out the novel process of the subject invention. It is particularly noted that the culture media set forth above are exemplary only and are generally preferred to be utilized for detecting the most commonly known microbial pathogens. The blood agar plates suggested are conventionally utilized blood agar plates which are basically sheep's blood and a base nutritional agent such as brain heart infusion, which is held together with an agar solidifying agent on a petri plate. The chocolate agar plate is designed to grow certain factitious pathogens, e.g., Hemophilus.

Thus, while various apparatus can be utilized in the method of the subject invention, the above list of apparatus and materials can be conveniently utilized in the scope of this invention in a manner set forth below.

To utilize centrifugation article 20 set forth in FIG. 1 in the drawing, it is initially positioned so that injectable closure member 26 with its smooth angled surface 34 is at the lower end of article 20 so that the cushioning agent 28 specimen transport system solids 30 rest upon smooth angled surface 34. In practice, a mixture of cushioning agent 28 and the solid articles of specimen transport system 30 may occur due to handling so that two distinct layers may not always be present. This unstable mixture of cushioning agent 28 and specimen transport system 30 in no way adversely affects the method set forth herein since the solids forming system 30 will rapidly dissolve in the aqueous sample (blood) and separation of the two resulting liquid phases rapidly occurs upon centrifugation.

Next, a predetermined amount of a blood sample 38 drawn from the patient, for example, 8 milliliters of blood, is injected into the evacuated space or centrifugation article 20 as depicted in FIG. 3 using a common type of syringe 40. Alternately, the sample can be drawn directly into article 20 using a standard and double needle fixture supplied with conventional vacuum blood drawing devices such as sold under the mark "Vacutainer" by Becton Dickinson. Then, article 20 containing the blood sample 38, the specimen transport system 30, and the cushioning agent 28 is subjected to mixing to insure that the anticoagulants, red cell lysing agent, and the specimen transport system 30 are completely admixed with the blood sample 38. This mixing step is depicted schematically by FIG. 4. The mixing step will insure that the specimen transport system 30 containing the lysing agent will be completely admixed with and solubilized by the blood sample. This solubilizing action will assure contact between antimicrobial factors and the chemical components of the specimen transport system 30 and thus assure that any pathogens contained within the blood sample 38 will be protected from antimicrobial activity.

After the blood sample 38 has been treated in this manner, centrifugation article 20 is centrifuged to cause the microbial pathogens within the treated blood sample 42 to pass out of suspension and collect adjacent the interface of the high density cushioning agent 28 and the residual of the sample fluid. Some microbial pathogens will actually be deposited upon the sidewall of centrifugation vessel 22 adjacent the high end of smooth surface 34 at point 22a. This centrifugation step is represented schematically by FIG. 5. The speed and time of centrifugation can vary widely depending upon the construction material of centrifugation article 20 and the type of centrifugation apparatus. The centrifugation can be conveniently accomplished by imparting from between about 1500 to 6000 gravities and preferably from about 1500 to 3000 gravities to the centrifugation article 20 containing he treated blood sample 42 and cushioning agent 28. As depicted in FIG. 5, an angle rotor centrifuge is employed which places the centrifugation article 20 at an angle of 56° for example, (depicted by arc 43) during centrifugation. Thus, if smooth angled surface 34 is at a 34° angle with respect to the interior walls of centrifugation article 20, the treated blood sample 42 and cushioning agent 28 will be forced against smooth angled surface 34 at a relatively perpendicular angle during centrifugation. It is noted that when a swinging bucket type of centrifuge is employed, centrifugation article 20 will be centrifuged at substantially 0° with respect to a horizontal surface. Thus, in such a case, the angle of surface 34 will be approximately 90° and an injectable rubber closure member having a flat inner surface can be substituted for injectable closure member 26.

Once the centrifugation step has been completed, centrifugation article 20 can be removed from the centrifuge and the major portion of the treated blood sample 42 from which microbial pathogens have been separated can be removed. It is noted that, as used herein, the term "residual treated blood" or "residual blood" refers to a blood sample which has been centrifuged such that the microbial pathogens present therein have collected at the bottom of the sample, hence, leaving the "residual" portion of the sample substantially free of microbial pathogens. This step is depicted in FIG. 6. To aid in ease of removal, a vent needle 44 in the form of a common hypodermic needle with cotton in its hub, for example, is injected through injectable closure member 24. A second hypodermic needle with syringe 45 attached can then be injected through injectable closure member 26 to remove a major portion of the residual treated blood sample 42 from which microbial pathogens have been separated. For example, when the centrifugation vessel has a volume of 5 from 12 to about 14 milliliters, a 1½ inch 18 gauge 1.7 milliliters of the treated blood sample 42. As shown, it is preferred that the major portion of the residual blood sample to be withdrawn from the interior of centrifugation vessel 22 is withdrawn at a point opposite the sidewall adjacent the upper bevel end of smooth surface 34 to avoid disturbing the layer of microbial pathogens which has formed on and within the interface of the two liquids and on the sidewall of centrifugation vessel 22 adjacent the upper end of said beveled smooth surface 34. The majority of the residual blood is removed in this step; however, a small portion of the residual blood should be left in the centrifugation vessel 22 such that of the total fluid remaining, the cushioning agent comprises from about 3.3% to about 40.0% by volume. It is preferred that no more than about 20% by volume shall be said cushioning agent because greater quantities of said cushioning agent may deleteriously effect the morphology of microbial pathogen colonies in subsequent pathogen growth steps used in the process.

Once the major portion of the treated residual blood sample has been removed, both needles may be withdrawn from injectable closure members 24 and 26, and centrifugation article 20 is then subjected to a second mixing step depicted schematically by FIG. 7. However, if desired, vent needle 44 can be left in its position through injectable closure member 24 to assist in removal of the pathogen containing fluid in a later step. The second mixing step serves to resuspend microbial pathogens which have separated from the major portion of residual treated blood sample 42 and which have formed the layer described above. Resuspension of the microbial pathogens so collected in the remaining minor portion of the residual treated blood sample 42 insures greater and more uniform recovery.

Once the mixing step has resuspended, the microbial pathogens in a minor portion of the residual treated blood sample 42, the mixture of microbial pathogens in the residual treated blood sample and the high density cushioning agent can be removed from centrifugation article 20. This step is depicted in FIG. 8. As noted above, if desired, the venting hypodermic needle 44 may be inserted through injectable closure member 24 to allow easier removal of the remaining constituents. The syringe 46 with attached hypodermic needle can then be injected through injectable closure member 26 to draw out the mixture 48 of cushioning agent 28, minor remaining portion of residual blood sample 42 and microbial pathogens present therein. It is noted that particularly good recovery can be obtained if the hypodermic needle used to remove these constituents is injected at the lower end of the angled smooth surface 34. It is believed that the angle of surface 34 acts, in part, as a funnel into which the remaining fluid containing the microbial pathogens flow. This mixture 48 of high density liquid cushioning agent 28, and the remaining minor portion of the residual treated blood sample 42 with the recovered microbial pathogens should be approximately 1½ milliliters of fluid. This fluid is then distributed on appropriate growth media. This step is then schematically illustrated in FIG. 9 in the drawing. With the apparatus set forth above, the material can be distributed as follows:

Two blood agar plates can receive 0.4 milliliters of the aqueous solution and can be incubated at 36° C. in an anaerobic environment. Two chocolate agar plates can receive 0.4 milliliters of the aqueous solution and can be incubated at 36° C. in a candle jar. The growth media should be checked daily for the presence of colonies. Microbiological analysis techniques can be employed. The number of microbial pathogens in one milliliter of the blood can be determined by multiplying the number of colonies by a correction factor. This correction factor takes into consideration the recovery rate for a given organism, the volumes of blood and high density cushioning agent employed and the amount of final mixture plated. In the general example set forth above, the correction factor is 0.5.

The above procedure will result in a dilution of the remaining minor portion of the residual treated blood sample 42 to at least about 1:60 on the growth media. This will assure that any residual quantity of the chemicals within the specimen transport system will be diluted sufficiently so as to not inhibit the growth of microbial pathogens therewithin. The specimen transport system of the subject invention will either neutralize or inhibit cidal drugs. For example, the sodium polyanetholsulfonate will generally neutralize and the cysteine will generally inhibit. Furthermore, the effect of oxygen on cysteine after removal of the sample from centrifugation vessel 22 will destroy its inhibiting effect on microorganisms. The above described dilution procedure may be necessary to dilute drugs and/or component of the specimen transport system to levels which are neither cidal nor inhibitory to the growth of microorganisms. In addition, for those antibiotics which may be present in the blood sample which exert only an inhibitory and not a cidal effect on microorganisms, the 1:60 dilution will generally prove adequate to reverse their inhibitory effect on microorganisms. An example of this class of compound is gantrisin. Thus, in genera, the 1:60 dilution will prevent the inhibiting of growth for most micro-organisms/antibiotic combinations. Nevertheless, there are certain microorganisms which are uniquely sensitive to the killing or inhibitory action of certain classes of antibiotics. For example, if one is attempting the isolation of a very sensitive strain of S. aureus (minimum inhibitory concentration of 0.2 micrograms per milliliter) and the blood sample contained 20 micrograms per milliliter of antibiotic not blocked by sodium polyanetholsulfonate, para-aminobenzoic acid, or cysteine-thioglycolate, the organism would not grow on a conventional agar plate (20 milliliters of media) in accordance with the above-described method which normally deposits 0.4 micrograms per milliliter of blood sample. This combination yields a final dilution of approximately 1:60. Thus, this example would yield a final concentration of 0.33 micrograms per milliliter of antibiotic throughout the plate which would indeed inhibit the subsequent growth of the *S. aureus* strain. Furthermore, the dilution of the antibiotic is not instantaneous and initially the high levels of the antibiotic on the surface of the agar plate might exert a lethal effect. To circumvent this problem and yet preserve the known advantages of the lysis-centrifugation technique improved with the novel specimen transport system of the subject invention, one further modification is required: namely, a big petri plate. Clinical laboratories concurrently use a 150 mm ×20 mm petri plate for testing antibiotics. This plate contains between 60 ml and 80 ml of media and has 2.25 times the surface area of a conventional 100 mm×20 mm petri plate. When one streaks the 0.4 ml blood sample uniformly on the surface of this large plate, one achieves a 2.25 fold increase in the diffusion rate and a final dilution between about 1:200 to about 1:270. In the example used above, this will result in a final antibiotic concentration of between 0.1 micrograms per milliliter and 0.075 micrograms per milliliter. When this plate is used, the final concentration of the antibiotic is well below the minimum inhibitory concentration and the organism should grow in normal fashion. Thus, while the large plate need not be used in each instance, it should be used when certain fastidious organisms-antibiotic combinations are suspected, such as *S. aureus*-cephalothin.

Figure 10:
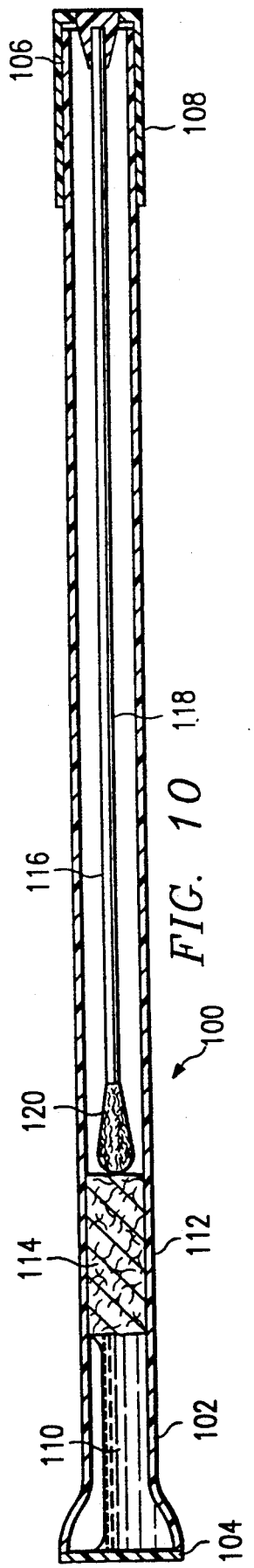
FIG. 10 depicts another embodiment of the subject invention which comprises a device for collecting and transporting body secretion samples.

Now referring to FIG. 10, another embodiment of the subject invention is depicted which comprises a device for collecting and transporting body secretion samples. Device 100 comprises an elongated flexible tube 102 enclosed at one end 104 and open at its opposite end 106. Cap 108 encloses the open end. Contained within the tube near closed end 104 is a crushable ampule 110 containing a suitable liquid growth media for microbial pathogens. Disposed adjacent ampule 110 is sorbent material 112 which can be any suitable sorbent such as cotton. Sorbent material 112 contains dispersed therein specimen transport system solids 114. Disposed within the open end of tube 106 is swab member 116 which comprises a handle 118 and an absorbent tip 120 for recovering body secretions from a lesion, for example.

Specimen transport system solids 114 can be the same material disclosed for use in the lysis-centrifugation vessel described above and can be present in the same relative quantities based upon the amount of solids 114 and growth media 110 and body secretion collected on absorbent tip 120 as the components described above in relation to a blood sample. In operation, cap 106 is removed and swab 116 is removed from the interior of tube 102. The swab contacts body secretion from an open lesion, for example, and is inserted again within the interior of tube 102 and cap 108 is placed over the open end 106 thereof. Thereafter, the portion of tube 102 adjacent closed end 104 is squeezed and ampule 110 is ruptured to cause the liquid growth to be released therefrom and saturate sorbent material 112 and solubilize specimen transport system solids 114. The resulting liquid containing the dissolved specimen transport system is absorbed by the tip of swab 120 and provides a media for sustaining microbial pathogens present on the tip and also an specimen transport system for deactivating antimicrobial factors which might be present in the body secretions sorbed on the tip 120 of swab 116. The swab 116 is later removed from container 102 and mirobiologically analyzed in a manner described above.

The following additional examples are given to better facilitate the understanding of this invention and are not intended to limit the scope thereof. In Examples VII-XVI:

CFU = Colony-forming units of a microorganism/ml of blood initially inoculated into the tube. Seven and one-half ml of blood are processed per tube.

% Recovery = Percentage of organism recovered in the gradient of all organisms found after processing.

S-Factor = Survival index = Number of CFU recovered from all contents in tube/number of CFU introduced: S = 1 means no kill; S = 0.1 means 10% survival

EXAMPLE VII

Action of Sodium Polyanetholsulfonate (SPS) on Gentamincin

Tests were made comprising the original centrifugation article disclosed and claimed in U.S. Pat. No. 4,212,948. In the original version, each tube contains 0.3 ml of FLUORINERT FC48 as cushioning agent and as a blood treating fluid 0.5 milliliters of distilled water containing 0.005 milliliters PPG, 0.008 grams of EDTA and 0.0048 grams of SPS together with 0.018 grams of purified saponin as a lysing agent. The tube was sterile with the aqueous solution having a pH of 7.4 and sufficient vacuum to draw approximately 7.5 milliliters of human blood. A second type tube was prepared except sodium polyanetholsulfonate was added to the aqueous solution in an amount to equal 0.6% by weight of the final concentration of treating fluid and blood sample. Next a series of the above described original tubes and the original tubes plus the sodium polyanetholsulfonate were tested by adding known quantities of *Staphylococcus aureus* in a blood sample containing 6 micrograms per milliliter of gentamicin. Blood was lysed, the tubes were held at room temperature (approximately 72° F.) for 2 hours prior to centrifugation to simulate clinical conditions. Thereafter the tubes were centrifuged as described above and the concentrated material plated on growth media and tested for recovery. The results are set forth below.

TABLE VII-1

| SYSTEM | *Staphylococcus aureus* (ATCC 25923) Gentamicin (6 ug/ml) | | |
|---|---|---|---|
| | CFU | % RECOVERY | S FACTOR |
| Original | 133 | 100 | .06 |
| Original + 0.6 SPS | 203 | 80 | .9 |

The original tube gave an overall recovery of 6% while the SPS system gave a recovery of 72% (11.0 fold improvement).

EXAMPLE VIII

Deactivation of Ampicillin by Thioglycolate

This example was carried out in the same fashion as Example VI except the stated quantities of thiogycolate were added to the second and third series of tubes.

TABLE VIII-1

Staphylococcus aureus (ATCC 25923)
Ampicillin (21 ug/ml)

| SYSTEM | CFU | % RECOVERY | S FACTOR |
|---|---|---|---|
| Original | 196 | 33 | .002 |
| Original + 1% thioglycolate* | 490 | 89 | .040 |
| Original + 6% thioglycolate | 466 | 89 | .13 |

*Amount of thioglycolate based upon treating fluid and blood sample.

The original tube gave an overall recovery of 0.07% recovery versus 12.5% for the 6% thioglycolate system—a 179 fold improvement.

EXAMPLE IX

Deactivation of Ampicilin and Gentamicin By a Novel Cysteine-Thioglycolate Combination The series of runs set forth below were carried out in the same fashion as Example VII above except with the quantity and amount of antibiotic and the stated quantities of thioglycolate-cysteine which were added to the liquid blood treating material.

TABLE IX-1

Staphylococcus aureus (ATCC 25923)
Ampicillin (21 ug/ml)

| SYSTEM | CFU | % RECOVERY | S FACTOR |
|---|---|---|---|
| Original | 196 | 33 | .002 |
| Original + 0.5% thioglycolate* + 0.2% cysteine* | 245 | 98 | 0.80 |
| Original + 0.1% thioglycolate* + 1.2% cysteine* | 696 | 99 | 1.1 |

*Amounts based upon total quantity of treating fluids and blood sample.

TABLE IX-2

Staphylococcus aureus (ATCC 25923)
Gentamicin (6 ug/ml)

| SYSTEM | CFU | % RECOVERY | S FACTOR |
|---|---|---|---|
| Original | 133 | 100 | .1 |
| Original + .5% thioglycolate* | 203 | 100 | .2 |
| Original + .5% thioglycolate* + .2% cysteine* | 287 | 86 | .8 |

*Amounts based upon total quantity of treating fluid and blood sample.

The comparative data in Tables IX-1 and IX-2 above clearly demonstrate the use of the thioglycolate-systeine combination.

EXAMPLE X

Synergistic Action of Thioglycolate-Cysteine Mixture in Lowering Viscosity of Lysed Human Blood In each instance, 7.5 milliliters of human blood was treated with an aqueous solution containing 2.5% by weight purified saponin and quantities, if any, of thioglycolate and cysteine as illustrated in the table (based upon the total quantity of treating fluid and blood). The viscosity of each sample was measured at the temperature between 23.5° and 24.8° C. The results are set forth below:

TABLE X-1

| TREATMENT (Saponin-2.5%) | VISCOSITY (Centistokes) |
|---|---|
| 1. Saponin x1 | 4.04 |
| 2. Saponin x1 + 0.1% thioglycolate | 7.28 |
| 3. Saponin x1 + 0.5% thioglycolate | 7.77 |
| 4. Saponin x1 + 1.0% thioglycolate | 8.56 |
| 5. Saponin x1 + 2.0% thioglycolate | 8.51 |
| 6. Saponin x1 + 3.0% thioglycolate | 8.46 |
| 7. Saponin x1 + 0.1% cysteine | 4.56 |
| 8. Saponin x1 + 0.5% cysteine | 3.46 |
| 9. Saponin x1 + 1.0% cysteine | 2.89 |
| 10. Saponin x1 + 1% thioglycolate + 0.1% cysteine | 5.14 |
| 11. Saponin x1 + 1% thioglycolate + 0.5% cysteine | 4.30 |
| 12. Saponin x1 + 1% thioglycolate + 1.0% cysteine | 3.75 |
| 13. Saponin x1 + 1% thioglycolate + 2.0% cysteine | 3.43 |
| 14. Saponin x1 + 3% thioglycolate + 0.1% cysteine | 6.28 |
| 15. Saponin x1 + 3% thioglycolate + 0.5% cysteine | 4.58 |
| 16. Saponin x1 + 3% thioglycolate + 1.0% cysteine | 3.44 |
| 17. Saponin x1 + 3% thioglycolate + 1.5% cysteine | 3.82 |

Temperature of samples were between 23.5° C.–24.8° C.

EXAMPLE XI

Effect of Specimen Transport System in Improving Blood Specimen Microbial Integrity The data in the following tables illustrate the following important aspects of the invention, namely:

1. In the presence of average serum levels of different antibiotics the original system can lose up to 99.7% of the original inoculum Staphylococcus aureus with ampicillin). For S. aureis 13 of 19 antibiotics killed 50% or more of organism within two hours. For Escherichia coli this excessive cidal action occurred with nine of the antibiotics. (See Tables XI-1 and XI-2).

2. With the new system, the highest kill rate was 70% and a reduction of the inoculum to 50% or less occurred with two antibiotics for S. aureus and two with E. coli. By adding large plates to the new device, the cidal effect observed in these four cases can be virtually eliminated (S=0.8 versus 0.3; S=0.9 versus 0.5; S=0.8 versus 0.5 and S=0.5 versus 0.3, where 5=1.00=100% survival).

In summary, the new system in conjunction with effective dilution (i.e. the use of large petri plates) is capable of effectively blocking the cidal action of blood and therapeutic antibiotics upon the bacteria present in a blood sample during transport and processing.

The data presented in Tables XI-3 through XI-10 below confirm the general effectiveness of this invention on other pathogens commonly isolated from the blood of patients suffering from septicemia.

The procedure set forth below was followed for each pathogen, using various antibiotics. Concentrated residue from each tube was plated on both small and large plates to generate the data illustrated.

A series of original lysis-centrifugation devices were assembled as described in Example VII. A second series of lysis-centrifugation devices were assembled as in Example VII with the exception that the aqueous phase was modified as follows:

0.5 milliliters of distilled water containing 0.005 milliliters of polypropylene glycol was placed into the tubes.

A total of 0.17 grams of powdered mixture was then added to each tube. The mixture contained the following components:

1.8 grams of purified saponin, 4.8 grams of sodium polyanetholsulfonate, 0.8 grams of thioglycolate, and 9.6 grams of cysteine.

The tubes were sterilized by autoclaving and had a final pH of between 6.6 and 6.8.

Sufficient vacuum was placed in the tube to draw 7.5 milliliters of blood.

In each instance, the stated amount of specific microorganism as illustrated in tables below and antibiotic was added to 7.5 milliliters of blood. The blood was then deposited into the lysis-centrifugation tube and the tube was held at room temperature for 2 hours to simulate clinical conditions, and thereafter was subjected to centrifugation as described in this specification. The concentrated residue in each tube was then plated in equal aliquots on five agar plates containing appropriate growth media which had dimensions of 100 milliliters × 20 milliliters and growth was observed. One milliliter of the supernatant remaining after centrifugation was also plated on the five plates.

TABLE XI-1

| ANTIBIOTICS*** | ORIGINAL SMALL PLATES | | | IMPROVED SMALL PLATES | | |
|---|---|---|---|---|---|---|
| | CFU | % RECOVERY | S FACTOR | CFU | % RECOVERY | S FACTOR |
| I. *Staphylococcus aureus* (ATCC #25923) | | | | | | |
| No Drug | 75 | 91 | .9 ± .2 | 745 | 99 | 1.1 ± .2 |
| Gentamicin (6) | 133 | 100 | .1 ± .04 | 852 | 99 | 1.0 ± .1 |
| Tobramycin (4) | 155 | 99 | .4 ± .2 | 259 | 95 | .8 ± .2 |
| Amikacin (21) | 76 | 99 | 1.0 ± .3 | 152 | 99 | 1.1 ± .2 |
| Penicillin (20) | 546 | 68 | .01 ± .01 | 305 | 96 | .9 ± .2 |
| Ampicillin (21) | 403 | 84 | .003 ± .003 | 319 | 94 | 1.0 ± .1 |
| Cephalothin (20) | 214 | 100 | .1 ± .03 | 1177 | 76 | .3 ± .3 |
| Cefoxitin (25) | 158 | 98 | .5 ± .1 | 991 | 99 | .6 ± .2 |
| Chloramphenicol (18) | 476 | 99 | .6 ± .2 | 495 | 99.8 | 1.1 ± .3 |
| Tetracycline (9) | 218 | 100 | .5 ± .4 | 584 | 100 | 1.2 ± .1 |
| Erythromycin (8) | 512 | 100 | .1 ± .05 | 623 | 72 | .8 ± .2 |
| Gantrisin (100) | 642 | 93 | 1.0 ± .2 | 441 | 99.7 | 1.0 ± .1 |
| Clindamycin (5) | 180 | 99.7 | 1.2 ± .9 | 123 | 78 | 1.3 ± .4 |
| Methicillin (9) | 588 | 99.8 | .9 ± .1 | 408 | 92 | 1.1 ± .3 |
| Vancomycin (8) | 286 | 98 | .6 ± .1 | 1190 | 52 | .8 ± .2 |
| Piperacillin (60) | 350 | 82 | .005 ± .007 | 396 | 99 | 1.2 ± .1 |
| Moxalactam (100) | 676 | 100 | .2 ± .03 | 2345 | 49 | 1.2 ± .4 |
| Carbenicillin (71) | 483 | 100 | .03 ± .02 | 438 | 99.8 | 1.1 ± .3 |
| Cefotaxime (20) | 472 | 99 | .3 ± .1 | 595 | 98 | .5 ± .2 |
| Ticarcillin (150) | 606 | 50 | .01 ± .01 | 553 | 98 | .9 ± .1 |
| II. *Excherichia coli* (ATCC #25922) | | | | | | |
| No Drug | 214 | 98 | 1.2 ± .3 | 886 | 95 | 1.1 ± .2 |
| Gentamicin (6) | 468 | 100 | .02 ± .01 | 167 | 97 | 1.1 ± 1.0 |
| Tontamycin (4) | 129 | 100 | .6 ± .6 | 399 | 99 | .9 ± .2 |
| Amikacin (21) | 255 | 100 | .05 ± .03 | 420 | 98 | .8 ± .1 |
| Penicillin (20) | 526 | 99 | 1.4 ± .3 | 206 | 95 | 1.3 ± .3 |
| Ampicillin (21) | 490 | 100 | .2 ± .1 | 144 | 98 | .9 ± .2 |
| Cephalothin (20) | 413 | 100 | .04 ± .04 | 353 | 99 | .5 ± .1 |
| Cefoxitin (25) | 466 | 99 | .3 ± .06 | 148 | 89 | .8 ± .3 |
| Chloramphenicol (18) | 323 | 99 | .8 ± .1 | 395 | 99.6 | .7 ± .3 |
| Tetracycline (9) | 368 | 99 | .5 ± .04 | 320 | 98 | 1.1 ± .2 |
| Erythromycin (8) | 305 | 99 | 1.0 ± .4 | 212 | 97 | 1.1 ± .3 |
| Gantrisin (100) | 140 | 99 | 1.5 ± 1.0 | 282 | 97 | .8 ± .3 |
| Ticarcillin (150) | 574 | 99.8 | .5 ± .4 | 651 | 99 | 1.3 ± .7 |
| Carbenicillin (20) | 1694 | 99.6 | .2 ± .1 | 417 | 98 | 1.0 ± .2 |
| Piperacillin (60) | 364 | 100 | .7 ± .4 | 1084 | 96 | .9 ± .2 |
| Cefamandole (20) | 167 | 99.5 | .4 ± .2 | 153 | 100 | .7 ± .4 |
| Kanamycin (14) | 203 | 100 | .1 ± .03 | 176 | 95 | .3 ± .1 |
| Methicillin (9) | 198 | 99.8 | 1.1 ± .2 | 146 | 99 | 1.1 ± .3 |

All tubes were held at room temperature (20 C.) for two hours prior to processing.
The small plates contained 20 ml of agar media.
***Numbers in parenthesis represent final concentration of antibiotic used in microorganisms/ml of blood.

The above experiments were repeated except instead of the 100 milliliter by 20 milliliter petri plates containing media, the concentrated residue from each tube was plated on a 150 milliliter by 20 milliliter petri plate which contains between 60 milliliters and 80 milliliters of media and had approximately 2.25 times the surface area of 100 milliliter by 20 milliliter petri plate described which were used to generate the data in Table XI-1 above. The results are set forth in Table XI-2 below.

TABLE XI-2

| ANTIBIOTICS*** | ORIGINAL SMALL PLATES | | | IMPROVED SMALL PLATES | | |
|---|---|---|---|---|---|---|
| | CFU | % RECOVERY | S FACTOR | CFU | % RECOVERY | S FACTOR |
| I. *Staphylococcus aureus* (ATCC #25923) | | | | | | |
| No Drug | + | + | + | + | + | + |

TABLE XI-2-continued

| | ORIGINAL SMALL PLATES | | | IMPROVED SMALL PLATES | | |
|---|---|---|---|---|---|---|
| ANTIBIOTICS*** | CFU | % RECOVERY | S FACTOR | CFU | % RECOVERY | S FACTOR |
| Gentamicin (6) | + | + | + | 630 | 92 | .7 ± .2 |
| Tobramycin (4) | + | + | + | + | + | + |
| Amikacin (21) | + | + | + | + | + | + |
| Penicillin (20) | + | + | + | + | + | + |
| Ampicillin (21) | + | + | + | + | + | + |
| Cephalothin (20) | 214 | 100 | .4 ± .2 | 777 | 100 | .8 ± .1 |
| Cefoxitin (25) | 467 | 96 | .7 ± .2 | 301 | 99.8 | .9 ± .1 |
| Chloramphenicol (18) | + | + | + | + | + | + |
| Tetracycline (9) | 266 | 100 | .3 ± .3 | 581 | 99 | .8 ± .1 |
| Erythromycin (8) | 512 | 100 | .9 ± .2 | 375 | 100 | .6 ± .2 |
| Gantrisin (100) | + | + | + | + | + | + |
| Clindamycin (5) | + | + | + | + | + | + |
| Methicillin (9) | + | + | + | + | + | + |
| Vancomycin (8) | + | + | + | + | + | + |
| Piperacillin (60) | + | + | + | + | + | + |
| Moxalactam (100) | + | + | + | + | + | + |
| Cefotaxime (20) | 564 | 100 | .8 ± .1 | 567 | 100 | .9 ± .1 |
| II. *Escherichia coli* (ATCC #29522) | | | | | | |
| No Drug | 237 | 91 | 1.3 ± .3 | 172 | 94 | 1.5 ± .6 |
| Gentamicin (6) | + | + | + | + | + | + |
| Tobramycin (4) | + | + | + | + | + | + |
| Amikacin (21) | + | + | + | + | + | + |
| Penicillin (20) | + | + | + | + | + | + |
| Ampicillin (21) | + | + | + | + | + | + |
| Cephalothin (20) | 102 | 100 | .1 ± .09 | 288 | 92 | .8 ± .1 |
| Cefoxitin (25) | 454 | 100 | .5 ± .1 | 406 | 99 | .9 ± .3 |
| Chloramphenicol (18) | 217 | 99.5 | 1.0 ± .3 | 420 | 96 | 1.1 ± .4 |
| Tetracycline (9) | + | + | + | + | + | + |
| Erythromycin (8) | 305 | 100 | .9 ± .2 | 212 | 99 | 1.0 ± .2 |
| Gantrisin (100) | 140 | 99.8 | 1.4 ± .6 | 231 | 99 | 1.0 ± .1 |
| Ticarcillin (150) | + | + | + | + | + | + |
| Carbenicillin (20) | + | + | + | + | + | + |
| Piperacillin (60) | + | + | + | + | + | + |
| Cefamandole (20) | 167 | 99 | .5 ± .2 | 209 | 98 | .8 ± .1 |
| Kanamycin (14) | 330 | 100 | .05 ± .03 | 352 | 99.6 | .5 ± .2 |

All tubes were held at room temperature (20 C.) for two hours prior to processing.
The large plates contained 80 ml of agar media.
***Numbers in parenthesis represent final concentration of antibiotic used in microorganisms/ml of blood.
+ Not tested because recovery is good on small plates.

TABLE XI-3

ENTEROBACTER CLOACAE

| | % Recovery | | S-Factor | |
|---|---|---|---|---|
| | Old | New | Old | New |
| #1344-2 - SMALL PLATES | | | | |
| Ampicillin | 99.5 | 95 | 1.5 ± .5 | .8 ± .1 |
| Carbenicillin | 0 | 94 | 0 | .6 ± .3 |
| Ticarcillin | 100 | 86 | .06 ± .07 | 1.3 ± .6 |
| Tobramycin | 100 | 75 | .03 ± .01 | .9 ± .2 |
| Chloramphenicol | 98 | 80 | .9 ± .2 | 1.2 ± .3 |
| Tetracycline | 98 | 88 | .9 ± .5 | 1.4 ± .7 |
| Gantrisin | 97 | 99 | .6 ± .1 | .8 ± .1 |
| No Drug | 97 | 98 | 1.4 ± .2 | 1.2 ± .1 |
| Cefoxitin | 95 | 97 | .9 ± .2 | .8 ± .2 |
| Cephalothin | 99.6 | 88 | 1.0 ± .2 | .9 ± .1 |
| Gentamicin | 95 | 99 | .04 ± .03 | 1.1 ± .1 |
| LARGE PLATES | | | | |
| Tetracycline | 97 | 96 | .7 ± .1 | .9 .2 |
| Tobramycin | 88 | 93 | .9 ± .5 | 1.1 .2 |
| Chloramphenicol | + | 97 | + | .9 .3 |

+ Not tested because recovery is good on small plates.

TABLE XI-4

KLEBSIELLA PNEUMONIAE

| | % Recovery | | S-Factor | |
|---|---|---|---|---|
| | Old | New | Old | New |
| #632-2 - SMALL PLATES | | | | |
| Ampicillin | 97 | 93 | .5 ± .3 | 1.0 ± 1 |
| Carbenicillin | 93 | 94 | .1 ± .1 | .8 ± .2 |
| Ticarcillin | 99 | 89 | 1.0 ± .1 | .9 ± .1 |

TABLE XI-4-continued

KLEBSIELLA PNEUMONIAE

| | % Recovery | | S-Factor | |
|---|---|---|---|---|
| | Old | New | Old | New |
| Tobramycin | 85 | 93 | .3 ± .3 | 1.1 ± .2 |
| Chloramphenicol | 99 | 93 | 1.3 ± .2 | 1.0 ± .4 |
| Tetracycline | 98 | 95 | 1.0 ± .1 | .9 ± .2 |
| Gantrisin | 95 | 98 | 1.0 ± .1 | .9 ± .1 |
| Cefoxitin | 49 | 97 | .02 ± .02 | 1.0 ± .1 |
| No Drug | 92 | 93 | 1.1 ± .3 | .7 ± .1 |
| Cephalothin | 100 | 98 | .2 ± .1 | .5 ± .2 |
| Gentamicin | 90 | 99 | .02 ± .01 | .9 ± .2 |
| LARGE PLATES | | | | |
| Carbenicillin | 92 | 88 | .5 ± .3 | .7 .2 |

TABLE XI-5

PSEUDOMONAS AERUGINOSA
27853 - SMALL PLATES

| | % Recovery | | S-Factor | |
|---|---|---|---|---|
| | Old | New | Old | New |
| Ampicillin | 97 | 94 | .6 ± .4 | .8 ± .2 |
| Carbenicillin | 98 | 95 | .9 ± .3 | .9 ± .1 |
| Ticarcillin | 93 | 91 | .3 ± .1 | 1.2 ± .1 |
| Tobramycin | 98 | 90 | 1.0 ± .1 | .9 ± .2 |
| Chloramphenicol | 96 | 86 | .7 ± .2 | 1.1 ± .2 |
| Tetracycline | 95 | 89 | 1.0 ± .1 | 1.2 ± .1 |
| Gantrisin | 99 | 98 | 1.2 ± .2 | .9 ± .1 |
| No Drug | 97 | 97 | 1.6 ± .3 | .9 ± .2 |
| Cefotaxime | 99 | 96 | .9 ± .2 | 1.1 ± .3 |
| Cefoxitin | 97 | 86 | 1.4 ± .2 | .9 ± .4 |

TABLE XI-5-continued

PSEUDOMONAS AERUGINOSA #27853 - SMALL PLATES

|  | % Recovery | | S-Factor | |
| --- | --- | --- | --- | --- |
|  | Old | New | Old | New |
| Cephalothin | 90 | 92 | 1.4 ± .1 | 1.4 ± .01 |
| Gentamicin | 98 | 56 | 1.0 ± .4 | 1.2 ± .2 |
| Moxalactam | 97 | 87 | .6 ± .1 | .9 ± .1 |

TABLE XI-6

STREPTOCOCCUS PNEUMONIAE

|  | % Recovery | | S-Factor | |
| --- | --- | --- | --- | --- |
|  | Old | New | Old | New |
| #6301 - SMALL PLATES | | | | |
| Penicillin | 76 | 63 | .02 ± .16 | .8 ± .2 |
| Ampicillin | 43 | 65 | .01 ± .01 | .6 ± .2 |
| Methicillin | 83 | 86 | .003 ± .004 | .4 ± .2 |
| Tobramycin | 97 | 88 | .8 ± .4 | .6 ± .4 |
| Chloramphenicol | 99 | 93 | .6 ± .4 | .8 ± .2 |
| Tetracycline | 100 | 99 | .3 ± .2 | .4 ± .2 |
| Erythromycin* | 97 | 98 | .3 ± .3 | 1.3 ± .3 |
| Cefoxitin | 97 | 99 | .4 ± .1 | .5 ± .2 |
| No Drug | 93 | 90 | 1.0 ± .03 | 1.0 ± .1 |
| Gentamicin | 99.8 | 100 | 1.0 ± .1 | 1.1 ± .1 |
| LARGE PLATES | | | | |
| Tetracycline | 99 | 100 | .5 ± .2 | .7 ± .2 |
| Tobramycin | 98 | 99 | 1.0 ± .3 | 1.1 ± .2 |
| Ampicillin | + | 82 | + | .9 ± .3 |
| Cefoxitin | 100 | 99 | .2 ± .1 | .8 ± .1 |
| Methicillin | + | 97 | + | .6 ± .1 |
| Penicillin | + | 63 | | .9 ± .1 |

*Incubation period - 48 hours.
+ Not tested because recovery is good on small plates.

TABLE XI-7

STREPTOCOCCUS PYOGENES

|  | % Recovery | | S-Factor | |
| --- | --- | --- | --- | --- |
|  | Old | New | Old | New |
| #19615 - SMALL PLATES | | | | |
| Penicillin | 0.2 | 100 | .02 ± .02 | .6 ± .2 |
| Ampicillin | 0 | 99 | .0002 ± .000 | 3.6 ± .1 |
| Methicillin | 95 | 90 | .2 ± .1 | .8 ± .2 |
| Tobramycin | 98 | 100 | .6 ± .1 | .5 ± .2 |
| Chloramphenicol | 98 | 97 | .5 ± .1 | .4 ± .2 |
| Tetracycline | 100 | 96 | .3 ± .1 | .1 ± .1 |
| Erythromycin | 100 | 100 | .02 ± .01 | .02 ± .01 |
| Cefoxitin | 98 | 100 | .3 ± .1 | .2 ± .03 |
| No Drug | 92 | 95 | 1.0 ± .5 | .5 ± .1 |
| Gentamicin | 99 | 94 | .6 ± .1 | .9 ± .1 |
| LARGE PLATES | | | | |
| Methicillin | 99 | 99.8 | .6 ± .1 | 1.7 ± .2 |
| Tobramycin | 99 | 100 | 1.0 ± .3 | 1.1 ± .3 |
| Chloramphenicol | 99 | 99 | .8 ± .3 | .9 ± .3 |
| Tetracycline | 99.6 | 100 | .6 ± .1 | .7 ± .3 |
| Erythromycin | 100 | 100 | .1 ± .1 | .1 ± .1 |
| Cefoxitin | 98 | 95 | .6 ± .1 | .7 ± .2 |
| No Drug | 98 | 97 | .8 ± .1 | 1.0 ± .2 |
| Ampicillin | + | 100 | + | 1.5 ± .2 |
| Gentamicin | + | 99.5 | + | 1.2 ± .3 |

TABLE XI-8

HAEMOPHILUS INFLUENZAE

|  | % Recovery | | S-Factor | |
| --- | --- | --- | --- | --- |
|  | Old | New | Old | New |
| #19418 - SMALL PLATES | | | | |
| No Drug | 89 | 78 | .6 ± .2 | .9 ± .4 |
| Ampicillin | 33 | 95 | .01 ± .01 | .9 ± .1 |
| Cefoxitin | 80 | 97 | .1 ± .1 | .7 ± .2 |
| Clindamycin | 96 | 99 | 1.2 ± .2 | 1.1 ± .2 |
| Erythromycin | 94 | 100 | .4 ± .1 | .7 ± .2 |
| Gentamicin | 90 | 77 | .4 ± .1 | 1.3 ± .4 |
| Kanamycin | 94 | 99 | .8 ± .1 | .9 ± .1 |

TABLE XI-8-continued

HAEMOPHILUS INFLUENZAE

| Methicillin | 94 | 99 | .9 ± .2 | .8 ± .1 |
| --- | --- | --- | --- | --- |
| Penicillin | 73 | 99 | .1 ± .1 | .6 ± .1 |
| Tetracycline | 100 | 99 | .2 ± .1 | .6 ± .1 |
| Vancomycin | 95 | 99 | .7 ± .2 | .8 ± .2 |
| LARGE PLATES | | | | |
|  | % Recovery | | S-Factor | |
|  | Old | New | Old | New |
| No Drug | 95 | 99 | .9 ± .1 | 1.2 ± .1 |
| Cefoxitin | 93 | 95 | .8 ± .6 | .7 ± .2 |
| Gantrisin | 92 | 98 | 1.2 ± .7 | .6 ± .1 |
| Penicillin | 100 | 99 | .3 ± .2 | .6 ± .2 |

TABLE XI-9

BACTEROIDES FRAGILIS #23745 - SMALL PLATES

|  | % Recovery | | S-Factor | |
| --- | --- | --- | --- | --- |
|  | Old | New | Old | New |
| No Drug | 88 | 51 | .7 ± .2 | 1.0 ± .3 |
| Carbencillin | 96 | 82 | .09 ± .05 | .5 ± .1 |
| Cefotaxime | 97 | 100 | .7 ± .2 | .8 ± .1 |
| Cefoxitin | 94 | 99 | .5 ± .3 | 1.1 ± .5 |
| Chloramphenicol | 87 | 88 | .9 ± .2 | .9 ± .1 |
| Erythromycin | 98 | 64 | .7 ± .5 | .6 ± .2 |
| Penicillin | 87 | 51 | .7 ± .1 | .7 ± .1 |
| Tetracycline | 90 | 90 | .5 ± .1 | .5 ± .1 |
| Vancomycin | 95 | 99 | .7 ± .2 | .8 ± .2 |

TABLE XI-10

CLOSTRIDIUM SPOROGENES #19404 - SMALL PLATES

|  | % Recovery | | S-Factor | |
| --- | --- | --- | --- | --- |
|  | Old | New | Old | New |
| No Drug | 97 | 93 | .6 ± .1 | .6 ± .2 |
| Carbenicillin | 98 | 99 | .3 ± .3 | .8 ± .3 |
| Cefotaxime | 97 | 98 | .5 ± .2 | .5 ± .2 |
| Chloramphenicol | 96 | 97 | .7 ± .4 | .6 ± .4 |
| Clindamycin | 99.7 | 100 | .4 ± .2 | .3 ± .2 |
| Erythromycin | 96 | 99 | .5 ± .2 | .8 ± .2 |
| Gantrisin | 93 | 99 | .5 ± .1 | .7 ± .1 |
| Gentamicin | 98 | 98 | .8 ± .2 | .6 ± .4 |
| Penicillin | 100 | 96 | .08 ± .04 | .8 ± .3 |

Once again a new cocktail protected the microorganisms from the cidal effect of the antibiotics. As expected for those antibiotics which do not exert a cidal effect, both the original tube and the modified tube containing the specimen transport system yielded the same actual recovery of microorganisms. A large dilution is apparently needed (1:267) when dealing with a few specific organism-antibiotic combinations, e.g., S. aureus with cephalothin. These data suggest that large dilutions will only be required for a few antibiotics, e.g., cephalothin, tetracycline, erythromycin, and certain organisms, e.g., +cocci. The aminoglycosides, penicillin, ampicillin, and chloramphenicol are completely neutralized by the cocktail while the cephalothins are partially neutralized.

EXAMPLE XII

A series of the original tubes as described in Example XI and the tubes containing the specimen transport system as described in Example XI were utilized to process blood from patients suspected of having septicemia with confirmed positive blood cultures. In each case, blood from the patient was placed in the original tube and the modified tube containing the specimen transport system. The tubes were centrifuged and the concentrated residue plated on the small petri plates described in Example XI. The results of the tests are set forth in Table XII-1 below.

A third series of lysis-centrifugation devices were assembled as follows:

To the article as disclosed in U.S. Pat. No. , 4,212,948 were added 0.3 milliliters of FLUORINERT FC48 as

TABLE XII-1

| CULTURE NO. | ORGANISM | COUNT/ML ORIGINAL SYSTEM | COUNT/ML NEW SYSTEM | % OF CHANGE | ANTIBIOTIC IN SERUM AT TIME OF DRAW |
|---|---|---|---|---|---|
| 1. | Acinetobacter sp. | NG* | 1.4 | — | None |
| 2. | Enterobacter agglomerans | 0.7 | 0.7 | 0 | None |
| 3. | Enterobacter cloacae | 0.1 | NG | — | Tobramycin & Cefazolin |
| 4. | Enterobacter cloacae | NG | 0.1 | — | Cefoxitin |
| 5. | Escherichia coli | 0.6 | 2.9 | +383 | Penicillin & Tobramycin |
| 6. | Escherichia coli | 1.1 | .7 | −57 | Penicillin & Tobramycin |
| 7. | Escherichia coli | 13.0 | 92.8 | +614 | None |
| 8. | Escherichia coli | 7.3 | 12.5 | +71 | Ticarcillin & Gentamicin |
| 9. | Escherichia coli | 2.1 | 10.2 | +385 | None |
| 10. | Escherichia coli | NG | 0.1 | — | Mefoxin |
| 11. | Escherichia coli | NG | 0.1 | — | Penicillin & Tobramycin |
| 12. | Flavobacterium | NG | 0.6 | — | — |
| 13. | Histoplasma capsulatum | 10.5 | 7.0 | −50 | Amphotericin B |
| 14. | Histoplasma capsulatum | 1.6 | 2.6 | +62 | Amphotericin B |
| 15. | Histoplasma capsulatum | 13.5 | 14.2 | +05 | Amphotericin B |
| 16. | Klebsiella oxytoca | 8.8 | 20.6 | +134 | None |
| 17. | Klebsiella oxytoca | 2.1 | 3.9 | +86 | Gentamicin & Ticarcillin |
| 18. | Klebsiella pneumoniae | 0.1 | 0.1 | — | Gentamicin |
| 19. | Klebsiella pneumoniae | 11.9 | 19.3 | +62 | Tobramycin & Carbenicillin |
| 20. | Klebsiella pneumoniae | 130.8 | 78.1 | −67 | None |
| 21. | Klebsiella pneumoniae | 163.0 | 182.0 | +12 | Tobramycin & Carbenicillin |
| 22. | Klebsiella pneumoniae | 0.3 | NG | — | Tobramycin & Carbenicillin |
| 23. | Klebsiella pneumoniae | 0.3 | 1.0 | +227 | Gentamycin & Ticarcillin |
| 24. | Klebsiella pneumoniae | 7.3 | 8.4 | +15 | Gentamycin & Ticarcillin |
| 25. | Listeria monocytogenes | 0.4 | 9.5 | +227 | Cefoxitin |
| 26. | Pseudomonas aeruginosa | 131.3 | 83.0 | −58 | Tobramycin & Carbenicillin |
| 27. | Pseudomonas fluorenscens | 0.1 | NG | — | None |
| 28. | Staphylococcus aureus | 5.6 | 12.2 | +118 | Methicillin |

*No growth

CONCLUSIONS:
1. In 68% of the positive samples the new tube yielded more organisms/ml of blood. The difference ranged between a low of 5% and a high of 614% increased count.
2. The new system missed three positives while the original system missed five.
3. In four cases the original system gave a higher count. However, this level is well within expected experimental variability.
4. Thirty-six percent (36%) of the patients were not on antibiotics at the time of blood collection. The new system yielded higher counts in 50% of the cases. The difference ranged from a low of 134% and a high of 614% increase.
5. Seventeen (17) cultures were simultaneously positive at the same time. Two cultures (one Listeria and one Escherichia coli) were positive one day earlier in the new system.

As shown in the table, in 68% of the samples, the modified device containing the specimen transport system yielded higher counts (which ranged between 5% and 614% increase) than did the original device. In five instances, the original device was negative and the new device positive. Although the majority of samples were positive at the same time, there were two cases in which the new device detected a positive culture one day earlier (E. coli and one Listeria specimen). Surprisingly, the new device appears to yield greater counts even when the patient was not on antibiotics (3 patients). This indicates that the new device containing the specimen transport system more effectively blocked the patient's immune system than did the liquid blood treating solution of the original device.

EXAMPLE XIII

A first series of original lysis-centrifugation devices were assembled as described in Example VII. A second series of lysis-centrifugation devices were assembled the same as the second series of such devices in Example 5.

cushioning agent along with the following compounds in dry particulate powder form:

0.008 grams of thioglycolate;

0.048 grams of sodium polyanetholsulfonate; and 0.018 grams of purified saponin.

The tubes in the third series were evacuated sufficient to draw 8 milliliters of blood. This series of tubes was then heated to 121° C. for 30 minutes and then allowed to cool to room temperature.

In each instance, the stated amount of specific microorganisms and antibiotics (if any) as illustrated in Tables XII-1 through XII-6 below was added to 7.5 milliliters of blood in the first and second series of tubes and 8 milliliters of blood in the third series of tubes. The blood was then deposited into the respective lysis-centrifugation tube and each tube was subjected to centrifugation as described in this specification. Like quantities of each microbial pathogen-antibiotic combination were plated on both large and small petri plates as described in Example XI. The results are set forth in Tables XIII-1 through XIII-6 below:

TABLE XIII-1

| | Staphylococcus aureus | | | | | | | |
|---|---|---|---|---|---|---|---|---|
| | ORIGINAL | | | | NEW LIQUID | | | |
| | Small Plate | | Large Plate | | Small Plate | | Large Plate | |
| Antibiotics | % Recovery | S-Factor | % Recovery | S-Factor | % Recovery | S-Factor | % Recovery | S-Factor |

TABLE XIII-1-continued

*Staphylococcus aureus*

| | | | | | | | | |
|---|---|---|---|---|---|---|---|---|
| No Drug | 91 | .88 | * | * | 95 | 1.06 | * | * |
| Ampicillin | 84 | .033 | NT | NT | 99 | 1.10 | NT | NT |
| Cefamandole | 100 | .006 | 100 | .099 | 99 | .12 | 100 | .46 |
| Erythromycin | 100 | .06 | 100 | .85 | 83 | .068 | 100 | .64 |
| Vancomycin | 98 | .58 | * | * | 98 | .75 | * | * |

| | NEW POWDER | | | |
|---|---|---|---|---|
| | Small Plate | | Large Plate | |
| Antibiotics | % Recovery | S-Factor | % Recovery | S-Factor |
| No Drug | 95 | .95 | * | * |
| Ampicillin | 94 | .96 | NT | NT |
| Cefamandole | 50 | .03 | 99 | .31 |
| Erythromycin | 72 | .80 | * | * |
| Vancomycin | 52 | .76 | * | * |

*Unnecessary to test large plates
NT = Not tested

TABLE XIII-2

*Escherichia coli*

| | ORIGINAL | | | | NEW LIQUID | | | |
|---|---|---|---|---|---|---|---|---|
| | Small Plate | | Large Plate | | Small Plate | | Large Plate | |
| Antibiotics | % Recovery | S-Factor | % Recovery | S-Factor | % Recovery | S-Factor | % Recovery | S-Factor |
| No Drug | 98 | 1.17 | * | * | 98 | .78 | 94 | 1.5 |
| Cephalothin | 100 | .04 | 100 | .10 | 99 | .07 | 100 | .36 |
| Moxalactam | 38 | .021 | 75 | .008 | 100 | .10 | * | * |

| | NEW POWDER | | | |
|---|---|---|---|---|
| | Small Plate | | Large Plate | |
| Antibiotics | % Recovery | S-Factor | % Recovery | S-Factor |
| No Drug | 93 | 1.10 | * | * |
| Cephalothin | 95 | .76 | 92 | .83 |
| Moxalactam | 100 | .017 | 100 | .40 |

*Unnecessary to test large plates

TABLE XIII-3

*Streptococcus pneumoniae*

| | ORIGINAL | | | | NEW LIQUID | | | |
|---|---|---|---|---|---|---|---|---|
| | Small Plate | | Large Plate | | Small Plate | | Large Plate | |
| Antibiotics | % Recovery | S-Factor | % Recovery | S-Factor | % Recovery | S-Factor | % Recovery | S-Factor |
| No Drug | 92 | .70 | 94 | .81 | 84 | .76 | 95 | 1.00 |
| Ampicillin | 43 | .0084 | NT | NT | 81 | .52 | 95 | .25 |
| Cefoxitin | 97 | .39 | 100 | .16 | 99 | .51 | 100 | .27 |
| Penicillin | 76 | .024 | NT | NT | 87 | .57 | 93 | .43 |

| | NEW POWDER | | | |
|---|---|---|---|---|
| | Small Plate | | Large Plate | |
| Antibiotics | % Recovery | S-Factor | % Recovery | S-Factor |
| No Drug | 96 | .88 | 69 | .97 |
| Ampicillin | 65 | .60 | 85 | .88 |
| Cefoxitin | 99 | .28 | 99 | .77 |
| Penicillin | 63 | .78 | 63 | .87 |

NT = Not tested

TABLE XIII-4

*Enterobacter Cloacae*

| | ORIGINAL | | | | NEW LIQUID | | | |
|---|---|---|---|---|---|---|---|---|
| | Small Plate | | Large Plate | | Small Plate | | Large Plate | |
| Antibiotics | % Recovery | S-Factor | % Recovery | S-Factor | % Recovery | S-Factor | % Recovery | S-Factor |
| No Drug | 97 | 1.42 | * | * | — | — | * | * |
| Chloramphenicol | 98 | .91 | * | * | 89 | 1.6 | 97 | .93 |
| Tobramycin | 100 | .028 | 98 | .94 | 94 | .70 | 93 | 1.07 |

| | NEW POWDER |
|---|---|

TABLE XIII-4-continued

| | | Enterobacter Cloacae | | | |
|---|---|---|---|---|---|
| | | Small Plate | | Large Plate | |
| | | % Recovery | S-Factor | % Recovery | S-Factor |
| | No Drug | 98 | 1.20 | * | * |
| | Chloramphenicol | 80 | 1.15 | * | * |
| | Tobramycin | 75 | .85 | * | * |

*Unnecessary to test large plates
— Discontinued production of liquid tube (dry results only)

TABLE XIII-5

| | Pseudomonas aeruginosa | | | | | | | |
|---|---|---|---|---|---|---|---|---|
| | ORIGINAL | | | | NEW LIQUID | | | |
| | Small Plate % | | Large Plate % | | Small Plate % | | Large Plate % | |
| Antibiotics | Recovery | S-Factor | Recovery | S-Factor | Recovery | S-Factor | Recovery | S-Factor |
| Ampicillin | 97 | .56 | * | * | 87 | .84 | * | * |
| Barbenicillin | 97 | .125 | * | * | 92 | .85 | * | * |

| | | NEW POWDER | | | |
|---|---|---|---|---|---|
| | | Small Plate % | | Large Plate % | |
| | Antibiotics | Recovery | S-Factor | Recovery | S-Factor |
| | Ampicillin | 94 | .83 | * | * |
| | Barbenicillin | 56 | .92 | * | * |

*Unnecessary to test large plates

TABLE XIII-6

| | Klebsiella pneumoniae | | | | | | | |
|---|---|---|---|---|---|---|---|---|
| | ORIGINAL | | | | NEW LIQUID | | | |
| | Small Plate % | | Large Plate % | | Small Plate % | | Large Plate % | |
| Antibiotics | Recovery | S-Factor | Recovery | S-Factor | Recovery | S-Factor | Recovery | S-Factor |
| Barbenicillin | 93 | .143 | 92 | .54 | 93 | .66 | 88 | .72 |
| Cefoxitin | 49 | .02 | NT | NT | 72 | .86 | NT | NT |

| | | NEW POWDER | | | |
|---|---|---|---|---|---|
| | | Small Plate % | | Large Plate % | |
| | Antibiotics | Recovery | S-Factor | Recovery | S-Factor |
| | Barbenicillin | 94 | .76 | * | * |
| | Cefoxitin | 97 | .98 | NT | NT |

*Unnecessary to test large plates
NT = Not tested

As can be seen from the data above, the lysis-centrifugation devices made in accordance with the subject invention that contain the dry particulate powdered specimen transport system of the subject invention performed at least as well as the systems in accordance with this invention containing the specimen transport system in aqueous solution within the tube. Both of the new systems clearly out perform the original system as set forth in the Examples.

EXAMPLE XIV

Increasing Hold Time for Blood Specimens

A first series of original lysis-centrifugation devices were assembled as described in Example VII. A second series of lysis-centrifugation devices were assembled in the same manner as the third series of lysis-centrifugation devices which were used to obtain the data set forth in Tables XIII-1 through XIII-6 of Example XIII.

In each instance, the stated amount of specific microorganism as illustrated in Table XIV-1 below was added to 7.5 ml. of blood in the first series of tubes and to 8 ml. of blood in the second series of tubes. The blood was then deposited in the respective lysis-centrifugation tubes and the tubes were then held at 21° C. for the time period set forth in Table XIV-1 below. Each tube was next subjected to centrifugation and the concentrated contents plated on growth media as described in the specification.

As can be seen from the data set forth in Table XIV-1, certain species of bacteria propagate or die in the original tube when held for a period of 24 hours. Surprisingly, these same species did not substantially grow or die in the second series of new tubes containing the specimen transport system. While it is not recommended that the centrifugation tubes be held for lengthy periods of time, it has been found in the hospital environment that such tubes are held for time periods before processing. While the data shows no substantial propagation of most species within the new tube at 24 hours, it is believed that the tubes should be processed as quickly as possible and certainly before a hold time of 12 hours has been completed. Furthermore, to assure against growth of some species of bacteria such as *Enterobacter cloacae*, sodium chloride can be added, such as in the urine examples as set forth in Example XVII below. Sodium chloride can be present in an amount from about 0.1% to about 10% by weight of the final process treating solution and blood sample, and preferably in the range of from about 1% to about 5% and most preferably at about 3%.

As can be seen from Table XV-1 the beta-lactamase as an integral part of the specimen transport system will effectively function to block the activity of the antibiotic and prevent killing of the microbial pathogen while contained within the lysis-centrifugation tube.

TABLE XIV-1

BLOOD HOLD TIME RECONSTRUCTION CHECKS

| Organism | | CFU | % Recovery 2 HR | % Recovery 24 HR | S-Factor 2 HR | S-Factor 24 HR |
|---|---|---|---|---|---|---|
| *Haemophilus influenzae* | original | 501 | 86 | 91 | .8 ± .2 | .2 ± .1 |
| (19418) | new | 501 | 93 | 76 | .8 ± .1 | .5 ± .3 |
| *Streptococcus pyogenes* | original | 142 | 99.7 | 89 | .8 ± .3 | .4 ± .1 |
| (1344-2) | new | 142 | 100 | 100 | .9 ± .3 | .3 ± .1 |
| *Pseudomonas aeruginosa* | original | 332 | 99 | TNTC | 2.2 ± .8 | TNTC |
| (27853) | new | 332 | 95 | 94 | 1.2 ± .44 | .4 ± 2.6 |
| *Staphylococcus aureus* | original | 552 | 99 | 100 | .8 ± .03 | .03 ± .004 |
| (25923) | new | 1317 | 98 | 97 | 1.0 ± .3 | 1.5 ± .6 |
| *Escherichia coli* | original | 826 | 98 | TNTC | 1.7 ± .5 | TNTC |
| (25922) | new | 1057 | 100 | 100 | .9 ± .11 | .0 ± .4 |
| *Streptococcus pneumoniae* | original | 602 | 93 | 98 | 1.0 ± .3 | .8 ± .04 |
| (6301) | new | 360 | 90 | 99 | 1.0 ± .1 | 1.1 ± .2 |
| *Enterobacter cloacae* | original | 1236 | 98 | — | 1.2 ± .5 | TNTC |
| (1344-2) | new | 1236 | 99 | — | .9 ± .2 | TNTC |

TNTC = too numerous to count

EXAMPLE XV

Use of an Enzyme Component

A series of lysis-centrifugation devices were assembled the same as the second series of devices containing the specimen transport system as in Example XIV. To each tube was added 8 ml. of blood containing 842 CFU of *E. coli* and 20 ug/ml. of the antibiotic cefotaxime as well as the stated amount of beta-lactamase enzyme illustrated in Table XV-1 below. The beta-lactamase enzyme used was beta-lactamase (*Bacillus cereus*), lot No. 203435, order No. 426205, Calbiochem-Behring Corporation, La Jolla, California, NOTE: beta-lactamase I - 13 units of activity to beta-lactamase II - 1 unit of activity. The blood was then deposited into the respective lysis-centrifugation tubes and each tube was subjected to centrifugation as described in the specification. Like quantities of microbial pathogen-antibiotic-enzyme combination were plated on small petri plates as described in Example XI. The results are set forth in Table XV-1 below.

TABLE XV-1

*E. coli* - Cefotaxime 20 ug/ml.

| Units Of Enzyme | Percent Recovery | S-Factor |
|---|---|---|
| 0 | 58 | .02 |
| .01 | 100 | .011 |
| 0.1 | 100 | .052 |
| 1.0 | 99 | .33 |
| 2.0 | 99 | 1.17 |
| 4.0 | 99 | .82 |
| 5.0 | 99.8 | .95 |

As a comparison, a second series of tubes were assembled as described in Example 1 and to each tube was added 765 CFU of *E. coli*. 20 ug/ml. of cefotaxime, the units of beta-lactamase enzyme as illustrated in Table XV-2 and 7.5 ml. of blood. The tubes were then centrifuged and samples were cultured as described above, and the results are set forth in Table XV-2 below.

TABLE XV-2

| Units Of Enzyme | Percent Recovery | S-Factor |
|---|---|---|
| 0 | 93 | .08 |
| 1 | 90 | .04 |
| 5 | 95 | .155 |

The results of Table XV-2 when compared with Table XV-1 indicate that the addition of the enzyme does not satisfactorily improve the S values when used in a lysis-centrifugation tube which does not contain the specimen transport system.

Further tests were made comparing a first series of lysis-centrifugation tubes identical to those prepared in conjunction with Table XV-2 above and containing no specimen transport system; a second series of lysis-centrifugation tubes identical to those used in conjunction with Table XV-1 above but containing no enzyme; and a third series of lysis-centrifugation tubes which were the same as the second series of tubes but which contained the indicated amounts of beta-lactamase enzyme as set forth in Tables XV-3 through XV-8 below. The blood containing between 200 and 1000 CFU of the indicated bacteria was added to each tube and the tubes were processed as described above in this example and the results are set forth in Tables XV-3 through XV-8 below:

TABLE XV-3

| | | *Escherichia coli* 25922 | | | | | | | | | |
|---|---|---|---|---|---|---|---|---|---|---|---|
| | | First Series | Second Series of Tubes | Third series of Tubes With Enzyme Units | | | | | | | |
| Antibiotic | ug/ml | of Tubes | No Enzyme | .01 | .1 | 1. | 2. | 2.5 | 3. | 4. | 5. | 10. |
| Cephalothin | 20 | .04 | .05 | | | | .40 | .90 | | | 1.30 | |
| Cefamandole | 20 | .35 | .35 | | | 1.0 | .63 | | | | | |
| Cefoxitin | 25 | .27 | .76 | | | | .91 | | 1.76 | | | |

TABLE XV-3-continued

| | | | | Escherichia coli 25922 | | | | | | | |
|---|---|---|---|---|---|---|---|---|---|---|---|
| | | First Series | Second Series of Tubes | Third series of Tubes With Enzyme Units | | | | | | | |
| Antibiotic | ug/ml | of Tubes | No Enzyme | .01 | .1 | 1. | 2. | 2.5 | 3. | 4. | 5. | 10. |
| Cefotaxime | 20 | .08 | .02 | .01 | .05 | .33 | 1.2 | | | .82 | .95 | |
| Moxalactam | 100 | .02 | .01 | | | .03 | .05 | | .004 | | .04 | .002 |
| Moxalactam | 50 | | .03 | | | .04 | | | .05 | | | |
| Moxalactam | 40 | | .01 | | | .10 | | .22 | .12 | | .16 | |
| Moxalactam | 20 | | .33 | | | .20 | | | .16 | | .65 | |
| Moxalactam | 10 | | .84 | | | 1.01 | | | .92 | | | |
| Cefob | | .001 | .003 | | | .84 | | | 1.01 | | | |

TABLE XV-4

| | | | | Staphylococcus aureus 25923 | | | | | | | |
|---|---|---|---|---|---|---|---|---|---|---|---|
| | | First Series | Second Series of Tubes | Third Series of Tubes With Enzyme Units | | | | | | | |
| Antibiotic | ug/ml | of Tubes | No Enzyme | .01 | .1 | 1. | 2. | 2.5 | 3. | 4. | 5. | 10. |
| Cephalothin | 20 | .08 | .04 | .03 | .002 | .50 | .85 | | | | 1.65 | |
| Cefamandole | 20 | .006 | .03 | | | .81 | | | .62 | | .81 | |
| Cefotaxime | 20 | .28 | .52 | | | .96 | | | 1.02 | | | |
| Cefob | 50 | .009 | .025 | | | .72 | | | .80 | | | |

STS = Specimen Transport System

TABLE XV-5

| | | | | Klebsiella pneumoniae 632-2 | | | | | | | |
|---|---|---|---|---|---|---|---|---|---|---|---|
| | | First Series | Second Series of Tubes | Third Series of Tubes With Enzyme Units | | | | | | | |
| Antibiotic | ug/ml | of Tubes | No Enzyme | .01 | .1 | 1. | 2. | 2.5 | 3. | 4. | 5. | 10. |
| Cefotaxime | 20 | 0 | 0 | | | .03 | | | .58 | | | |
| Moxalactam | 20 | — | — | | | .23 | | | .22 | | | |

TABLE XV-6

| | | | | Enterobacter cloacae 1344-2 | | | | | | | |
|---|---|---|---|---|---|---|---|---|---|---|---|
| | | First Series | Second Series of Tubes | Third Series of Tubes With Enzyme Units | | | | | | | |
| Antibiotic | ug/ml | of Tubes | No Enzyme | .01 | .1 | 1. | 2. | 2.5 | 3. | 4. | 5. | 10. |
| Cefotaxime | 20 | .12 | .013 | | | .79 | | | .52 | | | |
| Moxalactam | 20 | — | — | | | .12 | | | .26 | | | |

STS = Specimen Transport System

TABLE XV-7

| | | | | Haemophilos influenzae 19418 | | | | | | | |
|---|---|---|---|---|---|---|---|---|---|---|---|
| | | First Series | Second Series of Tubes | Third Series of Tubes With Enzyme Units | | | | | | | |
| Antibiotic | ug/ml | of Tubes | No Enzyme | .01 | .1 | 1. | 2. | 2.5 | 3. | 4. | 5. | 10. |
| Cefotaxime | 20 | .003 | .001 | | | .153 | | | .46 | | | |
| Moxalactam | 40 | — | — | | | .005 | | | .004 | | | |

TABLE XV-8

| | | | | Streptococcus pneumoniae 6301 | | | | | | | |
|---|---|---|---|---|---|---|---|---|---|---|---|
| | | First Series | Second Series of Tubes | Third Series of Tubes With Enzyme Units | | | | | | | |
| Antibiotic | ug/ml | of Tubes | No Enzyme | .01 | .1 | 1. | 2. | 2.5 | 3. | 4. | 5. | 10. |
| Cefoxitin | 25 | .39 | .28 | | | .33 | | | .18 | | | |
| Cefotaxime | 20 | .001 | 0 | | | .23 | | | .62 | | | |

STS = Specimen Transport System

The data shown in Tables XV-3–XV-8 show that the addition of the enzyme to the specimen transport factor system of the subject invention effectively enhances the neutralization properties thereof for the above indicated class of antibiotics.

EXAMPLE XVI

Sterilization of Enzyme-Containing Specimen Transport System in a Specialized Apparatus Lysis-centrifugation tubes containing the antibiotic deactivation system utilized in the second series as set forth in Tables XV-3 through XV-8 above were made up. To a first series of these tubes was added the amount of beta-lactamase enzyme set forth in Table XVI-1 below. The tubes were then subjected to cobalt sterilization and thereafter 8 ml. of blood containing the microbial pathogen and the antibiotic as set forth in Table XVI-1 were added thereto and processed as set forth in Example XV. A second series of the tubes were steam sterilized and thereafter the indicated amount of beta-lactamase enzyme was added thereto and thereafter the 8 ml. of blood with the indicated amount of microbial pathogen and antibiotic was added thereto and the tubes were centrifuged and processed as set forth in Example XV. The results of these tests were set forth in Tables XVI-1 and XVI-3 below.

TABLE XVI-1

| | COBALT STERILIZATION | | | |
|---|---|---|---|---|
| | E. coli 25922 cefotaxime 20 ug/ml | | Staph. aureus 25923 cephalothin 20 ug/ml | |
| Units of Enzyme | Percent Recovery | S-Factor | Percent Recovery | S-Factor |
| 0.1 | 67 | .01 | 100 | .04 |
| 1.0 | 83 | .06 | 97 | .17 |
| 5.0 | 81 | .41 | 97 | .33 |

TABLE XVI-2

| | STEAM AUTOCLAVE STERILIZATION | | | |
|---|---|---|---|---|
| | E. coli 25922 cefotaxime 20 ug/ml | | Staph. aureus 25923 cephalothin 20 ug/ml | |
| Units of Enzyme | Percent Recovery | S-Factor | Percent Recovery | S-Factor |
| 0.1 | 100 | .05 | 17 | .002 |
| 1.0 | 99 | .33 | 26 | .50 |
| 5.0 | 99.8 | .95 | 34 | 1.65 |

As can be seen by a comparison of the data in Table XVI-1 with Table XVI-2, the loss of enzyme activity due to cobalt sterilization ranges from 20% to 80%, depending on the concentration of the enzyme. However, Table XVI-1 clearly illustrates that cobalt sterilization can be effectively utilized, and when used, increased amounts of the enzyme should be added to the tube prior to the sterilization. It should be noted that other chemicals are anticipated for use within the specimen transport system depending somewhat on the type of antimicrobial factors which are anticipated to be present in the sample. For example, other water-soluble compounds which are antagonistic to other classes of antimicrobial substances such as sodium hypochlorite, heavy metals and the like include substances like sodium bisulfite and sulfhydryls, for example. As indicated, the specimen transport system of the subject invention finds special utility in the lysis-centrifugation tube such as set forth in U.S. Pat. No. 4,131,512 and U.S. Pat. No. 4,212,948. In addition, the specimen transport system finds utility in the lysis-centrifugation tube as set forth in U.S. Pat. No. 4,164,449. In addition, the specimen transport system of the subject invention can be utilized in a blood treating tube for neonates which simply will include a standard single stopper vacuum tube designed to draw between 1 and 2 milliliters of blood. The tube would contain no substance other than the specimen transport system of the subject invention and saponin if desired. The blood can be treated upon injection in the tube and then directly plated upon growth media.

The above examples illustrate the beneficial effect of the specimen transport system of the subject invention when used in a lysis-centrifugation tube for analyzing microbial pathogens within blood samples. However, the specimen transport system of the present invention finds utility in protecting microorganisms in sample fluids other than blood which are collected and later analyzed for the presence of microbial pathogens. For example, the specimen transport system of the subject invention can protect microorganisms present in swabs, urine, sputum, spinal fluid and other body fluids during transit. It is well known that these fluids also contain both humoral and chemical antimicrobials (if the patient is being treated with antibiotics). With urine samples, the concentration of antibiotics may actually exceed that present in serum. An example of a modified specimen transport system for neutralizing antibiotics in urine is present in Example XVII below.

EXAMPLE XVII

Maintaining the Microbial Integrity of a Urine Specimen

The following example was performed to test the ability of the specimen transport system urine cocktail to block conventional therapeutic antibiotics and hold the microbial population, present in the urine, stable for up to 24 hours.

The following dry mixture was placed in each of a series of tubes:

0.03 grams of sodium polyanethosulfonate
0.005 grams of thioglycolate
0.1 grams of ICN free-base cysteine
0.1 grams of sodium bicarbonate.

The various antibiotics, listed in Tables XVII-1-XVII-6 below, were added, at the concentrations also specified therein, to the tubes containing the above-described specimen transport system urine cocktail and to an equal number of tubes without the urine cocktail. Five milliliters of sterile urine was then added to all tubes after which the tubes were vigorously mixed. Control tubes contained either urine alone or urine plus the above-described specimen transport system urine cocktail. No antibiotics were added to control tubes. The microorganisms listed in Tables XVII-1-XVII-6 below were adjusted to a McFarlin of 0.5 and then diluted 1:100 with sterile culture media. A 0.1 milliliter aliquot of a single microorganism was added to each urine containing tube and the resultant mixture vigorously agitated. A ten microliter aliquot from each tube containing the resultant mixture was immediately inoculated on tryptic soy agar plates and spread with a sterile spreader. The inoculated plates were incubated overnight in an environment and temperature appropriate for the microorganism employed. The tubes were then allowed to stand at room temperature for 24 hours. Additional ten microliter aliquots were plated as before herein described at the time intervals indicated in Tables XVII-1-XVII-6 below. All plating was done in quadruplicate and the S-Factor recorded as an average of the quadruplicate plating in Tables XVII-1-XVII-6 below.

TABLE XVII-1

Escherichia coli 25922

| Antibiotic** | Hour Time Points | | | |
|---|---|---|---|---|
| | 2 | 4 | 6 | 24 |
| *No Drug | — | .92 | 1.05 | .84 |
| No Drug | — | 2.01 | TNTC | TNTC |
| *Amikacin (210) | — | .73 | .62 | .33 |
| Amikacin (210) | — | 0 | 0 | 0 |
| *Ampicillin (210) | — | .92 | .75 | .70 |
| Ampicillin (210) | — | .02 | .001 | 0 |
| *Carbenicillin (200) | 1.12 | .90 | — | .31 |
| Carbenicillin (200) | .83 | .37 | — | .003 |
| *Cefamandole (200) | .88 | .45 | — | .31 |
| Cefamandole (200) | .37 | .33 | — | .005 |
| *Cefobid (500) | — | 1.16 | 1.63 | 1.68 |
| Cefobid (500) | — | .03 | 0 | 0 |
| *Cefotaxime (200) | — | 1.03 | 1.55 | 1.65 |
| Cefotaxime (200) | — | .009 | 0 | 0 |
| *Cefoxitin (250) | .72 | .33 | — | .17 |
| Cefoxitin (250) | .23 | .05 | — | .002 |
| *Cephalothin (200) | — | .47 | .86 | .53 |
| Cephalothin (200) | — | .01 | .01 | .04 |
| *Chloramphenicol (180) | — | 1.03 | 1.03 | .89 |
| Chloramphenicol (180) | — | 0 | 0 | 0 |
| *Erythromycin (80) | — | .70 | .75 | .59 |
| Erythromycin (80) | — | 1.36 | 1.49 | .42 |
| *Gantrisin (1000) | .70 | .93 | — | .56 |
| Gantrisin (1000) | 0 | 0 | — | 0 |
| *Gentamicin (60) | — | .81 | .38 | .28 |
| Gentamicin (60) | — | 0 | 0 | 0 |
| *Piperacillin (600) | .76 | .67 | — | .33 |
| Piperacillin (600) | .48 | .55 | — | .01 |
| *Tetracycline (90) | 1.12 | 1.16 | — | .56 |
| Tetracycline (90) | .20 | .02 | — | 0 |
| *Tobramycin (40) | — | 1.05 | 1.06 | .90 |
| Tobramycin (40) | — | 0 | 0 | 0 |

—Time point not included in reconstruction.
*Specimen transport system urine cocktail is present.
**Number in parenthesis represents final concentration (ug/ml) of antibiotic in urine
TNTC = too numerous to count

TABLE XVII-2

Klebsiella pneumoniae

| Antibiotic** | Hour Time Points | | |
|---|---|---|---|
| | 4 | 6 | 24 |
| *No Drug | 1.10 | 1.31 | 1.08 |
| No Drug | 1.00 | 3.7–TNTC | TNTC |
| *Amikacin (210) | .86 | .64 | .27 |
| Amikacin (210) | 0 | 0 | 0 |
| *Ampicillin (210) | 1.13 | 1.18 | .67 |
| Ampicillin (210) | 1.30 | TNTC | TNTC |
| *Carbenicillin (710) | 1.06 | .83 | .33 |
| Carbenicillin (710) | .15 | .01 | .03 |
| *Cefamandole (200) | 1.15 | 1.07 | .49 |
| Cefamandole (200) | .16 | .11 | .02 |
| *Cefobid (500) | .67 | .90 | .90 |
| Cefobid (500) | .007 | .007 | 0 |
| *Cefotaxime (200) | 1.00 | 1.33 | 3.83 |
| Cefotaxime (200) | .02 | .008 | .015 |
| *Cefoxitin (250) | .64 | .80 | .49 |
| Cefoxitin (250) | .04 | .05 | .14 |
| *Cephalothin (200) | .70 | .81 | .18 |
| Cephalothin (200) | .10 | .02 | .03 |
| *Chloramphenicol (180) | 1.22 | 1.07 | .59 |
| Chloramphenicol (180) | .84 | .87 | .39 |
| *Erythromycin (80) | 1.27 | 1.00 | 1.08 |
| Erythromycin (80) | 1.63 | 2.25 | TNTC |
| *Gantrisin (1000) | .82 | .67 | 1.00 |
| Gantrisin (1000) | 2.29 | .60–TNTC | 3.8–TNTC |
| *Gentamicin (60) | .94 | .73 | .22 |
| Gentamicin (60) | 0 | 0 | 0 |
| *Moxalactam (1000) | 3.48 | 3.52 | 2.30 |
| Moxalactam (1000) | .11 | 0 | 0 |
| *Piperacillin (600) | .52 | .84 | .46 |
| Piperacillin (600) | 1.07 | .15 | .34 |
| *Tetracycline (90) | .75 | 3.02 | .23 |
| Tetracycline (90) | .90 | .97 | .23 |
| *Tobramycin (40) | .85 | .95 | .53 |

TABLE XVII-2-continued

Klebsiella pneumoniae

| Antibiotic** | Hour Time Points | | |
|---|---|---|---|
| | 4 | 6 | 24 |
| Tobramycin (40) | 0 | 0 | 0 |

—Time point not included in reconstruction.
*Specimen transport system urine cocktail is present.
**Number in parenthesis represents final concentration (ug/ml) of antibiotic in urine
TNTC = too numerous to count

TABLE XVII-3

Pseudomonas aeruginosa

| Antibiotic** | Hour Time Points | | |
|---|---|---|---|
| | 4 | 6 | 24 |
| *No Drug | .92 | .77 | .53 |
| No Drug | 1.48 | 2.49 | TNTC |
| *Amikacin (210) | 1.33 | 1.41 | .47 |
| Amikacin (210) | .58 | .15 | .01 |
| *Carbenicillin (710) | 1.16 | 1.36 | .80 |
| Carbenicillin (710) | .88 | .38 | .08 |
| *Moxalactam (1000) | 1.10 | .86 | .41 |
| Moxalactam (1000) | .52 | .18 | .06 |
| *Piperacillin (600) | 1.54 | 1.05 | .91 |
| Piperacillin (600) | .32 | .98 | .23 |
| *Tobramycin (40) | .90 | .42 | 0.5 |
| Tobramycin (40) | .22 | .05 | 0 |

—Time point not included in reconstruction.
*Specimen transport system urine cocktail is present.
**Number in parenthesis represents final concentration (ug/ml) of antibiotic in urine
TNTC = too numerous to count

TABLE XVII-4

Proteus vulgaris

| Antibiotic** | Hour Time Points | | |
|---|---|---|---|
| | 4 | 6 | 24 |
| *No Drug | .57 | 1.07 | 3.11 |
| No Drug | .88 | 1.04 | TNTC |
| *Amikacin (210) | .72 | .92 | 1.67–swarm |
| Amikacin (210) | .15 | 0 | 0 |
| *Cefamandole (200) | .50 | .50 | .34 |
| Cefamandole (200) | .20 | .21 | .007 |
| *Piperacillin (600) | 2.17 | 1.80 | 3.7–swarm |
| Piperacillin (600) | 0 | 0 | 0 |
| *Tobramycin (40) | .67 | .92 | swarm |
| Tobramycin (40) | .18 | .03 | 0 |

—Time point not included in reconstruction.
*Specimen transport system urine cocktail is present.
**Number in parenthesis represents final concentration (ug/ml) of antibiotic in urine
TNTC = too numerous to count

TABLE XVII-5

Enterobacter cloaca

| Antibiotic** | Hour Time Points | | |
|---|---|---|---|
| | 4 | 6 | 24 |
| *No Drug | 1.0 | .77 | 2.47 |
| No Drug | 2.21 | 7.91 | TNTC |
| *Amikacin (210) | 1.12 | .62 | .11 |
| Amikacin (210) | 0 | 0 | 0 |
| *Ampicillin (210) | .99 | 1.68 | 3.60 |
| Ampicillin (210) | .18 | .07 | .02 |
| *Carbenicillin (710) | .76 | .76 | .14 |
| Carbenicillin (710) | .25 | .23 | .20 |
| *Cefamandole (200) | .89 | 1.44 | 1.11 |
| Cefamandole (200) | 1.13 | .48 | .44 |
| Cefobid (500) | .07 | .13 | .04 |
| Cefobid (500) | .03 | .003 | .0005 |
| *Cefotaxime (200) | .92 | 1.04 | .59 |
| Cefotaxime (200) | .12 | .02 | .05 |
| *Cefoxitin (250) | 1.01 | 1.14 | 2.1 |
| Cefoxitin (250) | .25 | .52 | 4.34 |
| *Cephalothin (200) | .88 | 1.03 | .49 |
| Cephalothin (200) | 2.41 | 4.37 | TNTC |
| *Chloramphenicol (180) | .97 | .94 | .94 |
| Chloramphenicol (180) | 1.06 | .97 | .76 |
| *Erythromycin (80) | .95 | 1.04 | 1.06 |

TABLE XVII-5-continued

*Enterobacter cloaca*

| Antibiotic** | Hour Time Points | | |
|---|---|---|---|
| | 4 | 6 | 24 |
| Erythromycin (80) | 1.23 | 1.27 | TNTC |
| *Gantrisin (1000) | .78 | 1.01 | .99 |
| Gantrisin (1000) | 1.74 | 4.02 | 1.04-TNTC |
| *Gentamicin (60) | .68 | .55 | .13 |
| Gentamicin (60) | 0 | 0 | 0 |
| *Moxalactam (1000) | 5.28 | 5.68 | 5.80 |
| Moxalactam (1000) | .10 | 0 | 0 |
| *Piperacillin (600) | .91 | .88 | 1.84 |
| Piperacillin (600) | .65 | .24 | .09 |
| *Tetracycline (90) | .85 | 1.73 | 1.23 |
| Tetracycline (90) | 1.03 | 2.43 | .58 |
| *Tobramycin (40) | .92 | .81 | 2.12 |
| Tobramycin (40) | 0 | 0 | 0 |

—Time point not included in reconstruction.
*Specimen transport system urine cocktail is present.
**Number in parenthesis represents final concentration (ug/ml) of antibiotic in urine
TNTC = too numerous to count

TABLE XVII-6

*Staphylococcus aureus*

*SPECIMEN TRANSPORT SYSTEM URINE
REGULAR URINE

| Antibiotic** | Hour Time Points | | | | |
|---|---|---|---|---|---|
| | 0 | 2 | 4 | 6 | 24 |
| *No Drug | 1.00 | — | .91 | 1.05 | 1.20 |
| No Drug | 1.00 | — | .98 | 1.06 | TN |
| *Amikacin (210) | 1.00 | — | .73 | .37 | .33 |
| Amikacin (210) | 1.00 | — | .071 | .008 | .001 |
| *Ampicillin (210) | 1.00 | .68 | .70 | — | .63 |
| Ampicillin (210) | 1.00 | 1.57 | 1.52 | — | .86 |
| *Carbenicillin (710) | 1.00 | .58 | .57 | — | .43 |
| Carbenicillin (710) | 1.00 | .70 | .80 | — | .37 |
| *Cefamandole (200) | 1.00 | .78 | .68 | — | .57 |
| Cefamandole (200) | 1.00 | .70 | .63 | — | .14 |
| *Cefobid (500) | 1.00 | — | 1.15 | 1.15 | 1.17 |
| Cefobid (500) | 1.00 | — | .58 | .42 | .08 |
| *Cefotaxime (200) | 1.00 | — | .83 | .82 | 1.00 |
| Cefotaxime (200) | 1.00 | — | 1.18 | .82 | .26 |
| *Cefoxitin (250) | 1.00 | .79 | .9 | — | .76 |
| Cefoxitin (250) | 1.00 | .79 | .57 | — | .21 |
| *Cephalothin (200) | 1.00 | — | .87 | 1.2 | 2.03 |
| Cephalothin (200) | 1.00 | — | .74 | 1.03 | .39 |
| *Chloramphenicol (180) | 1.00 | — | .73 | .80 | .63 |
| Chloramphenicol (180) | 1.00 | — | .41 | .28 | .086 |
| *Erythromycin (80) | 1.00 | — | .81 | .85 | .78 |
| Erythromycin (80) | 1.00 | — | .23 | .090 | .012 |
| *Gantrisin (1000) | 1.00 | — | .79 | .84 | .66 |
| Gantrisin (1000) | 1.00 | — | .89 | .21 | 2.22 |
| *Gentamicin (60) | 1.00 | — | .71 | .81 | .36 |
| Gentamicin (60) | 1.00 | — | .0 | 0 | 0 |
| *Moxalactam (1000) | 1.00 | — | .8 | .76 | .62 |
| Moxalactam (1000) | 1.00 | — | .86 | .65 | .26 |
| *Piperacillin (600) | 1.00 | .45 | .58 | — | .38 |
| Piperacillin (600) | 1.00 | .72 | .47 | — | .19 |
| *Tetracycline (90) | 1.00 | .64 | .73 | — | .73 |
| Tetracycline (90) | 1.00 | .067 | .012 | — | 0 |
| *Tobramycin (40) | 1.00 | — | 1.02 | .99 | .93 |
| Tobramycin (40) | 1.00 | — | .093 | .013 | 0 |

—Time point not included in reconstruction.
*Specimen transport system urine cocktail is present.
**Number in parenthesis represents final concentration (ug/ml) of antibiotic in urine
TNTC = too numerous to count Tables XVII-1–XVII-6 clearly demonstrate the ability of the specimen transport system urine cocktail to block conventional therapeutic antimicrobials in the urine and to hold the microbial count relatively constant in the absence of antimicrobials.

It should be noted that with normal urine minus antibiotics the common pathogenic organisms will grow (*E. coli, K. pneumonaie, P. aeruqinosa, P. vulqaris,* and *E. cloacae*) over a 24 hour period at room temperature. Hence, if the urine specimen is not analyzed promptly, it can lead to a false positive result. In the presence of average urine concentrations of antibiotics (10x that of blood serum) sensitive pathogenic organisms rapidly die. This could lead the laboratory to the conclusion that the specimen does not contain a significant number of pathogenic organisms ($10^5$) when in reality the specimen did contain the pathogens at this level at the time of collection. In other words, if two or more hours have elapsed between collection and laboratory processing, the count obtained may be as low as $10^3$, i.e., considered not significant.

The urine specimen transport system achieves two major improvements, namely:

1. It is capable of effectively blocking the cidal effects of antibiotics for at least 6 hours, and in the most of cases, for up to 24 hours.
2. The number of organisms present at time zero in the presence or absence of antibiotics remains constant for up to at least 6 hours.

In conclusion, the unique features of this urine specimen transport system allows the urine specimen to be held for up to 24 hours prior to processing with no deleterious effect on the microbial integrity of the sample. Refrigeration is not required, and the system is effective in the absence or presence of antimicrobials.

As can be seen from the above examples, the specimen transport system which falls within the scope of the subject invention has many uses. The ability of the specimen transport system to hold the microbial count constant may allow for detection of significant microbial species which would otherwise be masked by the overgrowth of more rapidly dividing organisms.

EXAMPLE XVIII

Increasing Hypertonicity to Create Heightened Backtriostatis Effect

The following dry mixture was placed in each of a series of tubes:

0.03 grams of sodium polyanethosulfonate
0.005 grams of thioglycolate
0.1 grams of ICN free-base cysteine
0.1 grams of sodium bicarbonate Various percentages, by weight thereof, of sodium chloride, indicated in Table XVIII-1 below were then added to individual tubes containing the above-described specimen transport system urine cocktail. A five milliliter aliquot of sterilized urine was then added to all tubes containing the above-described specimen transport system urine cocktail and to an equal number of tubes without the urine cocktail. Culture media containing *Enterobacter cloacae* ATCC #1344-2, was adjusted to a McFarlin of 0.5, representing approximately $5 \times 10^8$ microorganisms per milliliter of culture media, and then diluted 1:100 in sterile culture media. A 0.1 milliliter aliquot of diluted microorganisms was added to all urine containing tubes and the resulting mixture vigorously agitated. Ten microliter aliquots of the mixture were plated on agar plates such as described in Example VII. The remaining mixture was allowed to stand at room temperature for 24 hours after which time, a second ten microliter aliquot was plated as described in Example VII above. All plating was done in duplicate and the survival index (S-Factor) was calculated for each as described in the examples above. The average S-Factor for each time point was determined and is recorded in Table XVIII-1 below.

TABLE XVIII-1

| Enterobacter cloacae (ATCC # 1344-2) | | S-Factor | | |
|---|---|---|---|---|
| Sample | STS* | NaCl (%)** | 0 Hour | 24 Hours |
| 1 | — | — | 1.00 | TNTC*** |
| 2 | + | — | 1.00 | 1.72 |
| 3 | + | 1 | 1.00 | 1.27 |
| 4 | + | 2 | 1.00 | .80 |
| 5 | + | 4 | 1.00 | 1.03 |
| 6 | + | 8 | 1.00 | 0.69 |

*STS Specimen transport system urine cocktail
**percentage percentage sodium chloride by weight
***TNTC too numerous to count In the absence of the specimen transport system urine cocktail, see Sample 1 in Table XVIII-1 above, the microorganisms present in the urine will quickly multiply and thus prevent the clinician from obtaining an accurate count of the number of microorganisms per milliliter of urine.

The results, displayed in Table XVIII-1 above, indicate that while the specimen transport system urine cocktail can decrease the rate of microbial replication, the addition of such salts as sodium chloride increase the effectiveness of the urine cocktail in holding the bacterial count, in urine, stable over a 24-hour period. The preferred range of salt, as determined from the results displayed in Table XVIII-1 above, is from about 2.5 percent to about 4.0 percent, by weight thereof. From the results of the salt titration experiment above, it was concluded that addition of about three (3) percent, by weight, sodium chloride to the specimen transport system urine cocktail should prevent the overgrowth of *Enterobacter cloacae* in urine over a 24-hour period. To verify this conclusion, the specimen transport system urine cocktail prepared as described above, was added to a series of tubes. A second series of tubes was prepared by adding the identical cocktail plus 0.15 grams of sodium chloride, the equivalent of three (3) percent, by weight, sodium chloride. A third series of tubes were set aside without cocktail. A five-milliliter aliquot of sterile urine was then added to each tube, including those tubes without cocktail. Four strains of *Enterobacter cloacae*, identified in Table 40 below, were grown separately and adjusted to a McFarlin of 0.5. Each strain was then diluted 1:100 in sterile culture media and a 0.1 milliliter aliquot of each added to individual urine tubes as identified in Table XVIII-2 below. After vigorous mixing, a ten-microliter aliquot from each tube was plated on agar plates as described in Example XVII. Thereafter, the mixture was allowed to stand at room temperature and at the time intervals indicated in Table XVIII-2 below, another ten (10) microliter aliquot was plated as described in Example VII. The results of each time point given in Table XVIII-2 below represents an average survival index (S-Factor) for quadruplicate plating.

The results, given in Table XVIII-2 below, confirm an increased stabilization of colony formation for all four strains of *Enterobacter cloacae* afforded by addition of about three percent, by weight, sodium chloride to the specimen transport system cocktail.

Hypertonicity may also be increased by utilizing other salts, carbohydrates or sugars. It is expected that appropriate concentrations to approach the effect of sodium chloride in this example may be calculated with the knowledge disclosed herein.

TABLE XVIII-2

| Enterobacter cloacae (ATCC: various strains) Strain | S-Factor HOUR TIME POINTS* | | | | | | | | | | | |
|---|---|---|---|---|---|---|---|---|---|---|---|---|
| | 4 — | 4 +ADS | 4 +ADS+ NaCl | 6 — | 6 +ADS | 6 +ADS+ NaCl | 24 — | 24 +ADS | 24 +ADS+ NaCl | 48 — | 48 +ADS | 48 +ADS+ NaCl |
| 1344-2 | 3.2 | 1.28 | 1.97 | 4.75–TN | 1.23 | .91 | TN | 3.88–TN | 2.05 | TN | TN | 4.64–TN |
| 3118 | 3.00 | .87 | .98 | 3.00–TN | .95 | 1.05 | TN | 4.25–TN | .98 | TN | TN | 4.14 |
| 2294 | 2.5–TN | 1.00 | .76 | 5.53–TN | .89 | .89 | TN | 2.38–TN | .82 | TN | TN | 2.25 |
| 0879 | 2.5 | .95 | 1.03 | 4.02–TN | .86 | 1.06 | TN | TN | 1.07 | TN | TN | 1.29–TN |

*"—" indicates urine without specimen transport system cocktail; "+ADS" indicates urine plus specimen transport cocktail; "+ADS+NaCl" indicates specimen transport system cocktail containing 3 percent, by weight thereof, sodium choride.
TN = too numerous to count.

EXAMPLE XIX

Effect of Urine Specimen Transport System on Microbial Integrity in the Presence of Antibiotics Tables XIX-1–XIX-3 below illustrate the effect of the specimen transport system on quantitation in the presence and absence of the antibiotics over 24 hours.

The following dry mixture was placed in a series of sterile tubes:
- 0.03 grams sodium polyanetholsulfonate
- 0.005 grams thioglycolate
- 0.1 gram of ICN free-base cysteine
- 0.1 gram of sodium bicarbonate
- 0.15 grams of sodium chloride The various antibiotics, listed in Tables XIX-1–XIX-3 below, were added, at the concentrations also specified, to the tubes containing the above-described specimen transport system urine cocktail and to an equal number of tubes without the urine cocktail. Five milliliters of sterile urine was then added to all tubes after which the tubes were vigorously mixed. Control tubes contained either urine alone or urine plus the above-described specimen transport system urine cocktail. No antibiotics were added to control tubes. The microorganisms listed in Tables XIX-1–XIX-3 below were adjusted to a McFarlin of 0.5 and then diluted 1:100 with sterile culture media. A 0.1 milliliter aliquot of a single microorganism was added to each urine containing tube and the resultant mixture vigorously agitated. A ten-microliter aliquot from each tube containing the resultant mixture was immediately plated as described in Example XVII above. The tubes were then allowed to stand at room temperature for 24 hours. Additional ten microliter aliquots were plated as described in Example XVII above at the time points indicated in Tables XIX-1-X-IX-3 below. All plating was done in quadruplicate, and the S-Factors recorded in Tables XIX-1–XIX-3 below represent an average of the quadruplicate plating.

The results set forth in Tables XIX-1–XIX-3 indicate that the salt containing specimen transport system urine cocktail was able to hold the colony count of *Proteus vulgaris, Streptococcus, pneumoniae,* and *Streptococcus*

*pyogenes* relatively stable in both the presence and absence of most antibiotics.

TABLE XIX-1

| I. *Proteus vulgaris* (ATCC #23315) | S-Factor HOUR TIME POINTS* | | | | | |
|---|---|---|---|---|---|---|
| | 4 | | 6 | | 24 | |
| Antibiotic** | + | − | + | − | + | − |
| No Drug | 1.06 | 1.07 | 1.38 | 3.15 | 1.12 | TNTC |
| Ampicillin (210) | .77 | .19 | 1.19 | .04 | .87 | .004 |
| Cefoxitin (250) | .73 | .002 | .79 | .0008 | .25 | 0 |
| Chloramphenicol (180) | 1.01 | .53 | .56 | .32 | .46 | .06 |
| Erythromycin (80) | .79 | 1.13 | 1.50 | 1.78 | .94 | 1.07–TNTC |
| Gantrisin (1000) | 1.47 | .56 | 1.28 | 1.32 | 1.19 | TNTC |
| Mezlocillin (500) | 2.14 | .31 | 1.51 | .50 | 1.31 | 0 |

—Time point not included in reconstruction.
*Specimen transport system urine cocktail is present.
**Number in parenthesis represents final concentration of antibiotic in micrograms per milliliter of urine
TNTC = too numerous to count

TABLE XIX-2

| I. *Streptococcus pneumoniae* (ATCC #23315) | S-Factor HOUR TIME POINTS* | | | | | |
|---|---|---|---|---|---|---|
| | 4 | | 6 | | 24 | |
| Antibiotic** | + | − | + | − | + | − |
| No Drug | 1.19 | .82 | .95 | .73 | 1.27 | 4.80 |
| Ampicillin (210) | 1.60 | .54 | 1.34 | .43 | 1.08 | .07 |
| Cefamandole (200) | .42 | 1.04 | .75 | 1.12 | 1.36 | .28 |
| Cefoxitin (250) | 1.08 | .98 | 1.11 | .94 | 1.01 | .20 |
| Cephalothin (200) | 1.04 | .53 | 1.42 | .53 | 2.54 | .21 |
| Chloramphenicol (180) | .57 | .77 | .80 | .31 | 1.03 | .30 |
| Erythromycin (80) | .99 | .73 | .83 | .73 | .78 | .32 |
| Gantrisin (1000) | 1.00 | .96 | 1.00 | .96 | 1.10 | 14.54 |
| Mezlocillin (500) | 1.18 | .71 | 1.05 | .29 | 1.03 | .01 |

—Time point not included in reconstruction.
*Specimen transport system urine cocktail is present.
**Number in parenthesis represents final concentration of antibiotic in micrograms per milliliter of urine

TABLE XIX-3

| I. *Streptococcus pyogenes* (ATCC #23315) | S-Factor HOUR TIME POINTS* | | | | | |
|---|---|---|---|---|---|---|
| | 4 | | 6 | | 24 | |
| Antibiotic** | + | − | + | − | + | − |
| No Drug | 1.02 | 1.95 | .93 | 3.10 | .84 | TNTC |
| Ampicillin (210) | .90 | 1.50 | 1.00 | 1.50 | .79 | 1.00 |
| Cefamandole (200) | .52 | .41 | .88 | .09 | 1.28 | .26 |

TABLE XIX-3-continued

| I. *Streptococcus pyogenes* (ATCC #23315) | S-Factor HOUR TIME POINTS* | | | | | |
|---|---|---|---|---|---|---|
| | 4 | | 6 | | 24 | |
| Antibiotic** | + | − | + | − | + | − |
| Cefoxitin (250) | .60 | .30 | .94 | .24 | .96 | .10 |
| Cephalothin (200) | 1.35 | .63 | 1.50 | .58 | 1.62 | .08 |
| Chloramphenicol (180) | .84 | 1.15 | 1.05 | 1.06 | .75 | .22 |
| Erythromycin (80) | .54 | .97 | .33 | .81 | .54 | .76 |
| Gantrisin (1000) | .84 | 2.01 | .94 | 2.34 | .78 | 1.56–TNTC |
| Mezlocillin (500) | .95 | .74 | 1.33 | .51 | .62 | .10 |

—Time point not included in reconstruction.
*Specimen transport system urine cocktail is present.
**Number in parenthesis represents final concentration of antibiotic in micrograms per milliliter of urine
TNTC = too numerous to count

EXAMPLE XX

EFFECTIVE CONCENTRATION OF SODIUM POLYANETHOLSULFONATE (SPS) FOR A SPECIMEN TRANSPORT SYSTEM TO PRESERVE MICROBIAL INTEGRITY AN ANTIBIOTIC-CONTAINING URINE SPECIMEN

The following dry mixture was placed in each of a series of sterile tubes:

0.005 grams thioglycolate
0.1 gram ICN free-base cysteine
01. gram sodium bicarbonate
0.15 grams sodium chloride Different amounts of SPS, designated by weight percent thereof in Table XX-1 below, were added to the tubes containing the above-described specimen transport system urine cocktail and to the control tubes. The various antibiotics listed in Table XX-1 below were then added to one half of the tubes containing the above-described specimen transport system urine cocktail. Five milliliter aliquots of sterile urine were next added to all tubes. Control tubes containing urine but no antibiotic were established, half of which contained the above-described specimen transport system urine cocktail plus the various amounts of SPS designated in Table XX-1 below. *Staphylococcus aureus*, ATCC #25923, were grown, prepared and aliquoted into all tubes as described in Example XVII above. All tubes were plated as described in Example 11 above at the time points indicated in Table XX-1 below.

TABLE XX-1

| *Staphylococcus aureus* (ATCC #25923) | | S-Factor HOUR TIME POINTS* | | | | | | | |
|---|---|---|---|---|---|---|---|---|---|
| | | 2 | | 4 | | 6 | | 24 | |
| SPS %*** | Antibiotic** | + | − | + | − | + | − | + | − |
| — | No Drug | ND | ND | ND | 1.39 | ND | 1.50 | ND | 2.3–TNTC |
| 0.6 | No Drug | .70 | ND | 6.0 | ND | ND | ND | .44 | ND |
| 1.0 | No Drug | ND | ND | 1.4 | ND | .83 | ND | .66 | ND |
| 2.0 | No Drug | ND | ND | .85 | ND | .83 | ND | .91 | ND |
| 6.0 | No Drug | .87 | ND | .76 | ND | ND | ND | .63 | ND |
| 0.6 | Gentamicin (60) | .63 | .02 | .51 | 0 | ND | ND | .51 | 0 |
| 1.0 | Gentamicin (60) | ND | ND | 1.12 | 0 | 1.03 | .04 | 1.22 | 0 |
| 2.0 | Gentamicin (60) | ND | ND | .75 | 0 | .75 | 0 | .47 | 0 |
| 6.0 | Gentamicin (60) | .87 | .12 | .76 | .01 | ND | ND | .53 | 0 |
| 0.6 | Tetracycline (90) | .64 | .07 | .73 | .01 | ND | ND | .6 | 0 |
| 1.0 | Tetracycline (90) | ND | ND | 1.0 | 0.1 | 1.3 | 0 | .67 | 0 |
| 2.0 | Tetracycline (90) | ND | ND | .68 | 0 | .74 | .007 | .5 | .002 |

TABLE XX-1-continued

| Staphylococcus aureus (ATCC #25923) | | S-Factor HOUR TIME POINTS* | | | | | | |
|---|---|---|---|---|---|---|---|---|
| | | 2 | | 4 | | 6 | | 24 |
| SPS %*** | Antibiotic** | + | − | + | − | + | − | + | − |
| 6.0 | Tetracycline (90) | .91 | 1.09 | .87 | .34 | ND | ND | ND | ND |

—Time point not included in reconstruction.
*Specimen transport system urine cocktail is present.
**Number in parenthesis represents final concentration of antibiotic in micrograms per milliliter of urine.
***Final sodium polyetholsulfonate concentration, by weight thereof, per tube.
TNTC = too numerous to count
+Contains Specimen transport system.
−Does not contain Specimen transport system.
ND = Not Done The results set forth in Table XX-1 above reveal an optimum range for SPS in the specimen transport system urine cocktail to be between about 0.6% and about 2.0%, by weight thereof.

While this invention has been described in relation to its preferred embodiments, it is to be understood that various modifications thereof will now be apparent to one skilled in the art upon reading the specification and it is intended to cover such modifications as fall within the scope of the appended claims.

I claim:

1. An apparatus for the collection and treatment of microorganisms in a specimen comprising:
   (a) a container of generally elongated shape having a first end and a second end;
   (b) a piston slidably mounted in said container;
   (c) a shaft attached to said piston and extending through said first end, said shaft includes a narrow portion causing said shaft to break at said narrow portion when said shaft is bent;
   (d) a detachable cap removably attached to said second end
      said cap, said container and said piston forming a sealed chamber, in which the pressure in the chamber may be decreased by moving said piston toward said first end;
      said cap being puncturable for insertion of said specimen, and;
   (e) a water-soluble specimen transport system deposited in said container, said specimen transport system comprising a water-soluble additive at a concentration effective to prevent replication of microorganisms present in said specimen, when said specimen is mixed with said water additive therein to form a solution, and reducing the cidal activity toward said microorganisms of antimicrobial factors present in said specimen so that at least some microorganisms will be capable of replication upon dilution of said solution on medium capable of supporting replication of said microorganisms.

2. The apparatus according to claim 1, wherein said apparatus further comprises a means to lock said piston to prevent movement of said piston within said container, said means to lock comprises the narrow portion of said shift causing the shaft to break when said shaft is bent.

3. The apparatus of claim 1, further comprising:
   (f) a substance effective for preserving the viability of microorganisms of interest in said specimen in said container.

4. The apparatus of claim 3, wherein said substance for preserving the viability of said microorganisms of interest comprises a growth base effective for supporting the general nutritional needs of the microorganisms of interest.

5. The apparatus according to claim 3, wherein said substance for preserving the viability of the microorganisms of interest in the specimen comprises starch.

6. The apparatus according to claim 3, wherein said substance for preserving the viability of the microorganisms of interest in th specimen comprises agar.

7. The apparatus according to claim 3, wherein said substance for preserving the viability of the microorganisms of interest in the specimen comprises hemoglobin.

8. An apparatus for the collection and treatment of microorganisms in a specimen comprising:
   (a) a container of generally elongated shape having a first end and a second end;
   (b) a piston slidably mounted in said container;
   (c) a shaft attached to said piston and extending through said first end, said shaft being detachably connected to said piston by complementary thread means;
   (d) a detachable cap removably attached to said second end
      said cap, said container and said piston forming a sealed chamber, in which the pressure in the chamber may be decreased by moving said piston toward said first end;
      said cap being puncturable for insertion of said specimen, and;
   (e) a water-soluble specimen transport system deposited in said container, said specimen transport system comprising a water-soluble additive at a concentration effective to prevent replication of microorganisms present in said specimen, when said specimen is mixed with said water additive therein to form a solution, and reducing the cidal activity toward said microorganisms of antimicrobial factors present in said specimen so that at least some microorganisms will be capable of replication upon dilution of said solution on medium capable of supporting replication of said microorganisms.

9. The apparatus of claim 8 wherein said apparatus further comprises a means to lock said piston to prevent movement of said piston within said container, said means to lock comprises the complementary thread means allowing detachment of said shaft from said piston.

10. The apparatus of claim 8, further comprising:
    (f) a substance effective for preserving the viability of microorganisms of interest in said specimen in said container.

11. The apparatus of claim 10, wherein said substance for preserving the viability of said microorganisms of interest comprises a growth base effective for supporting the general nutritional needs of the microorganisms of interest.

12. The apparatus according to claim 10, wherein said substance for preserving the viability of the microorganisms of interest in the specimen comprises starch.

13. The apparatus according to claim 10, wherein said substance for preserving the viability of the microorganisms of interest in the specimen comprises agar.

14. The apparatus according to claim 10, wherein said substance for preserving the viability of the microorganisms of interest in the specimen comprises hemoglobin.

* * * * *

UNITED STATES PATENT AND TRADEMARK OFFICE
CERTIFICATE OF CORRECTION

PATENT NO. : 5,108,927

DATED :

INVENTOR(S) : Gordon L. Dorn

It is certified that error appears in the above-identified patent and that said Letters Patent is hereby corrected as shown below:

Col. 1, line 64, after "kidneys" insert --.--.
Col. 1, line 66, after "therapy" insert --.--.
Col. 2, line 3, after "health" insert --.--.
Col. 2, line 19, after "colonies" insert --.--.
Col. 3, line 11, after "Microbia" insert --l--.
Col. 4, line 13, after "problem" insert --.--.
Col. 4, line 31, after "isms" insert --.--.
Col. 4, line 36, after "remains" insert --.--
Col. 4, line 61, after "microbia" insert --l--.
Col. 4, line 65, after "lyzed" insert --.--.
Col. 6, line 18, after "quality" insert --.--.
Col. 8, line 67, change "plural" to --pleural--.
Col. 9, line 8, after employed insert --.--.
Col. 9, line 31, after "employs" delete "r".
Col. 12, line 61, after "discarded" insert --.--.
Col. 13, line 30, after "aperture" insert --.--.
Col. 16, line 68, change "uM" to --$\mu$M--.
Col. 17, line 13, change "uM" to --$\mu$M--.
Col. 17, line 20, after "admixture" insert --.--.
Col. 17, line 54, after "property" insert --.--.
Col. 18, line 3, after "HCl" insert --.--
Col. 19, line 5, after "specimen" insert --.--.
Col. 19, line 49, change "uM" to --$\mu$M--.
Col. 19, line 50, change "uM" to --$\mu$M--.
Col. 19, line 51, change "uM" to --$\mu$M--.

UNITED STATES PATENT AND TRADEMARK OFFICE
CERTIFICATE OF CORRECTION

PATENT NO. : 5,108,927
DATED : April 28, 1992
INVENTOR(S) : Gordon L. Dorn

It is certified that error appears in the above-identified patent and that said Letters Patent is hereby corrected as shown below:

Col. 19, line 53, change "uM" to --$\mu$M--.
Col. 19, line 54, change "uM" to --$\mu$M--.
Col. 19, line 54, change "uM" to --$\mu$M--.
Col. 20, line 11, change "uM" to --$\mu$M--.
Col. 20, line 11, change "uM" to --$\mu$M--.
Col. 20, line 50, after "admixture" insert --.--.
Col. 20, line 60, after "specimen" insert --.--.
Col. 22, line 6, change "ug" to --$\mu$g--.
Col. 23, line 56, change "ug" to --$\mu$g--.
Col. 23, line 58, change "ug" to --$\mu$g--.
Col. 23, line 59, change "ug" to --$\mu$g--.
Col. 23, line 61, change "ug" to --$\mu$g--.
Col. 23, line 63, change "ug" to --$\mu$g--.
Col. 23, line 65, change "ug" to --$\mu$g--.
Col. 23, line 62, left column of Table under Example II, delete "Ticarcillin".
Col. 23, line 63, left column of Table under Example II, before "(150 ug/ml)" insert --Ticarcillin--.
Col. 28, line 14, change "ug" to --$\mu$g--.
Col. 28, line 23, change "ug" to --$\mu$g--.
Col. 28, line 27, change "ug" to --$\mu$g--.
Col. 28, line 29, change "ug" to --$\mu$g--.
Col. 28, line 52, change "uM" to --$\mu$M--.
Col. 28, line 53, change "uM" to --$\mu$M--.
Col. 29, line 47, left column of Table VI-2 under heading "IV. Others" and beside "BACTRIM", change "Sufamethoxazole" to --Sulfamethoxazole--.

UNITED STATES PATENT AND TRADEMARK OFFICE
CERTIFICATE OF CORRECTION

PATENT NO. : 5,108,927

DATED : April 28, 1992

INVENTOR(S) : Gordon L. Dorn

It is certified that error appears in the above-identified patent and that said Letters Patent is hereby corrected as shown below:

Col. 30, Table VI-2, under heading "Averaged Recovery Values, Final Device Comparisons: Transport Time In Hours," beside "0 HR", insert --6 Hr--.

Col. 30, line 67, Table VI-2 under column headed "6 HR" "S.T.S." and beside "V. No Antibiotic," change ".92" to --.91--.

Col. 31, line 59, delete the first occurrence of "30".

Col. 32, line 16, Table VI-2, under column headed "48 HR" "Amies" and beside "V. No Antibiotic," change "18.93" to --18.94--.

Col. 32, line 43, change "configuration" to --centrifugation--.

Col. 36, line 9, change "articles" to --particles--.

Col. 36, line 57, change "he" to --the--.

Col. 37, line 26, after "of" delete "5".

Col. 37, line 27, after "gauge" insert --needle can be employed to remove all but about 1.3 to--.

Col. 38, line 59, change "genera" to --general--.

Col. 40, line 1, change "absorbed" to --sorbed--.

Col. 40, line 54, change "ug" to --$\mu$g--.

Col. 40, line 25, change "Gentamincin" to --Gentamicin--.

Col. 41, line 3, change "ug" to --$\mu$g--.

Col. 41, line 26, change "ug" to --$\mu$g--.

Col. 41, line 38, change "ug" to --$\mu$g--.

Col. 43, line 34, Table XI-1, under column headed "Antibiotics" change "Tontamycin" to --Tobramycin--.

Col. 45, line 21, Table XI-2, under column headed "Antibiotics" "II. Escherichia coli" change "#29522" to --#25922--.

UNITED STATES PATENT AND TRADEMARK OFFICE
CERTIFICATE OF CORRECTION

PATENT NO. : 5,108,927
DATED : April 28, 1992
INVENTOR(S) : Gordon L. Dorn

It is certified that error appears in the above-identified patent and that said Letters Patent is hereby corrected as shown below:

Col. 45, line 57, Table XI-3, under column headed "Large Plates" and across from "Tobramycin" change "88" to --98--.
Col. 48, line 22, Table XI-9, under the first column, change "Carbencillin" to --Carbenicillin--.
Col. 55, line 47, change "ug" to --$\mu$g--.
Col. 56, line 27, change "ug" to --$\mu$g--.
Col. 56, line 65, change "ug" to --$\mu$g--.
Col. 57, line 6, Table XV-3 second column, change "ug" to --$\mu$g--.
Col. 57, line 19, Table XV-4, second column, change "ug" to --$\mu$g--.
Col. 57, line 32, Table XV-5, second column, change "ug" to --$\mu$g--.
Col. 57, line 41, Table XV-6, second column, change "ug" to --$\mu$g--.
Col. 57, line 52, Table XV-7, second column, change "ug" to --$\mu$g--.
Col. 57, line 61, Table XV-8, second column, change "ug" to --$\mu$g--.
Col. 59, line 26, change "ug" to --$\mu$g--.
Col. 59, line 36, change "ug" to --$\mu$g--.
Col. 61, line 34, Table XVII-1, change "ug" to --$\mu$g--.
Col. 62, line 9, Table XVII-2, change "ug" to --$\mu$g--.
Col. 62, line 28, Table XVII-3, change "ug" to --$\mu$g--.
Col. 62, line 44, Table XVII-4, change "ug" to --$\mu$g--.
Col. 63, line 18, Table XVII-5, change "ug" to --$\mu$g--.

UNITED STATES PATENT AND TRADEMARK OFFICE
CERTIFICATE OF CORRECTION

PATENT NO. : 5,108,927

DATED : April 28, 1992

INVENTOR(S) : Gordon L. Dorn

It is certified that error appears in the above-identified patent and that said Letters Patent is hereby corrected as shown below:

Col. 63, line 55, Table XVII-6, change "ug" to --µg--.

Signed and Sealed this

Twelfth Day of July, 1994

*Attest:*

BRUCE LEHMAN

*Attesting Officer*     *Commissioner of Patents and Trademarks*